United States Patent
Eastham et al.

(10) Patent No.: US 9,334,227 B2
(45) Date of Patent: *May 10, 2016

(54) CARBONYLATION OF ETHYLENICALLY UNSATURATED COMPOUNDS

(75) Inventors: Graham Ronald Eastham, Redcar (GB); Mark Waugh, Redcar (GB); Philip Ian Richards, Redcar (GB)

(73) Assignee: Lucite International UK Limited, Southampton (GB)

( * ) Notice: Subject to any disclaimer, the term of this patent is extended or adjusted under 35 U.S.C. 154(b) by 781 days.

This patent is subject to a terminal disclaimer.

(21) Appl. No.: 12/084,575

(22) PCT Filed: Nov. 8, 2006

(86) PCT No.: PCT/GB2006/004156
§ 371 (c)(1),
(2), (4) Date: Feb. 19, 2009

(87) PCT Pub. No.: WO2007/057640
PCT Pub. Date: May 24, 2007

(65) Prior Publication Data
US 2009/0163724 A1 Jun. 25, 2009

(30) Foreign Application Priority Data

Nov. 17, 2005 (GB) .................... 0523402.6
Apr. 13, 2006 (GB) .................... 0607436.3
Jul. 20, 2006 (GB) .................... 0614377.0

(51) Int. Cl.
| | |
|---|---|
| C07C 51/14 | (2006.01) |
| C07C 67/38 | (2006.01) |
| C07F 7/08 | (2006.01) |
| C07F 9/28 | (2006.01) |
| C07C 67/31 | (2006.01) |
| B01J 31/24 | (2006.01) |
| C07C 51/09 | (2006.01) |

(52) U.S. Cl.
CPC ............ *C07C 67/31* (2013.01); *B01J 31/2414* (2013.01); *C07C 51/09* (2013.01); *C07C 67/38* (2013.01)

(58) Field of Classification Search
None
See application file for complete search history.

(56) References Cited

U.S. PATENT DOCUMENTS

| | | |
|---|---|---|
| 3,131,204 A | 4/1964 | Sisler et al. |
| 3,564,020 A | 2/1971 | Fenton |
| 4,245,115 A | 1/1981 | Butter |
| 4,377,708 A | 3/1983 | Morris |
| 4,500,727 A | 2/1985 | Kitamura et al. |
| 4,504,684 A | 3/1985 | Fox et al. |
| 4,517,061 A | 5/1985 | Fauvarque |
| 4,786,443 A | 11/1988 | Drent et al. |
| 4,818,810 A | 4/1989 | Drent |
| 4,835,250 A | 5/1989 | Drent |
| 4,868,282 A | 9/1989 | Van Broekhoven et al. |
| 4,880,903 A | 11/1989 | Van Broekhoven et al. |
| 4,900,413 A | 2/1990 | Tanaka et al. |
| 4,950,703 A | 8/1990 | Smutny |
| 4,960,926 A | 10/1990 | Drent |
| 4,960,949 A | 10/1990 | Devon et al. |
| 5,028,576 A | 7/1991 | Drent et al. |
| 5,099,062 A | 3/1992 | Drent et al. |
| 5,103,043 A | 4/1992 | Drent et al. |
| 5,149,868 A | 9/1992 | Drent |
| 5,158,921 A | 10/1992 | Drent et al. |
| 5,166,116 A | 11/1992 | Drent et al. |
| 5,177,253 A | 1/1993 | Drent et al. |
| 5,179,225 A | 1/1993 | Drent et al. |
| 5,189,003 A | 2/1993 | Klusener et al. |
| 5,210,280 A | 5/1993 | Drent |
| 5,245,098 A | 9/1993 | Hamilton et al. |
| 5,246,558 A | 9/1993 | Chevigne et al. |
| 5,258,546 A | 11/1993 | Klusener et al. |
| 5,350,876 A | 9/1994 | Drent et al. |
| 5,369,074 A | 11/1994 | Drent |
| 5,436,356 A | 7/1995 | Drent et al. |
| 5,563,308 A | 10/1996 | Spindler et al. |
| 5,565,594 A | 10/1996 | Spindler et al. |
| 5,618,983 A | 4/1997 | Burke |
| 5,710,344 A | 1/1998 | Breikss et al. |
| 5,719,313 A | 2/1998 | Drent et al. |
| 5,760,264 A | 6/1998 | Brieden |
| 5,773,661 A | 6/1998 | Unruh et al. |
| 5,783,715 A | 7/1998 | Pugin |
| 5,962,732 A | 10/1999 | Burke |

(Continued)

FOREIGN PATENT DOCUMENTS

| | | |
|---|---|---|
| AU | 2003259322 A1 | 2/2004 |
| AU | 2006314268 A1 | 5/2007 |

(Continued)

OTHER PUBLICATIONS

Clegg et al., Chem. Commun. 1999, pp. 1877-1878.*

(Continued)

*Primary Examiner* — Alicia L Otton
(74) *Attorney, Agent, or Firm* — Venable LLP; Keith G. Haddaway; Annette K. Kwok

(57) ABSTRACT

A process for the carbonylation of ethylenically unsaturated compounds including vinyl esters and a process for the production of 3-hydroxy propanoate esters or acids. The process comprises reacting said compound with carbon monoxide in the presence of a source of hydroxyl groups and of a catalyst system. The catalyst system is obtainable by combining: (a) a metal of Group 8, 9 or 10 or a compound thereof: and (b) a bidentate ligand of general formula (I): $X^1(X^2)$-$Q^2$-A-R—B-$Q^1$-$X^3(X^4)$.

19 Claims, No Drawings

(56) References Cited

U.S. PATENT DOCUMENTS

| | | |
|---|---|---|
| 6,015,919 A | 1/2000 | Pugin |
| 6,156,934 A | 12/2000 | Suykerbuyk et al. |
| 6,169,192 B1 | 1/2001 | Pugin et al. |
| 6,191,284 B1 | 2/2001 | Knochel et al. |
| 6,232,262 B1 | 5/2001 | Sielcken et al. |
| 6,258,979 B1 | 7/2001 | Kagan et al. |
| 6,284,919 B1 | 9/2001 | Pearson et al. |
| 6,284,925 B1 | 9/2001 | Knochel et al. |
| 6,307,065 B1 | 10/2001 | Tjaden et al. |
| 6,335,471 B1 | 1/2002 | Eastham et al. |
| 6,337,406 B1 | 1/2002 | Zhang |
| 6,348,621 B1 | 2/2002 | Wang et al. |
| 6,391,818 B1 | 5/2002 | Bonsel et al. |
| 6,462,095 B1 | 10/2002 | Bonsel et al. |
| 6,476,255 B1 | 11/2002 | Hadden et al. |
| 6,521,769 B1 | 2/2003 | Zhang |
| 6,706,912 B2 | 3/2004 | Drent et al. |
| 6,723,882 B2 | 4/2004 | Slany et al. |
| 6,737,542 B1 | 5/2004 | Drent et al. |
| 6,743,911 B2 | 6/2004 | Drent et al. |
| 6,753,450 B2 | 6/2004 | Ahlers et al. |
| 6,844,463 B2 | 1/2005 | Slany et al. |
| 6,916,954 B2 | 7/2005 | Schafer et al. |
| 6,982,357 B2 | 1/2006 | Crabtree et al. |
| 6,984,668 B1 | 1/2006 | Eastham et al. |
| 7,026,473 B2 | 4/2006 | Drent et al. |
| 7,129,367 B2 | 10/2006 | Suzuki et al. |
| 7,148,176 B2 | 12/2006 | Beller et al. |
| 7,265,240 B2 | 9/2007 | Eastham et al. |
| 7,371,705 B2 | 5/2008 | Eastham et al. |
| 7,629,470 B2 | 12/2009 | Campos et al. |
| 2001/0044556 A1 | 11/2001 | Drent et al. |
| 2001/0051745 A1 | 12/2001 | Pearson et al. |
| 2002/0016484 A1 | 2/2002 | Drent et al. |
| 2002/0045748 A1 | 4/2002 | Drent et al. |
| 2003/0191339 A1 | 10/2003 | Schfer et al. |
| 2004/0110989 A1 | 6/2004 | Slany et al. |
| 2004/0115475 A1 | 6/2004 | Hashimoto |
| 2004/0162440 A1 | 8/2004 | Bunel et al. |
| 2005/0090694 A1 | 4/2005 | Drent et al. |
| 2006/0106259 A1 | 5/2006 | Eastham et al. |
| 2006/0122435 A1 | 6/2006 | Eastham et al. |
| 2006/0128985 A1 | 6/2006 | Eastham et al. |
| 2006/0235241 A1 | 10/2006 | Drent et al. |
| 2006/0252935 A1 | 11/2006 | Eastham et al. |
| 2008/0051475 A1 | 2/2008 | Eastham et al. |
| 2008/0086015 A1 | 4/2008 | Eastham |
| 2008/0269459 A1 | 10/2008 | Drent et al. |
| 2008/0269520 A1 | 10/2008 | Drent et al. |
| 2009/0216041 A1 | 8/2009 | Eastham et al. |
| 2009/0234126 A1 | 9/2009 | Hartwig et al. |
| 2009/0312561 A1 | 12/2009 | Eastham et al. |
| 2010/0030036 A1 | 2/2010 | Mottram et al. |
| 2010/0113255 A1 | 5/2010 | Eastham et al. |
| 2010/0197958 A1 | 8/2010 | Eastham et al. |
| 2010/0324332 A1 | 12/2010 | Carrington-Smith et al. |
| 2012/0010413 A1 | 1/2012 | Abrecht et al. |

FOREIGN PATENT DOCUMENTS

| | | |
|---|---|---|
| BR | PI 9000965 A | 2/1991 |
| BR | PI 9510249-3 A | 11/1997 |
| BR | PI 0109239 A | 12/2002 |
| BR | PI 031289-7 A | 7/2005 |
| CA | 2498293 A1 | 3/2004 |
| CN | 1171098 A | 1/1998 |
| CN | 1429228 A | 7/2003 |
| CN | 1478071 A | 2/2004 |
| CN | 101137611 A | 3/2008 |
| CN | 101142162 A | 3/2008 |
| DE | 19745904 A1 | 4/1999 |
| DE | 19754304 A1 | 6/1999 |
| DE | 10023470 A1 | 11/2001 |
| DE | 10037961 A1 | 2/2002 |
| EP | 0-055-875 A1 | 7/1982 |
| EP | 0-106-379 A1 | 4/1984 |
| EP | 121965 A2 | 10/1984 |
| EP | 0144118 | 6/1985 |
| EP | 181014 A1 | 5/1986 |
| EP | 213671 A1 | 3/1987 |
| EP | 0-227-160 A2 | 7/1987 |
| EP | 0-235-864 A1 | 9/1987 |
| EP | 0-274-795 A2 | 7/1988 |
| EP | 0-282-142 A2 | 9/1988 |
| EP | 0305089 A1 | 3/1989 |
| EP | 0375573 A1 | 6/1990 |
| EP | 0-386-833 A1 | 9/1990 |
| EP | 0-441-447 A1 | 8/1991 |
| EP | 0-489-472 A2 | 6/1992 |
| EP | 0-495-547 A2 | 7/1992 |
| EP | 0-495-548 A2 | 7/1992 |
| EP | 0495347 A1 | 7/1992 |
| EP | 0495348 A1 | 7/1992 |
| EP | 0-499-329 A1 | 8/1992 |
| EP | 0577205 A2 | 1/1994 |
| EP | 0683764 A1 | 11/1995 |
| EP | 0728733 A1 | 8/1996 |
| EP | 0879642 A2 | 11/1998 |
| EP | 1330309 A1 | 7/2003 |
| FR | 2034147 A5 | 12/1970 |
| GB | 2006208 A | 5/1979 |
| JP | 6216737 A | 1/1987 |
| JP | 06-065148 A | 3/1994 |
| JP | 08134218 A | 5/1996 |
| JP | 10-511034 A | 10/1998 |
| JP | 10 339929 A | 12/1998 |
| JP | H0558949 A | 3/1999 |
| JP | 2001-517218 A | 10/2001 |
| JP | 2003-528849 A | 9/2003 |
| JP | 2004-515487 A | 5/2004 |
| JP | 2004-515537 A | 5/2004 |
| JP | 2008-505903 A | 2/2008 |
| JP | 2009-504620 A | 2/2009 |
| JP | 2009-533409 A | 9/2009 |
| JP | 2010511600 A | 4/2010 |
| JP | 2013063440 A | 4/2013 |
| JP | 5350592 B2 | 11/2013 |
| JP | 2014-208649 A | 11/2014 |
| KR | 2000-0076427 | 12/2000 |
| KR | 20050084042 A | 8/2005 |
| KR | 10-0851423 B1 | 8/2008 |
| TW | 524801 B | 3/2003 |
| TW | 552257 B | 9/2003 |
| TW | 200416212 | 9/2004 |
| TW | 200404773 | 4/2010 |
| TW | I410280 B | 10/2013 |
| WO | WO 96/19434 A1 | 6/1996 |
| WO | WO-9708124 A1 | 3/1997 |
| WO | WO 97/40001 * | 10/1997 ............ C07C 45/49 |
| WO | WO 98/41495 | 9/1998 |
| WO | WO 98/42717 A1 | 10/1998 |
| WO | WO-98/45040 | 10/1998 |
| WO | WO-99/47528 A1 | 9/1999 |
| WO | WO-00/56695 A1 | 9/2000 |
| WO | WO-01/10551 | 2/2001 |
| WO | WO-01/28972 A1 | 4/2001 |
| WO | WO-01/38336 A1 | 5/2001 |
| WO | WO-01/65583 A1 | 9/2001 |
| WO | WO 01/68583 A2 | 9/2001 |
| WO | WO-0168583 A2 | 9/2001 |
| WO | WO-0170659 | 9/2001 |
| WO | WO-01/72697 | 10/2001 |
| WO | WO-01/85662 A2 | 11/2001 |
| WO | WO-0187899 A1 | 11/2001 |
| WO | WO-0212161 | 2/2002 |
| WO | WO-02/46143 A1 | 6/2002 |
| WO | WO-02/48094 A1 | 6/2002 |
| WO | WO-03/040159 | 5/2003 |
| WO | WO 03/070370 A1 | 8/2003 |
| WO | WO-03070370 A1 | 8/2003 |
| WO | WO-2004/014834 A1 | 2/2004 |
| WO | WO-2004014552 | 2/2004 |
| WO | WO-2004/024322 A2 | 3/2004 |

(56) References Cited

FOREIGN PATENT DOCUMENTS

| WO | WO-2004/028689 A2 | 4/2004 |
|---|---|---|
| WO | WO-2004/050599 A1 | 6/2004 |
| WO | WO-2004050599 A1 | 6/2004 |
| WO | WO-2004/072088 A2 | 8/2004 |
| WO | WO 2004/103948 A1 | 12/2004 |
| WO | WO-2004/103948 A1 | 12/2004 |
| WO | WO-2005/003070 A1 | 1/2005 |
| WO | WO-2005/079981 A1 | 9/2005 |
| WO | WO-2005/082830 | 9/2005 |
| WO | WO 2005/082830 A1 | 9/2005 |
| WO | WO-2005082830 A1 | 9/2005 |
| WO | WO-2005118519 A1 | 12/2005 |
| WO | WO-2006/062467 A1 | 6/2006 |
| WO | WO-2006/084892 A2 | 8/2006 |
| WO | WO-2007/020379 A1 | 2/2007 |
| WO | WO-2007109365 A2 | 9/2007 |
| WO | WO-2007/119079 A1 | 10/2007 |
| WO | WO-2007119079 A1 | 10/2007 |
| WO | WO-2008/031750 A2 | 3/2008 |
| WO | WO-2008/075108 A1 | 6/2008 |
| WO | WO-2008145976 A1 | 12/2008 |
| WO | WO-2009010782 A1 | 1/2009 |

OTHER PUBLICATIONS

Doherty et al. Journal of Organometallic Chemistry, 640 (2001) pp. 182-196.*
Dorwald F. A. (Side Reactions in Organic Synthesis, 2005, Wiley: VCH, Weinheim p. IX of Preface.*
Office Action for U.S. Appl. No. 11/990,272, issued by the USPTO on Jul. 12, 2011.
Office Action for U.S. Appl. No. 10/589,971, issued by the USPTO on Mar. 22, 2011.
Wang et al., "Polymer-Bound Bidentate-Phosphine-Pallalium Complex as a Catalyst in the Heck Arylation", J. Org. Chem, vol. 59, No. 18, 1994, pp. 5358-5364.
Hofmann et al., "Bis(Di-T-Butylphosphino)Methane Complexes of Rhodium: Homogeneous Alkyne Hydrosilylation by Catalyst-Dependent Alkyne Insertion Into Rh—Si or Rh—H Bonds. Molecular Structures of the Dimer [(dtbpm) RHcL]$_2$ and of the Silyl Complex (dtbpm) Rh[Si(OEt)$^3$](PMe$_3$)", Journal of Organometallic Chemistry, vol. 490, 1995, pp. 51-70.
Lindner et al., "Catalytic Activity of Cationic Diphospalladium (II) Complexes in the Alkene/Co Copolymerization in Organic Solvents and Water in Dependence on the Length of the Alkyl Chain at the Phosphine Ligands", Journal of Organometallic Chemistry, vol. 602, 2000, pp. 173-187.
Richmond et al., "Preparation of New Catalysts by the Immobilization of Palladium(II) Species Onto Silica: An Investigation of Their Catalytic Activity for the Cyclization of Aminoalkynes", J. Am Chem. Soc., vol. 123, 2001, pp. 10521-10525.
Tamao et al., "Alkyl Group Isomerization in the Cross-Coupling Reaction of Secondary Alkyl Grignard Reagents With Organic Halides in the Presence of Nickel-Phosphine Complexes as Catalysts", Journal of the American Chemical Society, vol. 94, 1972, pp. 9268-9269.
Jones et al, "Rhodium-Catalyzed Activation and Functionalization of the C—C Bond of Biphenylene", Organometallics, vol. 20, 2001, pp. 5745-5750.
"Highly active [Pd(AcO)$_2$ (dppp(] catalyst for the CO—C$_2$H$_4$ copolymerization in H$_2$O—CH$_3$COOH solvent [dppp =1,3-bis (diphenylphosphino)propane]" Andrea Vavasori et al., Journal of Molecular Cat. A. Chem., vol. 204-205, 2003, pp. 295-303.
"Hydroesterification of styrene using an in situ formed Pd(OTs)$_2$(PPh$_3$)$_2$ complex catalyst", A. Seayad et al., Journal of Molecular Cat. A. Chem., vol. 151, 2000, pp. 47-59.
"Carbon monoxide-ethylene copolymerization catalyzed by a Pd(AcO)$_2$/dpppTsOH[1] system: the promoting effect of water and of the acid", Journal of Molecular Cat. A. Chem., vol. 110, 1996, pp. 13-23.

Kirk Othmer Encyclopaedia of Chemical Terminology, vol. 9, 4th Ed., p. 783, Hydrolysis of Organic Esters, pp. 783-785 and 787, John Wiley & Sons, Jan. 1994.
Masters, Christopher, "Homogeneous Transition Metal Catalysis," p. 4-21, Chapman and Hall, Feb. 1981.
Lide et al., Handbook of Chem and Phys., 76th Ed., CRC Press, 1995, ps. 8-141 6-155 to 6-177; 15-16 to 15-25.
Brunkan et al. "Effect of chiral cavities associated with molecularly imprinted platinum centers on the selectivity of ligand-exchange reactions at platinum", Journal of American Chemical Society, No. 22, pp. 6217-6225, (2000).
Brunkan et al. "Unorthodox C,O binding mode of Me$_2$BINOL in Pt(II) complexes", Journal of American Chemical Society, No. 120, pp. 11002-11003, (1998).
Andrews et al. "Regioselective complexation of unprotected carbohydrates by Platinum(II); Synthesis, structure, complexation equilibria, and hydrogen-bonding in carbonate-derived bis(phosphine)platinum(II) diolate and alditolate complexes", Journal of American Chemical Society, No. 116, pp. 5730-5740, (1994).
Hartwig, et al. "Structure and reactions of oxametallacyclobutanes and oxametallacyclobutenes of ruthenium", Organometallics, vol. 10, No. 9, pp. 3344-3362 (1991).
Konno et al. "Preparation and spectroscopic characteristics of geometrical isomers of bis[1,2-bis(dimethylphosphino)ethane]cobalt(III) complexes with thiolate ligands", The Chemical Society of Japan, No. 62, pp. 3475-3478, (1989).
Cecconi et al. "Palladium complexes with the tripodal phosphine tris(2-diphenylphosphinoethyl)amine. Synthesis and structure of trigonal, tetrahedral, trigonal bipyramidal, and square planar complexes", J. Chem. Soc. Dalton Trans., issue 1, pp. xvii-xx. (1989).
Miskowski et al. "Preparation and spectroscopic properties of Cobalt(III) complexes containing phosphine ligands. The electronic structural description of side-bonded dioxygen", Journal of American Chemical Society, vol. 98, No. 9, pp. 2477-2483, (1976).
Hayward et al. "Some reactions of peroxobis (triphenylphosphine)platinum(II) and analogs with carbon dioxide, carbon disulfide, and other unsaturated molecules", Journal of American Chemical Society, vol. 92, issue 20, pp. 5873-5878, (1970).
Osman, Serindag "Synthesis of some platinum(II) diphosphine complexes of the type [PtX2(P—P)] (X2=CO3; X=CH3COO, CF3COO, NCO)", Synth. React. Inorg. Met.-Org. Chem., vol. 27. No. 1, pp. 69-76, (1997).
Andrews et al. "Syntheses, spectra and structures of (diphosphine)platinum(II) carbonate complexes" Inorganic Chemistry, No. 35, pp. 5478-5483, (1996).
Latif et al. "Square planar platinum(II) complexes, crystal structures of cis-bis(triphenylphosphine) hydro(triphenylstannyl) platinum(II) and cis-bis(triphenylphosphine) hydro(triphenylsilyl) platinum(II)", Journal of Organometallic Chemistry, No. 474, pp. 217-221, (1994).
Becker et al. "Synthesis and characterization of chiral diphosphine platinum(II) VANOL and VAPOL complexes", Organometallics, No. 22, pp. 3245-3249, (2003).
Becker et al. "Imprinting chiral information into rigidified dendrimers", Organometallics, No. 22, pp. 4984-4998, (2003).
Peng et al. "Chiral rodlike platinum complexes, double helical chains and potential asymmetric hydrogenation ligand based on "linear" building blocks: 1,8,9,16-tetrahydroxytetraphenylene and 1,8,9,16-tetrakis(diphenylphosphino)tetraphenylene" Journal of American Chemical Society, No. 127, pp. 9603-9611, (2005).
Wen et al. "Synthesis, resolution, and applications of 1,16-dihydroxytetraphenylene as a novel building block in molecular recognition and assembly", Journal of Organic Chemistry, No. 68, pp. 8918-8931,(2003).
Mikami et al. "Molecular design of DABNTf as a highly efficient resolving reagent for racemic Pd complex with tropos biphenylphosphine (BIPHEP) ligand: circular dichroism (CD) spectra of enantiopure BIPHEP-Pd complex", Chirality, No. 15, pp. 105-107, (2003).
Tudor et al. "Diasteroisomer interconversion in chiral BiphepPtX$_2$ complexes", Organometallics, No. 19, pp. 4376-4384, (2000).

(56) References Cited

OTHER PUBLICATIONS

Bellabarba et al., "Synthesis, X-ray characterization and reactions of a trigonal planar palladium( )) carbonyl complex", Chemical Communications, No. 15, pp. 1916-1917, (2003).
Clegg et al., "Synthesis and reactivity of palladium hydrido-solvento complexes, including a key intermediate in the catalytic methoxycarbonylation of ethane to methypropanoate", Journal of the Chemical Society, Dalton Transactions, No. 17, pp. 3300-3308 (2002).
Clegg et al., "Characterisation and dynamics of [Pd(L-L)H(solv)]+, [Pd(L-L(CH2CH3)]+ and [Pd(L-L)(C(0)Et)(THF)]+ (L-L=1,2-(CH2PBut2)2C6H4): key intermediates in the catalytic methoxycarbonylation of ethane to methylpropanoate", Organometallics, vol. 21, No. 9, pp. 1832-1840 (2002).
Edelbach et al., "Catalytic hydrogenolysis of biphenylene with platinum, palladium, and nickelphosphine complexes", Organometallics, vol. 17, No. 22, pp. 4784-4794 (1998).
Kim et al., "Synthesis and theoretical study of palladium (II) complexes with aminophosphines as 7-membered chelate rings", Bulletin of the Korean Chemical Society, vol. 18, No. 11, pp. 1162-1166 (1997).
Reddy et al., "Unexpected cross-metathesis between Si—C and Si—Si bonds", Chemical Communications, No. 16, pp. 1865-1866 (1996).
Uchimaru et al., "Ring-opening polymerization of 1,1,2,2-tetramethyl-1,2-disilacyclopentane via palladium complex-catalysed Si—Si bond metathesis", Chemistry Letters, No. 2, p. 164 (1995).
Portnoy et al., "Reactions of electron-rich arylpalladium complexes with olefins. Origin of the chelate effect in vinylation catalysis", Organometallics, vol. 13, No. 9, pp. 3465-3479 (1994).
Wurst et al., "Synthesis and structure of the platinum (0) compounds [(dipb)Pt]2(COD) and (dipb)3Pt2 and of the cluster Hg6[Pt(dipb)]4 (dipb=(iPr)2P(CH2)4P(i-Pr)2)", Zeitschrift Für Anorganische Und Allgemeine Chemie, vol. 395, pp. 239-250 (1991).
Tanaka et al., "Synthesis of ketones via carbonylation of organic halides. II. Palladium-catalysed carbonylation of organic halides with terminal acetylenes in the presence of amines. Novel acetylenic ketone synthesis", Nippon Kagaku Kaishi, No. 3, pp. 537-546 (1985).
Molander et al., "Synthesis and application of chiral cyclopropane-based ligands in palladium-catalyzed allylic alkylation", Journal of Organic Chemistry, vol. 69, No. 23, pp. 8062-8069 (2004).
Brauer et al., "Reactions of coordinated ligands. XIV. Synthesis of a tetradentate phosphorus macrocycle in a palladium (II) template", Chemische Berichte, vol. 119, No. 1, pp. 349-365 (1986).
Dias et al., "Synthesis and characterization of .eta.5-monocyclopentadienyl (p-nitrobenzonitrile)ruthenium(II) salts: second harmonic generation powder efficiencies", Journal of Organometallic Chemistry, vol. 475, No. 1-2, pp. 241-245 (1994).
Pugh, R. I. et al. "Tandem isomerisation-carbonylation catalysis: highly active palladium(II) catalysts for the selective methoxycarbonylation of internal alkenes to linear esters", Chemical Communications—CHEMCOM, Royal Society of Chemistry, GB, No. 16, (Aug. 21, 2001), pp. 1476-1477.
Cullen et al, "Structure of the Hydrogenation Catalyst [(PP)Rh(NBD)]ClO4, (PP)=( 5-[(CH3)3C]2PC5H4)2Fe, and Some Comparative Rate Studies," Organometallics, vol. 2, pp. 714-719, 1983.
Abbenhuis et al., "Successful Application of a "Forgotten" Phosphine in Asymmetric Catalysis: A 9-Phosphabicyclo[3.3.1]non-9-yl Ferrocene Derivative as a Chiral Ligand," Organometallics, vol. 14, pp. 759-766, 1995.
Related U.S. Appl. No. 10/524,023, filed Nov. 17, 2005, Eastham et al.
Olah, George A., et al., "AlCl3-Catalyzed Dichlorophosphorylation of Saturated Hydrocarbons with PCl3 in Methylene Chloride Solution," J. Org. Chem., 1990, 55, 1224-1227.
Wei-Yong Yu, et al., "Preparation of Polymer-Protected Pt/Co Bimetallic Colloid and its Catalytic Properties in Selective Hydrogenation of Cinnamaldehyde to Cinnamyl Alcohol," Polymers for Advanced Technologies, GB, John Wiley and Sons, Chichester, Aug. 1, 1996, 719-722, vol. 7, No. 8.
Tolman, "Phosphorous Ligand Exchange Equilibria on Zerovalent Nickel. A Dominant Role for Steric Effects," Journal of the American Chemical Society, vol. 92, No. 10, pp. 2956-2965.
Tolman, "Steric Effects of Phosphorous Ligands in Organometallic Chemistry and Homogeneous Catalysis," Chemical Reviews, vol. 77, No. 3, pp. 313-348, (1976).
Grimmer, et al., "Zirconium bis-cyclopentadienyl compounds: An investigation into the influence of substituent effects on the ethene polymerisation behaviour of (CpR)$_2$ZrCl$_2$/MAO catalysts," Journal of Molecular Catalysis A: Chemical, vol. 188, No. 1-2, pp. 105-113, 2002.
Machine Translation of JP 08-134218, May 28, 1996.
Office Action for U.S. Appl. No. 11/597,787, issued by the USPTO on Oct. 8, 2008.
Office Action for U.S. Appl. No. 11/597,787, issued by the USPTO on Oct. 8, 2009.
Office Action for U.S. Appl. No. 11/597,787, issued by the USPTO on May 20, 2009.
Office Action for U.S. Appl. No. 10/561,912, issued by the USPTO on Aug. 25, 2008.
Office Action for U.S. Appl. No. 10/561,912, issued by the USPTO on Sep. 2, 2009.
Office Action for U.S. Appl. No. 10/561,912, issued by the USPTO on Jan. 14, 2008.
Office Action for U.S. Appl. No. 10/561,912, issued by the USPTO on Feb. 11, 2009.
Office Action for U.S. Appl. No. 10/536,801, issued by the USPTO on Apr. 8, 2008.
Office Action for U.S. Appl. No. 10/536,801, issued by the USPTO on Jan. 7, 2010.
Office Action for U.S. Appl. No. 10/536,801, issued by the USPTO on Jun. 17, 2009.
William Clegg et al: "Highly active and selective catalysts for the production of methyl propanoate via the methoxycarbonylation of ethane," Chem. Commun., 1999, pp. 1877-1878.
Julian G. Knight et al: "Remarkable Differences in Catalyst Activity and Selectivity for the Production of Methyl Propanoate versus CO-Ethylene Copolymer by a Series of Palladium Complexes of Related C$_4$-Bridged Diphosphines", Organometallics, vol. 19, No. 24, 2000, 4957-4967.
Adam J. Rucklidge et al.: "Methoxycarbonylation of vinyl acetate catalysed by palladium complexes of bis(ditertiarybutylphosphinomethyl) benzene and related ligands," Chem. Commun., 2005, pp. 1176-1178.
Office Action issued by the USPTO for U.S. Appl. No. 10/589,971 on Jul. 27, 2010.
Office Action issued by the USPTO in U.S. Appl. No. 12/518,320 on Dec. 8, 2010.
Oblad et al., Catalysis and Catalysts. In McKetta ed, Encyclopedia of Chemical Processing and Design, pp. 420-490, 1978.
Hartley, Supported Metal Complexes: A New Generation of Catalysts, Section 1.3, pp. 1, 9, 1985.
Armor, "Perspective: Do you really have a better catalyst?," Applied Catalysis A: General, vol. 282, pp. 1-4, 2005.
Hagen, "Industrial Catalysis: A Practical Approach," pp. v-xvii and 1-6, 2006.
Office Action for Taiwanese Application No. 094104929 issued by the Intellectual Property Office of Taiwan on Sep. 21, 2011.
Office Action for European Application No. 07848735.2, issued by the EPO on Sep. 9, 2011.
Office Action for Australian Application No. 2006314268, issued by the Australian Patent Office on Nov. 11, 2010.
Office Action for European Application No. 07824927.3, issued by the EPO on Mar. 30, 2011.
Office Action for GCC Application No. GCC/P/2007/8136 issued by the State Intellectual Property Office of the P.R. China on Nov. 5, 2010.
Office Action for Chinese Application No. 200580011699.0 issued by the State Intellectual Property Office of the P.R. China on Jun. 23, 2011.

(56) References Cited

OTHER PUBLICATIONS

Office Action for Japanese Application based on International Application No. PCT/GB2005/000569 issued by the Patent Office of Japan on Jun. 21, 2011.
Office Action for U.S. Appl. No. 12/297,023, issued by the USPTO on Sep. 27, 2011.
Office Action for U.S. Appl. No. 11/990,272, issued by the USPTO on Oct. 28, 2011.
Office Action for U.S. Appl. No. 12/518,320, issued by the USPTO on Dec. 6, 2011.
First Examination Report issued in Indian Application No. 841/MUMNP/2009 dated Nov. 29, 2012.
Notice of Allowance issued in U.S. Appl. No. 12/297,023 dated Dec. 26, 2012.
Notice of Allowance issued in U.S. Appl. No. 12/297,023 dated Feb. 21, 2013.
Office Action issued in Canadian Application No. 2,618,574 dated Dec. 7, 2012.
Office Action issued in Canadian Application No. 2,626,107 dated Nov. 23, 2012.
Office Action issued in Chinese Application No. 200580011699.0 dated Jan. 14, 2013.
Office Action issued in European Application No. 09 772 854.7 dated Oct. 5, 2012.
Office Action issued in Japanese Application No. 2008-540675 dated Nov. 13, 2012.
Office Action issued in Japanese Application No. 2009-538795 dated Feb. 19, 2013.
Office Action issued in Taiwanese Application No. 095128759 dated Jan. 3, 2013.
Office Action issued in Taiwanese Application No. 096113047 dated Jan. 22, 2013.
Office Action issued in U.S. Appl. No. 11/990,272 dated Feb. 6, 2013.
Office Action issued in U.S. Appl. No. 13/002,406 dated Mar. 15, 2013.
Kiss, "Palladium-catalyzed Reppe Carbonylation," Chem. Rev. 2001, 101(11): 3435 (Abstract Only).
Notice of Allowance issued in U.S. Appl. No. 11/990,272 dated Jul. 25, 2013.
Office Action issued in Indian Application No. 1366/DELNP/2003 dated Jul. 4, 2013.
Office Action issued in Mexican Application No. MX/a/2010/014404 dated Jun. 25, 2013.
Office Action issued in U.S. Appl. No. 13/002,406 dated Aug. 19, 2013.
Office Action issued in U.S. Appl. No. 10/589,971 dated Aug. 8, 2013.
White et al., "Basic Energy Sciences Advisory Committee Subpanel Workshop Report," Opportunities for Catalysis in the 21st Century, 2002, pp. 1-47.
Written Opinion of the Intellectual Property Office of Singapore issued in Application No. 201204384-0 dated Jul. 5, 2013.
Imwinkelried, "Catalytic Asymmetric Hydrogenation in the Manufacture of d-Biotin and Dextromethorphan," NSCS Spring Meeting 97: Industrial Asymmetric Synthesis, Chimia 51 (1997) 300-302.
Lee et al., "improved Catalysts for the Palladium-Catalyzed Synthesis of Oxindoles by Amide α-Arylation, Rate Acceleration, Use of Aryl Chloride Substrates, and a New Carbene Ligand for Asymmetric Transformations," J. Org. Chem, 2001, 66, 3402-3415.
Letter dated Nov. 27, 2013 reporting Office Action issued in Mexican Application No. MX/a/2010/014404.
Office Action issued in Australian Application No. 2010332501 dated Sep. 5, 2013.
Office Action issued in Chinese Application No. 200980125824.9 dated Oct. 15, 2013.
Office Action issued in Chinese Application No. 201080062848.7 dated Dec. 23, 2013.
Office Action issued in Eurasian Application No. 200970528 dated Nov. 18, 2013.
Office Action issued in Eurasian Application No. 201290514/28 dated Oct. 28, 2013.
Office Action issued in European Application No. 10172689.1 dated Dec. 5, 2013.
Office Action issued in European Application No. 10172698.2 dated Dec. 5, 2013.
Office Action issued in European Application No. 10803478.6 dated Dec. 20, 2013.
Office Action issued in Japanese Application No. 2011-515634 dated Dec. 17, 2013.
Office Action issued in Korean Application No. 10-2008-7014580 dated Jan. 15, 2014.
Office Action issued in Taiwanese Application No. 096145458 dated Oct. 9, 2013.
Office Action issued in U.S. Appl. No. 12/517,215 dated Mar. 12, 2014.
Office Action issued in U.S. Appl. No. 10/589,971 dated Mar. 6, 2014.
Argouarch, et al., "Synthesis of Some Ferrocene-Based 1,3(phosphanes) with Planar Chirality as the Sole Source of Chirality", European Journal of Organic Chemistry, 2000, vol. 16 pp. 2885-2891.
Examination Report issued by the State Intellectual Property Office of the P.R. China in Application No. GCC/P/2007/8136 dated Nov. 5, 2010.
Examiner's First Report issued in Australian Application No. 2007327051 dated May 9, 2012.
Godard, et al., "Systematic Study of the Asymmetric Methoxycarbonylation of Styrene Catalyzed by Palladium Systems Containing Chiral Ferrocenyl Diphosphine Ligands", Helvetica Chimica Acta, 2006 vol. 89(8) pp. 1610-1622.
Gray et al., "The Di-*t*-Butylphosphinyl Directed *ortho* Metalation Group, Synthesis of Hindered Dialkylarylphosphines," Synlett Letters, vol. 4, pp. 422-424 (1998).
International Preliminary Report on Patentability issued in Application No. PCT/GB2010/052093 dated Jun. 28, 2012.
International Search Report issued in International Application No. PCT/GB2009/050780 dated Oct. 15, 2009.
International Search Report issued in International Application No. PCT/GB2010/052093 dated Apr. 8, 2011.
International Search Report issued in International Application No. PCT/GB2010/052214 dated Mar. 30, 2011.
Japanese Notice of Reasons for Rejection issued in Application No. 2008-525618 dated Apr. 3, 2012.
Japanese Notice of Reasons for Rejection issued in Application No. 2008-540675 dated May 22, 2012.
Kraatz et al., "The reactions of tridentate cationic palladium (II) complexes with olefins and nucleophiles," The Journal of Organometallic Chemistry, vol. 488, No. 1, pp. 223-232 (1995).
Ooka et al., "Highly active and selective palladium catalyst for hydroesterification of styrene and vinyl acetate promoted by polymeric sulfonic acids," Chemical Communications, pp. 1173-1175 (2005).
Rucklidge, et al., "Methoxycarbonylation of vinyl acetate catalysed by palladium complexes of bis(ditertiarybutylphosphinomethyl) benzene and related ligands", Chemical Communications, 2005, vol. 9 pp. 1176-1178.
Russian Office Action issued in Application No. 201170142/28 dated Apr. 20, 2012.
United Kingdom Search Report issued in Application No. GB 1000078.4 dated May 6, 2010.
United Kingdom Search Report issued in Application No. GB0812297.0 dated Jun. 17, 2009.
United Kingdom Search Report issued in Application No. GB0921876.9 dated Oct. 29, 2010.
Wang, et al., "Synthesis and Use in Asymmetric Hydrogenations of Solely Planar Chiral 1,2-Disubstituted and 1,2,3-Trisubstituted Ferrocenyl Diphosphines: A Comparative Study", Organometallics, 2007, vol. 26, pp. 3530-3540.
Written Opinion of the International Searching Authority issued in International Application No. PCT/GB2009/050780 dated Oct. 15, 2009.
Written Opinion of the International Searching Authority issued in International Application No. PCT/GB2010/052093 dated Apr. 8, 2011.
Written Opinion of the International Searching Authority issued in International Application No. PCT/GB2010/052214 dated Mar. 30, 2011.

(56) References Cited

OTHER PUBLICATIONS

Office Action issued in Chinese Application No. 200780044657.6 dated Mar. 20, 2013.
Office Action issued in Chinese Application No. 200980125824.9 dated Feb. 22, 2013.
Office Action issued in European Application No. 09 772 854.7 dated Apr. 23, 2013.
Office Action issued in Korean Application No. 10-2008-7006106 dated Apr. 24, 2013.
Office Action issued in Malaysian Application No. PI20092250 dated Mar. 29, 2013.
Office Action issued in Mexican Application No. MX/a/2008/001974 dated Mar. 11, 2013.
Office Action issued in Taiwanese Application No. 096145458 dated Mar. 8, 2013.
Office Action issued in Taiwanese Application No. 095141340 dated Apr. 12, 2013.
Office Action for U.S. Appl. No. 12/297,023, issued by the USPTO on Apr. 12, 2012.
Andrews et al., "Syntheses, Spectra, and Structures of (Diphosphine)platinum(II) Carbonate Complexes," Inorganic Chemistry, vol. 35, No. 19, pp. 5478-5483, 1996.
Office Action issued in Korean Patent Office on Jan. 12, 2012, English translation.
Office Action for U.S. Appl. No. 11/990,272, issued by the USPTO on May 2, 2012.
Office Action for U.S. Appl. No. 12/517,215, issued by the USPTO on Feb. 27, 2012.
Letter Reporting Office Action issued in Australian Application No. 2009265367 dated Aug. 20, 2013.
Letter Reporting Office Action issued in Mexican Application No. MX/a/2009/005568 dated Sep. 12, 2013.
Office Action issued in Canadian Application No. 2,626,107 dated Aug. 8, 2013.
Office Action issued in Canadian Application No. 2,671,409 dated Aug. 23, 2013.
Office Action issued in Chinese Application No. 200780044657.6 dated Sep. 23, 2013.
Office Action issued in Eurasian Application No. 200801345 dated Jun. 27, 2013.
Office Action issued in Eurasian Application No. 201170142/28 dated Aug. 23, 2013.
Office Action issued in Eurasian Application No. 201290605 dated Aug. 22, 2013.
Office Action issued in Indian Application No. 3292/DELNP/2008 dated Sep. 20, 2013.
Office Action issued in Malaysian Application No. PI2011000006 dated Sep. 30, 2013.
Office Action issued in Singapore Application No. SE 2013 01311V dated Aug. 9, 2013.
Examination Report issued from the State Intellectual Property Office of P.R. China issued in Application No. GCC/P/2007/9585 dated Jan. 20, 2012.
Notice of Reason for Rejection issued from the Japanese Office Action in Japanese Application No. 2006-553662 dated Sep. 25, 2012.
Notice of Reason for Rejection issued from the Japanese Office Action in Japanese Application No. 2008-525618 dated Sep. 25, 2012.
Notice of Reasons for Rejection issued from the Japanese Patent Office in Japanese Application No. 2009-504833 dated Jul. 31, 2012.
Notice of Reexamination issued from the Patent Reexamination Board of State Intellectual Property Office of P.R. China in Chinese Application No. 200580011699.0 dated Jul. 30, 2012.
Office Action issued from the Eurasian Patent Organization issued in Application No. 200970528/28 dated Aug. 15, 2012.
Notice of Allowance issued in U.S. Appl. No. 13/520,523 dated Jun. 23, 2014.
Office Action issued in U.S. Appl. No. 12/517,215 dated Jun. 24, 2014.
Notice of Allowance issued in U.S. Appl. No. 13/002,406 dated Jul. 3, 2014.
Pugh et al., "Methoxycaronylation versus Hydroacylation of Ethene; Dramatic Influence of the Ligand in Cationic Palladium Catalysis," Adv. Synth. Catal., 2002, vol. 344, No. 8, pp. 837-840.
Notice of Allowance issued in U.S. Appl. No. 13/002,406 dated Apr. 9, 2014.
Office Action issued in Brazilian Patent Application. PI0507805-9 dated Mar. 24, 2014.
Office Action issued in Canadian Patent Application No. 2,626,107 dated May 9, 2014.
Office Action issued in Chinese Patent Application No. 201080060676.X dated Jan. 27, 2014.
Office Action issued in Eurasian Patent Application No. 200801345/28 dated Jan. 31, 2014.
Office Action issued in Eurasian Patent Application No. 201290605 dated Mar. 12, 2014.
Office Action issued in European Patent Application No. 09772854.7 dated Mar. 11, 2014.
Office Action issued in European Patent Application No. 10172689.1 dated May 30, 2014.
Office Action issued in European Patent Application No. 10172698.1 dated May 30, 2014.
Office Action issued in Gulf Cooperation Council Patent Application No. GCC/P/2005/17210 dated Mar. 5, 2014.
Office Action issued in Japanese Patent Application No. 2009-538795 dated Jan. 21, 2014.
Office Action issued in Japanese Patent Application No. 2013-051058 dated Apr. 8, 2014.
Office Action issued in Korean Patent Application No. 10-2009-7012397 dated Jan. 22, 2014.
Office Action issued in Malaysia Patent Application No. PI20081580 dated Feb. 14, 2014.
Office Action issued in Mexican Application No. MX/a/2010/014404 dated Mar. 31, 2014.
Office Action issued in Mexican Patent Application No. MX/a/2009/005568 dated Mar. 10, 2014.
Office Action issued in Taiwanese Patent Application No. 098122672 dated Mar. 4, 2014.
Office Action issued in Taiwanese Patent Application No. 095141340 dated Mar. 21, 2014.
Office Action issued in U.S. Appl. No. 12/084,575 dated Apr. 25, 2014.
Office Action issued in Eurasian Application No. 201170142 dated Mar. 7, 2014.
Office Action issued in U.S. Appl. No. 13/516,176 dated Mar. 6, 2015.
Corrected Notice of Allowability issued in U.S. Appl. No. 10/589,971 dated Mar. 24, 2015.
Office Action issued in U.S. Appl. No. 12/517,215 dated Apr. 6, 2015.
Notice of Allowance issued in U.S. Appl. No. 10/589,971 dated Dec. 5, 2014.
Notice of Allowance issued in U.S. Appl. No. 13/520,523 dated Oct. 14, 2014.
Office Action issued in U.S. Appl. No. 12/517,215 dated Nov. 14, 2014.
Office Action issued in U.S. Appl. No. 13/516,176 dated Oct. 9, 2014.
Supplemental Notice of Allowance issued in U.S. Appl. No. 13/520,523 dated Feb. 10, 2015.
Office Action issued in U.S. Appl. No. 12/517,215 dated Jul. 21, 2015.
Office Action issued in U.S. Appl. No. 13/516,176 dated Aug. 19, 2015.
G. Marc Loudon, Organic Chemistry, third edition, Chapter 2.4. E. Classification of Carbon Substitution, p. 63-64.
Office Action issued in U.S. Appl. No. 13/516,176 dated Jan. 22, 2016.
Office Action issued in U.S. Appl. No. 12/517,215 dated Jan. 4, 2016.

\* cited by examiner

CARBONYLATION OF ETHYLENICALLY UNSATURATED COMPOUNDS

The present invention relates to the carbonylation of ethylenically unsaturated compounds.

The carbonylation of ethylenically unsaturated compounds using carbon monoxide in the presence of an alcohol or water and a catalyst system comprising a group 6, 8, 9 or 10 metal, for example, palladium, and a phosphine ligand, for example an alkyl phosphine, cycloalkyl phosphine, aryl phosphine, pyridyl phosphine or bidentate phosphine, has been described in numerous European patents and patent applications, for example EP-A-0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable high reaction rates to be achieved. C3 alkyl bridges between the phosphorous atoms are exemplified in EP0495548 together with tertiary butyl substituents on the phosphorous.

WO96/19434 subsequently disclosed that a particular group of bidentate phosphine compounds having a substituted aryl bridge could provide remarkably stable catalysts which require little or no replenishment; that use of such bidentate catalysts leads to reaction rates which are significantly higher than those previously disclosed, and that little or no impurities are produced at high conversions.

WO 01/68583 discloses rates for the same process as WO 96/19434 when used for higher alkenes and when in the presence of an externally added aprotic solvent.

EP0495548B1 gives an example of vinyl acetate carbonylation employing the C3 bridged phosphine 1,3 bis(di-tert-butylphosphino) propane. The rates quoted are 200 moles product per mole of Pd per hour and the result is the production of 1 and 2-acetoxy methyl propanoate in a ratio of 40:60 (linear:branched).

WO 98/42717 discloses a modification to the bidentate phosphines used in EP0495548 wherein one or both phosphorous atoms are incorporated into an optionally substituted 2-phospha-tricyclo[3.3.1.1{3,7}]decyl group or a derivative thereof in which one or more of the carbon atoms are replaced by heteroatoms ("2-PA" group). The examples include a number of alkoxycarbonylations of ethene, propene and some higher terminal and internal olefins. In addition, hydroformylation of vinyl acetate giving a branched:linear product ratio of 10:1 is also disclosed. Notably, no alkoxy or hydroxycarbonylation of vinyl acetate is disclosed.

WO 03/070370 extends the teaching of WO 98/42717 to bidentate phosphines having 1, 2 substituted aryl bridges of the type disclosed in WO96/19434. The suitable olefin substrates disclosed include several types having various substituents. Notably, vinyl esters are not mentioned either generally or specifically.

WO 04/103948 describes both the above types of ligand bridges as useful for butadiene carbonylation and WO 05/082830 describes a selection of WO 04/103948 where the tertiary carbon substituents are different on the respective phosphorous atoms.

According to a first aspect of the present invention there is provided a process for the carbonylation of ethylenically unsaturated compounds comprising reacting said compound with carbon monoxide in the presence of a source of hydroxyl groups and of a catalyst system, the catalyst system obtainable by combining:

(a) a metal of Group 8, 9 or 10 or a compound thereof: and
(b) a bidentate ligand of general formula (I)

$$X^1(X^2)\text{-}Q^2\text{-}A\text{-}R\text{---}B\text{-}Q^1\text{-}X^3(X^4) \qquad (I)$$

wherein:
A and B each independently represent lower alkylene;
R represents a cyclic hydrocarbyl structure having at least one non-aromatic ring to which the $Q^1$ and $Q^2$ atoms are linked on available adjacent cyclic atoms of the at least one ring and which is substituted with at least one substituent on at least one further non-adjacent cyclic atom of the at least one ring; wherein each adjacent cyclic atom to the said available adjacent cyclic atom is not substituted so as to form a further 3-8 atom ring structure via the other adjacent cyclic atom to the said available adjacent cyclic atoms in the at least one ring or via an atom adjacent to the said other adjacent atom but outside the at least one ring;
the groups $X^1$, $X^2$, $X^3$ and $X^4$ independently represent univalent radicals up to 30 atoms having at least one tertiary carbon atom or $X^1$ and $X^2$ and/or $X^3$ and $X^4$ together form a bivalent radical of up to 40 atoms having at least two tertiary carbon atoms wherein each said univalent or bivalent radical is joined via said at least one or two tertiary carbon atoms respectively to the appropriate atom $Q^1$ or $Q^2$; and
$Q^1$ and $Q^2$ each independently represent phosphorous, arsenic or antimony.

By the term one further non-adjacent cyclic atom is meant any further cyclic atom in the ring which is not adjacent to any one of said available adjacent cyclic atoms to which the $Q^1$ and $Q^2$ atoms are linked.

For the avoidance of doubt, references to Group 8, 9 or 10 metals herein should be taken to include Groups 8, 9 and 10 in the modern periodic table nomenclature. By the term "Group 8, 9 or 10" we preferably select metals such as Ru, Rh, Os, Ir, Pt and Pd. Preferably, the metals are selected from Ru, Pt and Pd. More preferably, the metal is Pd.

Advantageously, the ring structure of the R group in the present invention prevents undue rigidity by avoiding ring structures or bridges involving the cyclic atoms immediately adjacent to the said available adjacent cyclic atoms or a non-ring atom adjacent to such adjacent atoms. Surprisingly, the inventors have discovered that introducing rigidity into the ring structure so close to the active site is disadvantageous and that beneficial effects are observed through more flexible steric influences (supplied by appropriate ring substitution) than through further proximate rigidity in the ring. This may be due to the relatively flexible constraints supplied by steric influences compared with inflexible ring rigidity. Such flexible steric constraints may allow the incoming metal atom to adopt the most favourable interaction position which would be denied by further ring rigidity close to the said available adjacent cyclic atoms. Accordingly, excluded from this aspect of the invention are norbornyl type bridges at the ring atoms adjacent to the available adjacent ring atoms or the like such as 1,8 Cineolyl. These structures introduce too much rigidity into the ring close to the active site.

Accordingly, the cyclic atoms adjacent to the said available adjacent cyclic atoms may be themselves substituted as long as they do not form part of further adjacent ring structures as defined herein. Suitable substituents may otherwise be selected from those defined for the said at least one further non-adjacent cyclic atom(s) defined herein.

For the avoidance of doubt, references to the cyclic atoms adjacent to the said available adjacent cyclic atoms or the like is not intended to refer to one of the said two available adjacent cyclic atoms themselves. As an example, a cyclohexyl ring joined to a $Q^1$ atom via position 1 on the ring and joined to a $Q^2$ atom via position 2 on the ring has two said further non adjacent cyclic atoms as defined at ring position 4 and 5 and two adjacent cyclic atoms to the said available adjacent cyclic atoms at positions 3 and 6.

The term a non-aromatic ring means that the at least one ring to which the $Q^1$ and $Q^2$ atom are linked via B & A respectively is non-aromatic, and aromatic should be interpreted broadly to include not only a phenyl type structure but other rings with aromaticity such as that found in the cyclopentadienyl ring of ferrocenyl, but, in any case, does not exclude aromatic substituents on this non-aromatic at least one ring.

Advantageously, use of the catalyst system of the present invention in the carbonylation of ethylenically unsaturated compounds such as ethylene, propylene, butadiene, pentenenitrile, octene, etc gives high rates of reaction for both alkoxy- and hydroxycarbonylation but especially with hydroxycarbonylation. A further advantage of the carbonylation reactions of the present invention is the greatly increased TON with both alkoxy- and hydroxycarbonylation but especially with alkoxycarbonylation.

Advantageously, use of the catalyst system of the present invention in the carbonylation of ethylenically unsaturated compounds which can provide linear or branched products such as pentene nitrites or vinyl esters gives predominantly linear product for both alkoxy- and hydroxycarbonylation but especially with hydroxycarbonylation. This is surprising because hydroformylation of vinyl acetate using a 2-phospha-adamantyl ligand with a propane bridge gave predominantly branched product in WO 98/42717. A further advantage of the carbonylation reactions of the present invention is the greatly increased reaction rates and TON with both alkoxy- and hydroxycarbonylation but especially with alkoxycarbonylation.

References to ethylenically unsaturated compounds herein should be taken to include any one or more unsaturated C—C bond(s) such as those found in alkenes, alkynes, conjugated and unconjugated dienes, functional alkenes etc.

The substituents on the said at least one further non adjacent cyclic atom may be selected to encourage greater stability but not rigidity of conformation in the cyclic hydrocarbyl structure. The substituents are, therefore, selected to be of the appropriate size to discourage or lower the rate of non-aromatic ring conformation changes. Such groups may be independently selected from lower alkyl, aryl, het, hetero, halo, cyano, nitro, —$OR^{19}$, —$OC(O)R^{20}$, —$C(O)R^{21}$, $C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$ or —$CF_3$, more preferably, lower alkyl, or hetero most preferably, $C_1$-$C_6$ alkyl. Where there are two or more said further non-adjacent cyclic atoms in the at least one ring they may each be independently substituted as detailed herein. Accordingly, where two such further non adjacent cyclic atoms are substituted, the substituents may combine to form a further ring structure such as a 3-20 atom ring structure. Such a further ring structure may be saturated or unsaturated, unsubstituted or substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, lower alkyl (which alkyl group may itself be unsubstituted or substituted or terminated as defined herein) or unsubstituted or substituted Het, wherein $R^{19}$ to $R^{30}$ each independently represent hydrogen, unsubstituted or substituted aryl or unsubstituted or substituted lower alkyl, and/or be interrupted by one or more (preferably less than a total of 4) oxygen, nitrogen, sulphur, silicon atoms or by silano or dialkyl silicon groups or mixtures thereof.

Particularly preferred further non-adjacent cyclic atom substituents are methyl, ethyl, propyl, isopropyl, phenyl, oxo, hydroxy, mercapto, amino, cyano and carboxy. Particularly preferred substituents when two or more further non adjacent cyclic atoms are substituted are x,y-dimethyl, x,y-diethyl, x,y-dipropyl, x,y-di-isopropyl, x,y-diphenyl, x,y-methyl/ethyl, x,y-methyl/phenyl, saturated or unsaturated cyclopentyl, saturated or unsaturated cyclohexyl, 1,3 substituted or unsubstituted 1,3H-furyl, un-substituted cyclohexyl, x,y-oxo/ethyl, x,y-oxo/methyl, disubstitution at a single ring atom is also envisaged, typically, x,x-lower dialkyl. More typical substituents are methyl, ethyl, n-propyl, isopropyl, n-butyl, isobutyl, t-butyl, or oxo, most typically methyl or ethyl, or oxo most typically, methyl; wherein x and y stand for atom positions in the at least one ring.

Typically, the maximum rate (moles of product/moles of group 8, 9 or 10 metal/hour) for the carbonylation reaction, especially, hydroxy- or alkoxy-carbonylation of the first aspect is close to or greater than that for 1,3-bis(di-t-butylphosphino)propane reacted under the same conditions. Typically, the group 8, 9 or 10 metal is palladium.

Preferably, further substitution of said cyclic hydrocarbyl structure is not on said available adjacent carbon atoms to which said $Q^1$ and $Q^2$ atoms are linked. The cyclic hydrocarbyl structure may be substituted at one or more said further cyclic atoms of the at least one ring but is preferably substituted at 1, 2, 3 or 4 such cyclic atoms, more preferably 1, 2 or 3, most preferably at 1 or 2 such cyclic atoms of the at least one ring. The substituted cyclic atoms may be carbon or hetero but are preferably carbon. For instance, in a ring of cyclic atoms wherein the $Q^1$ and $Q^2$ atoms are linked to cyclic atoms 1 and 2 respectively, substitution is preferably at one or more positions 4 to n−1 ie. positions 4 and/or 5 in a 6 membered ring (position 6 being n), positions 4, 5 and/or 6 in a seven membered ring and position 4 only in a 5 membered ring etc.

When there are two or more substituents on the said at least one ring they may meet to form a further ring structure unless excluded herein. However, it is preferred that substituents attached to said adjacent cyclic atoms to the said available adjacent cyclic atoms do not meet with substituents on the other said adjacent cyclic atoms to form further ring structures at all as these may render the active site too rigid.

Preferably, the cyclic hydrocarbyl structure which is substituted by A and B at available adjacent positions on the at least one ring has a cis-conformation with respect to the relevant cyclic bond and the A and B substituents.

Preferably, the cyclic hydrocarbyl structure has from 5 up to 30 cyclic atoms, more preferably from 4 up to 18 cyclic atoms, most preferably from 4 up to 12 cyclic atoms and when monocyclic, especially 5 to 8 cyclic atoms and, in any case, may be monocyclic or polycyclic. The cyclic atoms may be carbon or hetero, wherein references to hetero herein are references to sulphur, oxygen and/or nitrogen. Typically, the cyclic hydrocarbyl structure has from 2 up to 30 cyclic carbon atoms, more preferably from 3 up to 18 cyclic carbon atoms, most preferably from 3 up to 12 cyclic carbon atoms and, when monocyclic, especially 3 to 8 cyclic carbon atoms and in any case, may be monocyclic or polycyclic and may or may not be interrupted by one or more hetero atoms. Typically, when the cyclic hydrocarbyl structure is polycyclic it is preferably bicyclic or tricyclic. The cyclic hydrocarbyl structure as defined herein may include unsaturated bonds insofar as the said available adjacent cyclic atoms to which the $Q^1$ and $Q^2$ atoms are linked are saturated and references to unsaturated cyclic hydrocarbyl structures should be understood accordingly. By cyclic atom is meant an atom which forms part of a cyclic skeleton.

The cyclic hydrocarbyl structure, apart from that it may be interrupted with hetero atoms and, subject to the definitions herein, may be saturated or unsaturated.

The cyclic hydrocarbyl structure may be selected from 4 and/or 5 lower alkylcyclohexane-1,2-diyl, 4 lower alkylcyclopentane-1,2-diyl, 4, 5 and/or 6 lower alkylcycloheptane-1,2-diyl, 4, 5, 6 and/or 7 lower alkylcyclooctane-1,2-diyl, 4, 5, 6, 7 and/or 8 lower alkylcyclononane-1,2-diyl, 5 and/or 6 lower alkyl piperidinane-2,3-diyl, 5 and/or 6 lower alkyl morpholinane-2,3-diyl, O-2,3-isopropylidene-2,3-dihydroxyethane-2,3-diyl, cyclopentan-one-3,4-diyl, cyclohexanone-3,4-diyl, 6-lower alkyl cyclohexanone-3,4-diyl, 1-lower alkyl cyclopentene-3,4-diyl, 1 and/or 6 lower alkyl cyclohexene-3,4-diyl, 2 and/or 3 lower alkyl cyclohexadiene-5,6-diyl, 5 lower alkyl cyclohexen-4-one-1,2-diyl, adamantyl-1-2-diyl, 5 and/or 6 lower alkyl tetrahydropyran-2,3 diyl, 6-lower alkyl dihydropyran-2,3 diyl, 2-lower alkyl 1,3 dioxane-5,6-diyl, 5 and/or 6 lower alkyl-1,4 dioxane-2,3-diyl, 2-lower alkyl pentamethylene sulphide 4,5-diyl, 2-lower alkyl-1,3 dithiane-5,6-diyl, 2 and/or 3-lower alkyl 1,4 dithiane-5,6-diyl, tetrahydro-furan-2-one-4,5-diyl, delta-valero lactone 4,5-diyl, gamma-butyrolactone 3,4-diyl, 2H-dihydropyrone 5,6-diyl, glutaric anhydride 3,4-diyl, 1-lower alkyl pyrollidine-3,4-diyl, 2,3 di-lower alkyl piperazine-5,6-diyl, 2-lower alkyl dihydro imidazole 4,5-diyl, 2,3,5 and/or 6 lower alkyl-1,4,7 triazacyclononane-8,9-diyl, 2,3,4 and/or 10 lower alkyl-1,5,9 triazacyclodecane 6,7-diyl, 2,3-di-lower alkyl thiomorpholine-5,6-diyl, 2-lower alkyl-thiazolidine 4,5-diyl, 4,5-diphenyl-cyclohexane-1,2-diyl, 4 and/or 5-phenyl-cyclohexane-1,2-diyl, 4,5-dimethyl-cyclohexane-1,2-diyl, 4 or 5-methylcyclohexane-1,2-diyl, 2, 3, 4 and/or 5 lower alkyl-decahydronaphthalene 8,9-diyl, bicyclo[4.3.0]nonane-3,4 diyl, 3a,4,5,6,7,7a-hexahydro-1H-inden-5,6-diyl, 1, 2 and/or 3 methyl-3a,4,5,6,7,7a hexahydro-1H-inden-5,6-diyl, Octahydro-4,7 methano-indene-1,2-diyl, 3a,4,7,7a-tetrahydro-1H-inden-5,6-diyl, 1, 2 and/or 3-dimethyl-3a,4,5,6,7,7a-hexahydro-1H-inden 5,6-diyls, 1,3-bis(trimethylsilyl)-3a,4,5,6,7,7a-hexahydro-3H-isobenzofuran-5,6-diyl.

Alternatively, the substituents on the said at least one further non adjacent cyclic atom may be a group Y where Y represents a group which is at least as sterically hindering as phenyl and when there are two or more substituents Y they are each as sterically hindering as phenyl and/or combine to form a group which is more sterically hindering than phenyl;

Steric hindrance in the context of the invention herein is discussed on page 14 et seq of "Homogenous Transition Metal Catalysis—A Gentle Art" by C. Masters, published by Chapman and Hall 1981.

Preferably, Y represents —$SR^{40}R^{41}R^{42}$ wherein S represents Si, C, N, S, O or aryl and $R^{40}R^{41}R^{42}$ are as defined herein. Preferably each Y and/or combination of two or more Y groups is at least as sterically hindering as t-butyl.

More preferably, when there is only one substituent Y, it is at least as sterically hindering as t-butyl whereas where there are two or more substituents Y, they are each at least as sterically hindering as phenyl and at least as sterically hindering as t-butyl if combined into a single group.

Preferably, when S is aryl, $R^{40}$, $R^{41}$ and $R^{42}$ are independently hydrogen, alkyl, —$BQ^3$-$X^3(X^4)$ (wherein B, $X^3$ and $X^4$ are as defined herein and $Q^3$ is defined as $Q^1$ or $Q^2$ above), phosphorous, aryl, arylene, alkaryl, arylenalkyl, alkenyl, alkynyl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, —$CF_3$, —$SiR^{71}R^{72}R^{73}$ or alkylphosphorous.

Preferably, when S is Si, C, N, S or O, $R^{40}$, $R^{41}$ and $R^{42}$ are independently hydrogen, alkyl, phosphorous, aryl, arylene, alkaryl, aralkyl, arylenalkyl, alkenyl, alkenyl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, —$CF_3$, $SiR^{71}R^{72}R^{73}$, or alkylphosphorous wherein at least one of $R^{40}$-$R^{42}$ is not hydrogen and wherein $R^{19}$-$R^{30}$ are as defined herein; and $R^{71}$-$R^{73}$ are defined as $R^{40}$-$R^{42}$ but are preferably $C_1$-$C_4$ alkyl or phenyl.

Preferably, S is Si, C or aryl. However, N, S or O may also be preferred as one or more of the Y groups in combined groups. For the avoidance of doubt, as oxygen or sulphur can be bivalent, $R^{40}$-$R^{42}$ can also be lone pairs.

Preferably, in addition to group Y, the aromatic structure may be unsubstituted or further substituted with groups selected from Y, alkyl, aryl, arylene, alkaryl, aralkyl, arylenalkyl, alkenyl, alkynyl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, —$CF_3$, —$SiR^{71}R^{72}R^{73}$, or alkylphosphorous wherein $R^{19}$-$R^{30}$ are as defined herein; and $R^{71}$-$R^{73}$ are defined as $R^{40}$-$R^{42}$ but are preferably $C_1$-$C_4$ alkyl or phenyl.

In addition, when S is aryl, the aryl may be substituted with in addition to $R^{40}$, $R^{41}$, $R^{42}$ any of the further substituents defined for the aromatic structure above.

More preferred Y substituents may be selected from t-alkyl or t-alkyl, aryl such as -t-butyl, —$SiMe_3$, or 2-phenylprop-2-yl, -phenyl, alkylphenyl-, phenylalkyl- or phosphinoalkyl- such as phosphinomethyl.

Preferably, when S is Si or C and one or more of $R^{40}$-$R^{42}$ are hydrogen, at least one of $R^{40}$-$R^{42}$ should be sufficiently bulky to give the required steric hindrance and such groups are preferably phosphorous, phosphinoalkyl-, a tertiary carbon bearing group such as -t-butyl, -aryl, -alkaryl, -aralkyl or tertiary silyl.

In some embodiments, there may be two or more said Y substituents on further aromatic cyclic atoms of the aromatic structure. Optionally, the said two or more substituents may combine to form a further ring structure such as a cycloaliphatic ring structure.

Some typical structures are shown below wherein R', R", R'", R"" etc are defined in the same way as the substituent on the at least one further non-adjacent cyclic atom above but may also be hydrogen, or represent the hetero atom being non substituted if linked directly to a hetero atom and may be the same or different and wherein at least one R' atom is not hydrogen or representing the hetero atom being non substituted if linked directly to a hetero atom. The diyl methylene linkages to the phosphorous (not shown) are shown in each case.

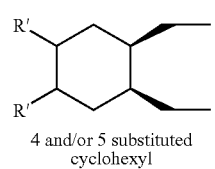

4 and/or 5 substituted cyclohexyl

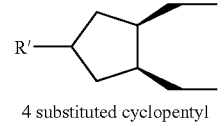

4 substituted cyclopentyl

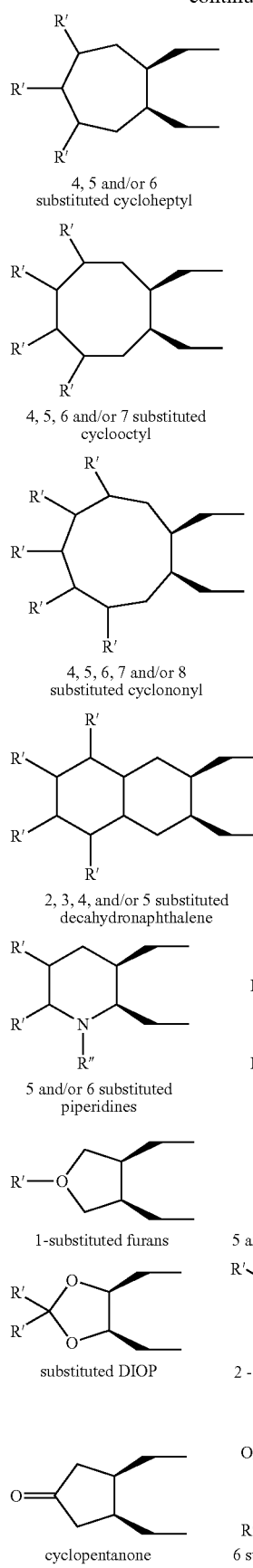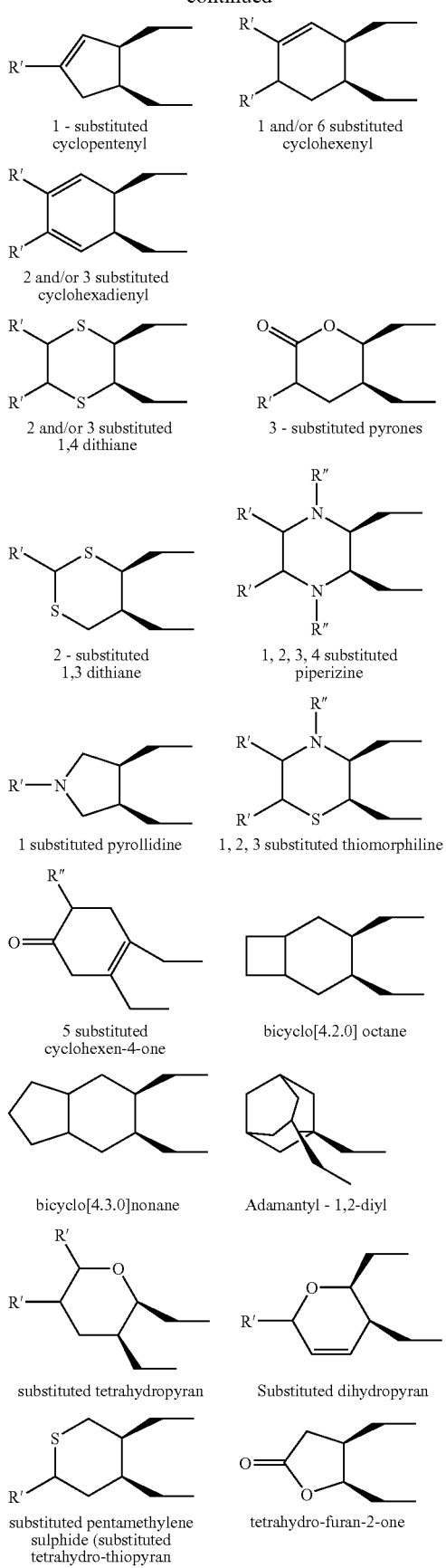

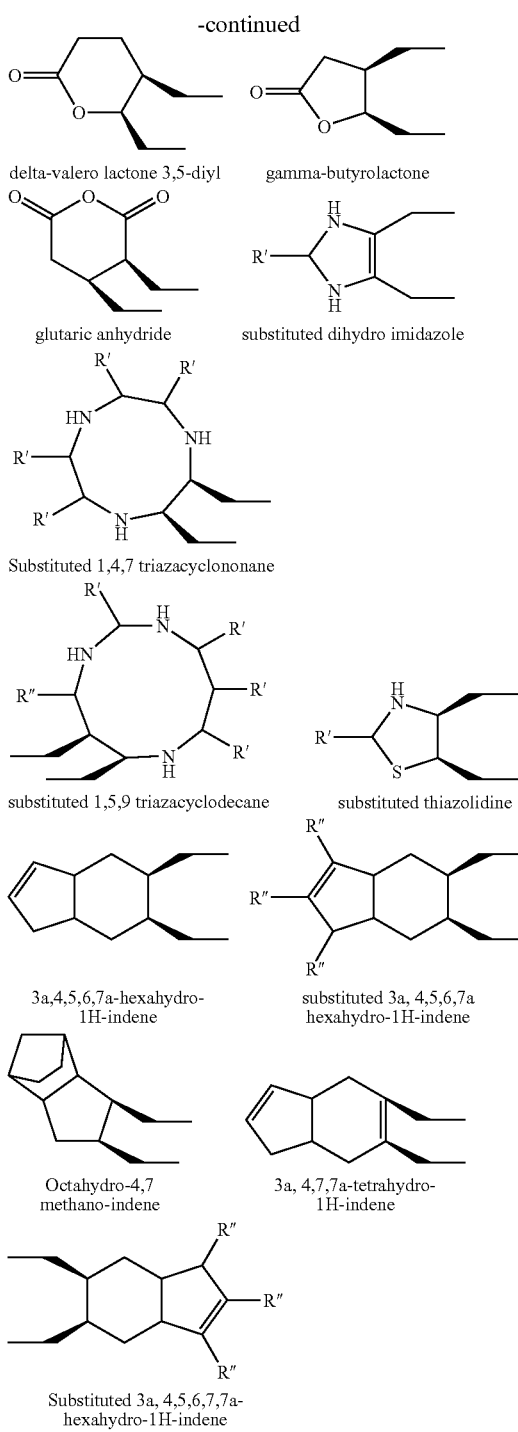

delta-valero lactone 3,5-diyl
gamma-butyrolactone
glutaric anhydride
substituted dihydro imidazole
Substituted 1,4,7 triazacyclononane
substituted 1,5,9 triazacyclodecane
substituted thiazolidine
3a,4,5,6,7a-hexahydro-1H-indene
substituted 3a,4,5,6,7a hexahydro-1H-indene
Octahydro-4,7 methano-indene
3a, 4,7,7a-tetrahydro-1H-indene
Substituted 3a, 4,5,6,7,7a-hexahydro-1H-indene In the structures herein, where there is more than one stereoisomeric form possible, all such stereoisomers are intended. However, it is preferable that the at least one substituent on at least one further non-adjacent cyclic atom of the at least one ring extends in a trans direction with respect to the A and or B atom ie extends outwardly on the opposite side of the ring.

Preferably, the cyclic hydrocarbyl structure is associated with A and B as the cis-1,2-cyclic hydrocarbyl structure or, in any case, cis with respect to the bond between the two available adjacent cyclic atoms to which A and B are respectively attached.

Typically, the group $X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$, wherein $R^1$ to $R^{12}$ represent lower alkyl, aryl or het.

Particularly preferred is when the organic groups $R^1$-$R^3$, $R^4$-$R^6$, $R^7$-$R^9$ and/or $R^{10}$-$R^{12}$ or, alternatively, $R^1$-$R^6$ and/or $R^7$-$R^{12}$ when associated with their respective tertiary carbon atom(s) form composite groups which are at least as sterically hindering as t-butyl(s). Steric hindrance in this context is as discussed at page 14 et seq of "Homogenous Transition Metal Catalysis—A Gentle Art", by C Masters, published by Chapman and Hall 1981. These steric groups may be cyclic, part-cyclic or acyclic. When cyclic or part cyclic, the group may be substituted or unsubstituted or saturated or unsaturated. The cyclic or part cyclic groups may preferably contain, including the tertiary carbon atom(s), from $C_4$-$C_{34}$, more preferably $C_8$-$C_{24}$, most preferably $C_{10}$-$C_{20}$ carbon atoms in the cyclic structure. The cyclic structure may be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, aryl or Het, wherein $R^{19}$ to $R^{30}$ each independently represent hydrogen, aryl or lower alkyl, and/or be interrupted by one or more oxygen or sulphur atoms, or by silano or dialkylsilicon groups.

In particular, when cyclic, $X^1$, $X^2$, $X^3$ and/or $X^4$ may represent congressyl, norbornyl, 1-norbornadienyl or adamantyl, or $X^1$ and $X^2$ together with $Q^2$ to which they are attached form an optionally substituted 2-$Q^2$-tricyclo[3.3.1.1{3,7}] decyl group or derivative thereof, or $X^1$ and $X^2$ together with $Q^2$ to which they are attached form a ring system of formula 1a

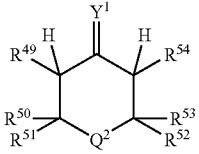

(1a)

Similarly, $X^3$ and $X^4$ together with $Q^1$ to which they are attached may form an optionally substituted 2-Q1-tricyclo [3.3.1.1{3,7}]decyl group or derivative thereof, or $X^3$ and $X^4$ together with $Q^1$ to which they are attached may form a ring system of formula 1b

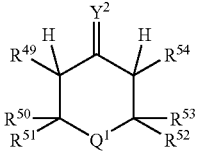

(1b)

Alternatively, one or more of the groups $X^1$, $X^2$, $X^3$ and/or $X^4$ may represent a solid phase to which the ligand is attached.

Particularly preferred is when $X^1$, $X^2$, $X^3$ and $X^4$ or $X^1$ and $X^2$ together with its respective $Q^2$ atom and $X^3$ and $X^4$ together with its respective $Q^1$ atom are the same or when $X^1$ and $X^3$ are the same whilst $X^2$ and $X^4$ are different but the same as each other.

$R^1$ to $R^{12}$ each independently represent hydrogen, lower alkyl, aryl, halo or Het; preferably, lower alkyl, aryl, halo or Het.

$R^{19}$ to $R^{30}$ each independently represent hydrogen, lower alkyl, aryl or Het and may be interrupted by one or more oxygen, sulphur, silicon atoms, or by silano or dialkylsilicon groups or mixtures thereof;

$R^{49}$, $R^{54}$ and $R^{55}$, when present, each independently represent hydrogen, lower alkyl or aryl;

$R^{50}$ to $R^{53}$, when present, each independently represent hydrogen, lower alkyl, aryl or Het;

$Y^1$, $Y^2$, $Y^3$, $Y^4$ and $Y^5$, when present, each independently represent oxygen, sulfur or N—$R^{55}$, wherein $R^{55}$ represents hydrogen, lower alkyl or aryl.

Preferably, $R^1$ to $R^{12}$ each independently represent lower alkyl or aryl. More preferably, $R^1$ to $R^{12}$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as defined herein). Even more preferably, $R^1$ to $R^{12}$ each independently represent $C_1$ to $C_6$ alkyl, which is optionally substituted as defined herein. Most preferably, $R^1$ to $R^{12}$ each represent non-substituted $C_1$ to $C_6$ alkyl such as methyl, ethyl, n-propyl, iso-propyl, n-butyl, iso-butyl, tert-butyl, pentyl, hexyl and cyclohexyl, especially methyl.

In a particularly preferred embodiment of the present invention $R^1$, $R^4$, $R^7$ and $R^{10}$ each represent the same lower alkyl, aryl or Het moiety as defined herein, $R^2$, $R^5$, $R^8$ and $R^{11}$ each represent the same lower alkyl, aryl or Het moiety as defined herein, and $R^3$, $R^6$, $R^9$ and $R^{12}$ each represent the same lower alkyl, aryl or Het moiety as defined herein. More preferably $R^1$, $R^4$, $R^7$ and $R^{10}$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$, $R^8$ and $R^{11}$ each independently represent the same $C_1$-$C_6$ alkyl as defined above; and $R^3$, $R^6$, $R^9$ and $R^{12}$ each independently represent the same $C_1$-$C_6$ alkyl as defined above. For example: $R^1$, $R^4$, $R^7$ and $R^{10}$ each represent methyl; $R^2$, $R^5$, $R^8$ and $R^{11}$ each represent ethyl; and, $R^3$, $R^6$, $R^9$ and $R^{12}$ each represent n-butyl or n-pentyl.

In an especially preferred embodiment of the present invention each $R^1$ to $R^{12}$ group represents the same lower alkyl, aryl, or Het moiety as defined herein. Preferably, when alkyl groups, each $R^1$ to $R^{12}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. More preferably, each $R^1$ to $R^{12}$ represents methyl or tert-butyl, most preferably, methyl.

The term "lower alkylene" which A and B represent in a compound of formula I, when used herein, includes $C_1$ to $C_{10}$ groups which can be bonded at two places on the group to thereby connect the group $Q^1$ or $Q^2$ to the R group, and is otherwise defined in the same way as "lower alkyl" below. Nevertheless, methylene is most preferred.

The term "lower alkyl" when used herein, means $C_1$ to $C_{10}$ alkyl and includes methyl, ethyl, ethenyl, propyl, propenyl butyl, butenyl, pentyl, pentenyl, hexyl, hexenyl and heptyl groups. Unless otherwise specified, alkyl including lower alkyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ each independently represent hydrogen, unsubstituted or substituted aryl or unsubstituted or substituted lower alkyl, and/or be interrupted by one or more (preferably less than 4) oxygen, sulphur, silicon atoms, or by silano or dialkylsilicon groups, or mixtures thereof.

The term "alkenyl" when used herein, means $C_2$ to $C_{10}$ alkenyl and includes ethenyl, propenyl, butenyl, pentenyl, and hexenyl groups.

Unless otherwise specified, alkenyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ each independently represent hydrogen, unsubstituted or substituted aryl or unsubstituted or substituted lower alkyl, and/or be interrupted by one or more (preferably less than 4) oxygen, sulphur, silicon atoms, or by silano or dialkylsilicon groups, or mixtures thereof.

The term "alkynyl" when used herein, means $C_2$ to $C_{10}$ alkynyl and includes ethynyl, propynyl, butynyl, pentynyl, and hexynyl groups.

Unless otherwise specified, alkynyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ each independently represent hydrogen, unsubstituted or substituted aryl or unsubstituted or substituted lower alkyl, and/or be interrupted by one or more (preferably less than 4) oxygen, sulphur, silicon atoms, or by silano or dialkylsilicon groups, or mixtures thereof.

The terms "alkyl", "aralkyl", "alkaryl", "arylenealkyl" or the like should, in the absence of information to the contrary, be taken to be in accordance with the above definition of "lower alkyl" as far as the alkyl or alk portion of the group is concerned.

The term "Ar" or "aryl" when used herein, includes five-to-ten-membered, preferably six to ten membered, carbocyclic aromatic or pseudo aromatic groups, such as phenyl, ferrocenyl and naphthyl, which groups may be unsubstituted or substituted with one or more substituents selected from unsubstituted or substituted aryl, lower alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or lower alkyl (which alkyl group may itself be unsubstituted or substituted or terminated as defined herein).

The above Ar or aryl groups may be attached by one or more covalent bonds but references to arylene or arylenealkyl or the like herein should be understood as two covalent bond attachment but otherwise be defined as Ar or aryl above as far as the arylene portion of the group is concerned. References to alkaryl, aralkyl or the like should be taken as references to Ar or aryl above as far as the Ar or aryl portion of the group is concerned.

Halo groups with which the above-mentioned groups may be substituted or terminated include fluoro, chloro, bromo and iodo.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, lower alkyl (which alkyl group may itself be unsubstituted or substituted or terminated as defined herein) —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, unsubstituted or substituted aryl or lower alkyl (which alkyl group itself may be unsubstituted or substituted or terminated as defined herein). The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term hetero as mentioned herein means nitrogen, oxygen, sulfur or mixtures thereof.

The adamantyl, congressyl, norbornyl or 1-norborndienyl group may optionally comprise, besides hydrogen atoms, one or more substituents selected from lower alkyl, —$OR^{19}$, —$OC(O)R^{20}$, halo, nitro, —$C(O)R^{21}$, —$C(O)OR^{22}$, cyano, aryl, —$N(R^{23})R^{24}$, —$C(O)N(R^{25})R^{26}$, —$C(S)(R^{27})R^{28}$, —$SR^{29}$, —$C(O)SR^{30}$, —$CF_3$, —$P(R^{56})R^{57}$, —$PO(R^{58})(R^{59})$, —$PO_3H_2$, —$PO(OR^{60})(OR^{61})$, or —$SO_3R^{62}$, wherein $R^{19}$-$R^{30}$, lower alkyl, halo, cyano and aryl are as defined herein and $R^{56}$ to $R^{62}$ each independently represent hydrogen, lower alkyl, aryl or Het.

Suitably, when the adamantyl, congressyl, norbornyl or 1-norborndienyl group is substituted with one or more substituents as defined above, highly preferred substituents include unsubstituted $C_1$ to $C_8$ alkyl, —$OR^{19}$, —$OC(O)R^{20}$, phenyl, —$C(O)OR^{22}$, fluoro, —$SO_3H$, —$N(R^{23})R^{24}$, —$P(R^{56})R^{57}$, $C(O)N(R^{25})R^{26}$ and —$PO(R^{58})(R^{59})$, —$CF_3$, wherein $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl, $R^{56}$ to $R^{59}$ each independently represent unsubstituted $C_1$-$C_8$ alkyl or phenyl. In a particularly preferred embodiment the substituents are $C_1$ to $C_8$ alkyl, more preferably, methyl such as found in 1,3 dimethyl adamantyl.

Suitably, the adamantyl, congressyl, norbornyl or 1-norborndienyl group may comprise, besides hydrogen atoms, up to 10 substituents as defined above, preferably up to 5 substituents as defined above, more preferably up to 3 substituents as defined above. Suitably, when the adamantyl, congressyl, norbornyl or 1-norborndienyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl, congressyl, norbornyl or 1-norborndienyl group comprises hydrogen atoms only i.e. the adamantyl, congressyl, norbornyl or 1-norborndienyl group is not substituted.

Preferably, when more than one adamantyl, congressyl, norbornyl or 1-norborndienyl group is present in a compound of formula I, each such group is identical.

The 2-$Q^2$ (or $Q^1$)-tricyclo[3.3.1.1.{3,7}]decyl group (referred to hereinafter as a 2-meta-adamantyl group for convenience wherein 2-meta-adamantyl is a reference to $Q^1$ or $Q^2$ being an arsenic, antimony or phosphorous atom i.e. 2-arsa-adamantyl and/or 2-stiba-adamantyl and/or 2-phospha-adamantyl, preferably, 2-phospha-adamantyl) may optionally comprise, beside hydrogen atoms, one or more substituents. Suitable substituents include those substituents as defined herein in respect of the adamantyl group. Highly preferred substituents include lower alkyl, particularly unsubstituted $C_1$-$C_8$ alkyl, especially methyl, trifluoromethyl, —$OR^{19}$ wherein $R^{19}$ is as defined herein particularly unsubstituted $C_1$-$C_8$ alkyl or aryl, and 4-dodecylphenyl. When the 2-meta-adamantyl group includes more than one substituent, preferably each substituent is identical.

Preferably, the 2-meta-adamantyl group is substituted on one or more of the 1, 3, 5 or 7 positions with a substituent as defined herein. More preferably, the 2-meta-adamantyl group is substituted on each of the 1, 3 and 5 positions. Suitably, such an arrangement means the Q atom of the 2-meta-adamantyl group is bonded to carbon atoms in the adamantyl skeleton having no hydrogen atoms. Most preferably, the 2-meta-adamantyl group is substituted on each of the 1, 3, 5 and 7 positions. When the 2-meta-adamantyl group includes more than 1 substituent preferably each substituent is identical. Especially preferred substituents are unsubstituted $C_1$-$C_8$ alkyl and haloalkyls, particularly unsubstituted $C_1$-$C_8$ alkyl such as methyl and fluorinated $C_1$-$C_8$ alkyl such as trifluoromethyl.

Preferably, 2-meta-adamantyl represents unsubstituted 2-meta-adamantyl or 2-meta-adamantyl substituted with one or more unsubstituted $C_1$-$C_8$ alkyl substituents, or a combination thereof.

Preferably, the 2-meta-adamantyl group includes additional heteroatoms, other than the 2-Q atom, in the 2-meta-adamantyl skeleton. Suitable additional heteroatoms include oxygen and sulphur atoms, especially oxygen atoms. More preferably, the 2-meta-adamantyl group includes one or more additional heteroatoms in the 6, 9 and 10 positions. Even more preferably, the 2-meta-adamantyl group includes an additional heteroatom in each of the 6, 9 and 10 positions. Most preferably, when the 2-meta-adamantyl group includes two or more additional heteroatoms in the 2-meta-adamantyl skeleton, each of the additional heteroatoms are identical. An especially preferred 2-meta-adamantyl group, which may optionally be substituted with one or more substituents as defined herein, includes an oxygen atom in each of the 6, 9 and 10 positions of the 2-meta-adamantyl skeleton.

Preferably, the 2-meta-adamantyl includes one or more oxygen atoms in the 2-meta-adamantyl skeleton.

Highly preferred 2-meta-adamantyl groups as defined herein include 2-phospha-1,3,5,7-tetramethyl-6,9,10-trioxadamantyl, 2-phospha-1,3,5-trimethyl-6,9,10-trioxadamantyl, 2-phospha-1,3,5,7-tetra(trifluoromethyl)-6,9,10-trioxadamantyl group, and 2-phospha-1,3,5-tri(trifluoromethyl)-6,9,10-trioxadamantyl group. Most preferably, the 2-phospha-adamantyl is selected from 2-phospha-1,3,5,7-tetramethyl-6,9,10-trioxadamantyl group or 2-phospha-1,3,5,-trimethyl-6,9,10-trioxadamantyl group.

Preferably, when more than one 2-meta-adamantyl group is present in a compound of formula I, each 2-meta-adamantyl group is identical.

The 2-meta-adamantyl group may be prepared by methods well known to those skilled in the art. Suitably, certain 2-phospha-adamantyl compounds are obtainable from Cytec Canada Inc, Canada. Likewise corresponding 2-meta-adamantyl compounds of formula I etc may be obtained from the same supplier or prepared by analogous methods.

Preferred embodiments of the present invention include those wherein:

$X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;

$X^3$ represents $CR^7(R^8)(R^9)$, $X^4$ represents $CR^{10}(R^{11})(R^{12})$, and $X^1$ and $X^2$ together with $Q^2$ to which they are attached form a 2-phospha-adamantyl group;

$X^3$ represents $CR^7(R^8)(R^9)$, $X^4$ represents $CR^{10}(R^{11})(R^{12})$; and $X^1$ and $X^2$ together with $Q^2$ to which they are attached form a ring system of formula 1a;

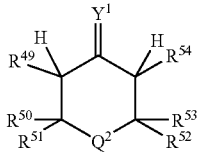

(1a)

$X^3$ represents $CR^7(R^8)(R^9)$, $X^4$ represents adamantyl, and $X^1$ and $X^2$ together with $Q^2$ to which they are attached form a 2-phospha-adamantyl group;

$X^3$ represents $CR^7(R^8)(R^9)$, $X^4$ represents adamantyl and $X^1$ and $X^2$ together with $Q^2$ to which they are attached form a ring system of formula 1a;

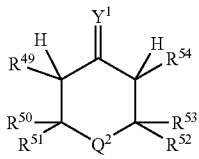

(1a)

$X^3$ represents $CR^7(R^8)(R^9)$, $X^4$ represents adamantyl, $X^1$ represents $CR^1(R^2)(R^3)$ and $X^2$ represents $CR^4(R^5)(R^6)$;

$X^3$ represents $CR^7(R^8)(R^9)$, $X^4$ represents congressyl, and $X^1$ and $X^2$ together with $Q^2$ to which they are attached form a 2-phospha-adamantyl group;

$X^3$ represents $CR^7(R^8)(R^9)$, $X^4$ represents congressyl, $X^1$ represents $CR^1(R^2)(R^3)$ and $X^2$ represents $CR^4(R^5)(R^6)$;

$X^3$ and $X^4$ independently represent adamantyl, and $X^1$ and $X^2$ together with $Q^2$ to which they are attached form a 2-phospha-adamantyl group;

$X^3$ and $X^4$ independently represent adamantyl, and $X^1$ and $X^2$ together with $Q^2$ to which they are attached form a ring system of formula 1a;

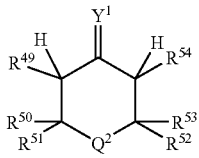

(1a)

$X^3$ and $X^4$ independently represent adamantyl, $X^1$ represents $CR^1(R^2)(R^3)$ and $X^2$ represents $CR^4(R^5)(R^6)$;

$X^1$, $X^2$, $X^3$ and $X^4$ represent adamantyl;

$X^3$ and $X^4$ together with $Q^1$ to which they are attached may form a ring system of formula 1b

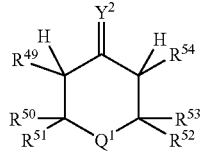

(1b)

and $X^1$ and $X^2$ together with $Q^2$ to which they are attached form a ring system of formula 1a;

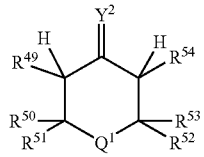

(1a)

$X^3$ and $X^4$ independently represent congressyl, and $X^1$ and $X^2$ together with $Q^2$ to which they are attached form a 2-phospha-adamantyl group;

$X^3$ and $X^4$ together with $Q^1$ to which they are attached may form a ring system of formula 1b

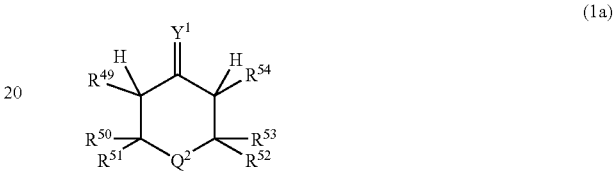

(1b)

and $X^1$ and $X^2$ together with $Q^2$, to which they are attached form a 2-phospha-adamantyl group;

$X^3$ and $X^4$ independently represent congressyl, and $X^1$ represents $CR^1(R^2)(R^3)$ and $X^2$ represents $CR^4(R^5)(R^6)$;

$X^3$ and $X^4$ together with $Q^1$ to which they are attached may form a ring system of formula 1b (1b)

$X^1$ represents $CR^1(R^2)(R^3)$ and $X^2$ represents $CR^4(R^5)(R^6)$;

$X^3$ and $X^4$ together with $Q^1$ to which they are attached form a 2-phospha-adamantyl group, and $X^1$ and $X^2$ together with $Q^2$ to which they are attached form a 2-phospha-adamantyl group Highly preferred embodiments of the present invention include those wherein:

$X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$; especially where $R^1$-$R^{12}$ are methyl.

Preferably in a compound of formula I, $X^3$ is identical to $X^4$ and/or $X^1$ is identical to $X^2$.

Particularly preferred combinations in the present invention include those wherein:—

(1) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;
A and B are the same and represent —$CH_2$—;
$Q^1$ and $Q^2$ both represent phosphorus linked to the R group at ring positions 1 and 2;
R represents 1,2 cis-5,6-dimethyl cyclohexyl.

(2) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;
A and B are the same and represent —$CH_2$—;
$Q^1$ and $Q^2$ both represent phosphorus linked to the R group at ring positions 1 and 2;
R represents 1,2-cis-5-methyl cyclopentyl.

(3) $X^3$ and $X^4$ together with $Q^1$ to which they are attached form a 2-phospha-adamantyl group, and, $X^1$ and $X^2$ together with $Q^2$ to which they are attached form a 2-phospha-adamantyl group;
A and B are the same and represent —$CH_2$—;
$Q^1$ and $Q^2$ both represent phosphorus linked to the R group at ring positions 1 and 2;
R represents 1,2 cis-5,6-dimethyl cyclohexyl.

(4) $X^1$, $X^2$, $X^3$ and $X^4$ represent adamantyl;
A and B are the same and represent —$CH_2$—;
$Q^1$ and $Q^2$ both represent phosphorus linked to the R group at ring positions 1 and 2;
R represents 1,2 cis-5,6-dimethyl cyclohexyl.

Preferably, in the compound of formula I, A and B each independently represents $C_1$ to $C_6$ alkylene which is optionally substituted as defined herein, for example with lower alkyl groups. Preferably, the lower alkylene groups which A and B represent are non-substituted. Particularly preferred lower alkylene which A and B may independently represent are —$CH_2$— or —$C_2H_4$—. Most preferably, each of A and B represent the same lower alkylene as defined herein, particularly —$CH_2$—.

Still further preferred compounds of formula I include those wherein:
$R^1$ to $R^{12}$ are alkyl and are the same and preferably, each represents $C_1$ to $C_6$ alkyl, particularly methyl.

Especially preferred specific compounds of formula I include those wherein:
each $R^1$ to $R^{12}$ is the same and represents methyl;
A and B are the same and represent —$CH_2$—;
R represents 4,5 dimethyl-cis-1,2-cyclohexyl.

Examples of suitable bidentate ligands are cis-1,2-bis(di-t-butylphosphinomethyl)-4,5-dimethyl cyclohexane; cis-1,2-bis(di-t-butylphosphinomethyl)-5-methylcyclopentane; cis-1,2-bis(2-phosphinomethyl-1,3,5,7-tetramethyl-6,9,10-trioxa-adamantyl)-4,5-dimethylcyclohexane; cis-1,2-bis(2-phosphinomethyl-1,3,5,7-tetramethyl-6,9,10-trioxa-adamantyl) 5-methylcyclopentane; cis-1,2-bis(di-adamantylphosphinomethyl)-4,5 dimethylcyclohexane; cis-1,2-bis(di-adamantylphosphinomethyl)-5-methyl cyclopentane; cis-1-(P,P adamantyl, t-butyl phosphinomethyl)-2-(di-t-butylphosphinomethyl)-4,5-dimethylcyclohexane; cis-1-(PP adamantyl, t-butyl phosphinomethyl)-2-(di-t-butylphosphinomethyl)-5-methylcyclopentane; cis-1-(2-phosphinomethyl-1,3,5,7-tetramethyl-6,9,10-trioxa-adamantyl)-2-(di-t-butylphosphinomethyl)4,5-dimethylcyclohexane; cis-1-(2-phosphinomethyl-1,3,5,7-tetramethyl-6,9,10-trioxa-adamantyl)-2-(di-t-butylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)-5-methyl cyclohexane; cis-1-(2-phosphinomethyl-1,3,5,7-tetramethyl-6,9,10-trioxa-adamantyl)-2-(diadamantylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)-4,5-dimethyl cyclohexane; cis-1-(di-t-butylphosphinomethyl)-2-(diadamantylphosphinomethyl)-5-methyl cyclopentane; cis-1,2-bis(2-phosphinomethyl-1,3,5-trimethyl-6,9,10-trioxatricyclo-{3.3.1.1[3.7]}decyl)-4,5-dimethyl cyclohexane; cis-1,2-bis(2-phosphinomethyl-1,3,5-trimethyl-6,9,10-trioxatricyclo-{3.3.1.1[3.7]}decyl)-5-methyl cyclopentane; cis-1-(2-phosphinomethyl-1,3,5-trimethyl-6,9,10-trioxatricyclo-{3.3.1.1[3.7]}decyl)-2-di-t-butylphosphinomethyl)-4,5-dimethyl cyclohexane; cis-1-(2-phosphinomethyl-1,3,5-trimethyl-6,9,10-trioxatricyclo-{3.3.1.1[3.7]}decyl)-2-(di-t-butylphosphinomethyl)-5-methyl cyclopentane; cis-1-(2-phosphinomethyl-1,3,5-trimethyl-6,9,10-trioxatricyclo-{3.3.1.1[3.7]}decyl)-2-(diadamantylphosphinomethyl)-4,5-dimethyl cyclohexane; cis-1-(2-phosphinomethyl-1,3,5-trimethyl-6,9,10-trioxatricyclo-{3.3.1.1[3.7]}decyl)-2-(diadamantylphosphinomethyl)-5-methyl cyclopentane; cis-1,2-bis-perfluoro(2-phosphinomethyl-1,3,5,7-tetramethyl-6,9,10-trioxatricyclo {3.3.1.1[3.7]}-decyl)-4,5-dimethyl cyclohexane; cis-1,2-bis-perfluoro(2-phosphinomethyl-1,3,5,7-tetramethyl-6,9,10-trioxatricyclo {3.3.1.1[3.7]}decyl)-5-methyl cyclopentane; cis-1,2-bis-(2-phosphinomethyl-1,3,5,7-tetra(trifluoro-methyl)-6,9,10-trioxatricyclo {3.3.1.1[3.7]}decyl)-4,5-dimethyl cyclohexane; cis-1,2-bis-(2-phosphinomethyl-1,3,5,7-tetra(trifluoro-methyl)-6,9,10-trioxatricyclo {3.3.1.1[3.7]}decyl)-5-methyl cyclopentane; and including all cis enantiomers of the foregoing where such enantiomers are possible.

Examples of substituted ligands include:—

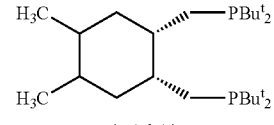

cis-1,2-bis
(di-tert-butylphosphinomethyl),
4,5 dimethylcyclohexane

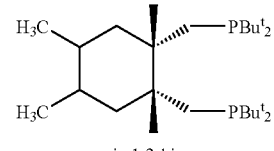

cis-1,2-bis
(di-tert-butylphosphinomethyl),
1,2,4,5 tetramethylcyclohexane

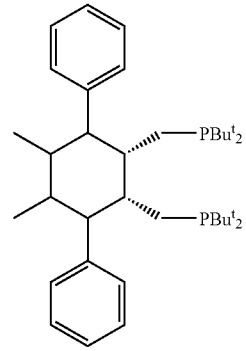

cis-1,2-bis
(di-tert-butylphosphinomethyl),
3,6,diphenyl-4,5 dimethyl-
cyclohexane

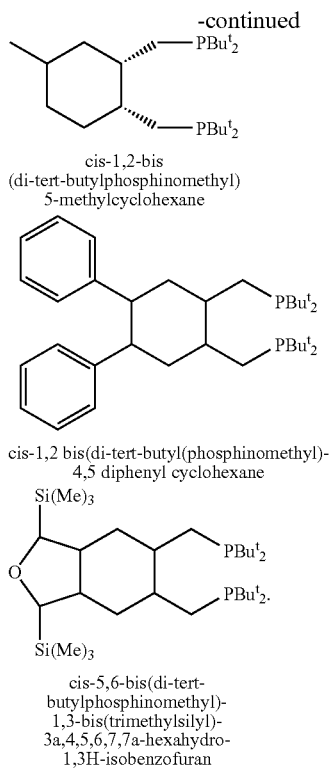

cis-1,2-bis
(di-tert-butylphosphinomethyl)
5-methylcyclohexane cis-1,2 bis(di-tert-butyl(phosphinomethyl)-
4,5 diphenyl cyclohexane cis-5,6-bis(di-tert-
butylphosphinomethyl)-
1,3-bis(trimethylsilyl)-
3a,4,5,6,7,7a-hexahydro-
1,3H-isobenzofuran Preferably, $Q^2$ is phosphorous and preferably, $Q^1$ is independently, phosphorous.

Preferably, the bidentate ligand is a bidentate phosphine, arsine or stibine ligand, preferably, a phosphine ligand.

Suitable Group 8, 9 or 10 metals or a compound thereof which may be combined with compound of formula (I) or (V) include cobalt, nickel, palladium, rhodium and platinum. Preferably, the Group 8, 9 or 10 metal is palladium or a compound thereof. Suitable compounds of such Group 8, 9 or 10 metals include salts of such metals with, or compounds comprising weakly coordinated anions derived from, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins (including low acid level sulphonic resins) perhalic acid such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids. Other sources which may provide suitable anions include the optionally halogenated tetraphenyl borate derivatives, e.g. perfluorotetraphenyl borate. Additionally, zero valent palladium complexes particularly those with labile ligands, e.g. triphenylphosphine or alkenes such as dibenzylideneacetone or styrene or tri(dibenzylideneacetone)dipalladium may be used.

In an alkoxycarbonylation reaction, the anion may be derived from or introduced as one or more of an acid having a pKa measured in aqueous solution at 18° C. of less than 4, more preferably, less than 3, a salt with a cation that does not interfere with the reaction, e.g. metal salts or largely organic salts such as alkyl ammonium, and a precursor, such as an ester, that can break down under reaction conditions to generate the anion in situ. Suitable acids and salts include the acids and salts, other than unsubstituted carboxylates, listed supra In an hydroxycarbonylation reaction, the anion may be derived from or introduced as one or more of an acid having a pKa measured in aqueous solution at 18° C. of less than 6, more preferably, less than 5, a salt with a cation that does not interfere with the reaction, e.g. metal salts or largely organic salts such as alkyl ammonium, and a precursor, such as an ester, that can break down under reaction conditions to generate the anion in situ. Suitable acids and salts include the acids and salts listed supra.

In one particular preferred embodiment, the anion in the hydroxycarbonylation reaction may be derived from a carboxylic acid. The carboxylic acid is preferably any optionally substituted $C_1$-$C_{30}$ organic compound having at least one carboxylic acid group, more preferably any C1 to C16 organic compound having at least one carboxylic acid group. The pKa of the acid is preferably greater than about 2 measured in an aqueous solution at 18° C. The pKa is preferably less than about 5.0 measured in an aqueous solution at 18° C. The organic compound may be substituted with one or more of the following: hydroxy groups, $C_1$-$C_4$ alkoxy groups such as, for example, methoxy; amine or halogenide groups such as, for example Cl, I and Br. Examples of suitable carboxylic acids include but are not restricted to benzoic acid, substituted benzoic acids, acetic acid, propionic acid, valeric acid, butanoic acid cyclohexylpropionic acid or nonanoic acid.

Examples of suitable sterically hindered carboxylic acids which may be used in the hydroxycarbonylation reaction include but are not restricted to sterically hindered benzoic acids, including, for example, $C_1$-$C_4$ alkyl substituted benzoic acids such as for example, 2,6-dimethylbenzoic acid or 2,4,6-trimethyl benzoic acid. These also include hydroxy substituted benzoic acids such as, for example, meta- and parahydroxybenzoic acid and other substituted benzoic acids such as, for example, 2,6-fluorobenzoic acid or 2,4,6-tribromobenzoic acid.

Particularly preferred acid promoters for an alkoxycarbonylation are the sulfonic acids and sulfonated ion exchange resins listed supra. The low level acid ion exchange resins that may be used preferably provide a level of $SO_3H$/Pd ratio in the reaction of less than 35 mol/mol, more preferably less than 25 mol/mol, most preferably less than 15 mol/mol. Typical ranges for the $SO_3H$ concentration provided by the resin are in the range 1-40 mol/mol Pd, more typically, 2-30 mol/mol Pd, most typically 3-20 mol/mol Pd.

Preferably, in an hydroxycarbonylation reaction, the solvent may be an acid having a pKa less than 5, more preferably, having a pKa greater than 3 and less than 5. Suitable acid solvents may be selected from the acids listed supra, more preferably, the lower alkanoic (up to $C_{12}$) acids such as acetic and propanoic, most preferably acetic acid.

In an alkoxycarbonylation reaction, the quantity of anion present is not critical to the catalytic behaviour of the catalyst system. The molar ratio of anion to Group 8, 9 or 10 metal or compound may be from 1:1 to 500:1, preferably from 2:1 to 100:1 and particularly from 3:1 to 30:1. Where the anion is provided by an acid and salt, the relative proportion of the acid and salt is not critical. However, where an anion is provided by acid or partially provided by acid the ratio of acid to group 8, 9 or 10 metal is preferably, at least 1:1 mol ($H^+$)/mol ($C^{2+}$) and preferably, less than at least 5:1 mol ($H^+$)/mol ($C^{2+}$), more preferably, the ratio is at least 2:1 and preferably, less than at least 3:1; most preferably, around a 2:1 ratio is preferred. By $H^+$ is meant the amount of active acidic sites so that a mole of monobasic acid would have 1 mole of H⁺ whereas a mole of dibasic acid would have 2 moles of H⁺ and tribasic acids etc should be interpreted accordingly. Similarly, by $C^{2+}$ is meant moles of metal having a 2⁺ cationic charge so that for M⁺ ions the ratio of the metal cation should be adjusted accordingly. For example, an M⁺ cation should be taken as having 0.5 moles of $C^{2+}$ per mole of M⁺.

In an hydroxycarbonylation reaction, the quantity of anion present is not critical to the catalytic behaviour of the catalyst system. The molar ratio of anion to Group 8, 9 or 10 metal/compound may be from 1:1 to 10000:1, preferably from 2:1 to 1000:1 and particularly from 3:1 to 100:1. Where the anion is provided by an acid and salt, the relative proportion of the acid and salt is not critical.

In an alkoxycarbonylation reaction, preferably, the ratio of bidentate ligand to acid is at least 1:2 mol/mol (H⁺) and preferably, the ratio of bidentate ligand to group 8, 9 or 10 metal is at least 1:1 mol/mol ($C^{2+}$). Preferably, the ligand is in excess of metal mol/mol ($C^{2+}$) and preferably in excess of a ratio of 1:2 mol/mol (H⁺) with the acid. Excess ligand is advantageous as the ligand itself may act as a base to buffer the acid levels in the reaction and prevent degradation of substrate. On the other hand the presence of acid activates the reaction mix and improves the overall rate of reaction.

In an hydroxycarbonylation reaction, preferably, the ratio of bidentate ligand to acid is at least 1:2 mol/mol (H⁺) and preferably, the ratio of bidentate ligand to group 8, 9 or 10 metal is at least 1:1 mol/mol ($C^{2+}$). Preferably, the ligand is in excess of metal mol/mol ($C^{2+}$). Excess ligand may be advantageous as the ligand itself may act as a base to buffer the acid levels in the reaction and prevent degradation of substrate. On the other hand the presence of acid activates the reaction mix and improves the overall rate of reaction.

As mentioned, the catalyst system of the present invention may be used homogeneously or heterogeneously. Preferably, the catalyst system is used homogeneously.

As mentioned above, where appropriate to the substrate, the process of the invention is particularly efficacious for the production of linear product.

Therefore, the invention also relates specifically to the carbonylation of an unsaturated ester, specifically vinyl ester and, in particular but not exclusively, the use of the carbonylation to provide a first step in the production of methyl lactate and 3-hydroxymethyl propanoate or 3-hydroxy propionic acid.

Currently methyl lactate is produced by esterification of lactic acid, which is produced either by synthetic methods or fermentation.

The main synthetic routes are based on the reactions of acetaldehyde. In one method, acetaldehyde is reacted with hydrogen cyanide to produce a lactonitrile, which is then hydrolysed. Alternatively, acetaldehyde can be reacted with carbon monoxide and water in the presence of a nickel (II) iodide or sulphuric acid catalyst. Synthetic routes produce racemic mixtures of lactic acid, and so racemic mixtures of methyl lactate result. In recent years, improvements in fermentation methods have made this a preferred route to lactic acid and its derivatives. Optically pure lactic acid can be produced by the fermentation of sugars with carefully chosen bacteria. Lactobacilli tend to be heat resistant, so fermentation at temperatures of around 50° C. suppresses secondary reactions. The procedure is slow, and requires careful monitoring of pH, temperature and oxygen levels, but by selecting an appropriate bacteria culture, optically pure lactic acid, of both R and S forms can be produced.

Methyl lactate is used as a high boiling point solvent, and is present in a variety of materials such as detergents, degreasing agents, cosmetics and food flavourings. It is biodegradable, and so environmentally friendly.

A route to 1,3-propanediol would be industrially favourable. Existing routes include the hydroformylation of ethylene oxide with syngas followed by hydrogenation; and the fermentation of corn sugar. In the 1980s, Davy Process Technology found a route to 1,4-butanediol, by forming diethyl maleate from butanes over a solid acid catalyst, and then dehydrogenating it to the diol. 1,4-butanediol is now widely used as a polymer component and also in fibre production and as a high boiling solvent. Polyhydric alcohols are often used in reactions with isocyanates to produce urethanes, and in reactions with acids and acid anhydrides to produce (poly) esters. 1,3-propanediol is thought to have uses as a polymer component and as a high boiling point solvent.

Vinyl esters are known to hydrolyse easily into the corresponding acid or aldehyde. Accordingly, exposure of vinyl ester to acid should be avoided. Hydroxy- or alkoxycarbonylation reactions with bidentate phosphines may proceed in the presence of Group 6, 8, 9 or 10 metals but such metals are generally utilised in the presence of a source of anions derived from acids, for example, having a pKa of less than 5. Accordingly, hydroxy- or alkoxycarbonylation would be deemed unsuitable for carbonylation of vinyl ester due to acid degradation of the latter in the presence of such acids.

According to a still further aspect of the present invention there is provided a process for the carbonylation of a vinyl ester comprising reacting a vinyl ester with carbon monoxide in the presence of a source of hydroxyl groups and of a catalyst system, the catalyst system obtainable by combining:
(a) a metal of Group 8, 9 or 10 or a compound thereof: and
(b) a bidentate ligand of general formula (V)

$$X^1(X^2)\text{-}Q^2\text{-}A\text{-}R\text{—}B\text{-}Q^1\text{-}X^3(X^4) \quad (V)$$

wherein:
A and B each independently represent lower alkylene;
R represents an optionally substituted cycloalkyl moiety to which the $Q^1$ and $Q^2$ atoms are linked on available adjacent cyclic carbon atoms;
the groups $X^1$, $X^2$, $X^3$ and $X^4$ independently represent univalent radicals up to 30 atoms having at least one tertiary carbon atom or $X^1$ and $X^2$ and/or $X^3$ and $X^4$ together form a bivalent radical of up to 40 atoms having at least two tertiary carbon atoms wherein each said univalent or bivalent radical is joined via said at least one or two tertiary carbon atoms respectively to the appropriate atom $Q^1$ or $Q^2$; and
$Q^1$ and $Q^2$ each independently represent phosphorous, arsenic or antimony.

In the above formula (V) unless indicated otherwise, the groups $X^1$, $X^2$, $X^3$ and $X^4$; A and B; and $Q^1$ or $Q^2$ are as already defined herein.

Accordingly, in a second aspect of the present invention there is provided a process for the production of 3-hydroxy propanoate ester or acid of formula (II)

$$CH_2(OH)CH_2C(O)OR^{31} \quad (II)$$

comprising the steps of:
carbonylating vinyl acetate with carbon monoxide in the presence of a source of hydroxyl groups and a catalyst system, the catalyst system obtainable by combining:
(a) a metal of Group 8, 9 or 10 or a compound thereof: and
(b) a bidentate ligand of general formula (I) or (V) as defined herein
wherein $R^{31}$ is selected from H, or a $C_1$-$C_{30}$ alkyl or aryl moiety which may be substituted or unsubstituted and either branched or linear and carrying out a treatment step on the said linear (n) product 1-acyloxy CH$_2$.CH$_2$C(O)OR$^{31}$ to produce the 3-hydroxy propanoate ester or acid of formula (II).

The linear (n) and branched (iso) products of the carbonylation may be separated either before or after the treatment step. Preferably, the said products are separated from the reaction products by distillation.

According to a third aspect of the present invention there is provided the use of the catalyst system as defined in any of the aspects of the present invention for the production, preferably industrial product, of a 3-hydroxy propanoate ester of formula (II) the said production comprising the steps of carbonylation of a vinyl ester followed by treatment of the linear (n) product of the carbonylation.

Despite the foregoing, the invention does not exclude the possibility of utilising the branched product of the reaction.

Therefore, according to a fourth aspect of the present invention there is provided a process for the production of a lactate ester or acid of formula III

(III)

comprising the steps of carbonylating vinyl ester with carbon monoxide in the presence of a source of hydroxyl groups and a catalyst system, the catalyst system obtainable by combining:
(a) a metal of Group 8, 9 or 10 or a compound thereof: and
(b) a bidentate ligand, preferably phosphine ligand, of general formula (I) or (V) as defined herein
to produce a product comprising a branched (iso) product 2-acyloxy (CH$_3$). CH.C(O)OR$^{31}$, wherein R$^{31}$ is selected from H, or a C$_1$-C$_{30}$ alkyl or aryl moiety which may be substituted or unsubstituted and either branched or linear and treatment of the said branched (iso) product to produce the corresponding lactate or acid of formula III.

By treating or treatment herein is meant carrying out routine chemical treatment such as hydrolysis or transesterification reactions on the acyloxy product of the carbonylation suitable to cleave the acyloxy group to produce the hydroxy acid or ester.

The linear (n) and branched (iso) products of the carbonylation may be separated either before or after the treatment step. Preferably, the products of the reaction are separated by distillation. The branched and linear products often have widely differing boiling points which makes distillation an effective separation technique for the products of the reaction.

Preferably, the ratio of linear:branched product from the carbonylation process is greater than 0.5:1, more preferably, greater than 0.9:1, more preferably, greater than 1:1, more preferably, greater than 1.5:1, more preferably, greater than 2:1, most preferably greater than 2.5:1.

According to a fifth aspect of the present invention there is provided the use of the catalyst system as defined in any of the aspects of the present invention for the production, preferably, industrial production, of a lactate ester or acid of formula (III)
the said production comprising the steps of carbonylation of a vinyl ester followed by treatment of the branched (iso) product of the carbonylation to produce the ester or acid.

Advantageously, the lactate or 3-hydroxy propanoate esters or acids of the present invention may be hydrogenated to produce the 1,2 and 1,3 diols respectively.

By acyloxy is meant the group R$^{32}$—C(O)O— as will be hereinafter defined with respect to formula (IV)

Preferably, the treatment as mentioned above is hydrolysis or transesterification and is carried out by any suitable technique known to those skilled in the art. Such techniques are detailed in for example—"Kirkothmer Encyclopaedia of Chemical Technology", volume 9, 4$^{th}$ edition page 783—"Hydrolysis of Organic Esters". Such methods include base hydrolysis, acid hydrolysis, steam hydrolysis and enzymic hydrolysis. Preferably, the hydrolysis is base hydrolysis, more preferably, the hydrolysis is carried out in excess base and then acidified to produce the acid product. Hydrogenation of the hydrolysis product may be carried out by any suitable process known to those skilled in the art. Preferably, vapour phase hydrogenation of the hydroxy alkanoate ester is carried out. A suitable technique has been exemplified in WO 01/70659 by Crabtree et al. Suitable experimental details are set out in examples 1-9 of the published application and illustrate the route to 1,3 propanediol from 3-hydroxy propanoic acid esters. Preferably, the hydrogenation is carried out in a hydrogenation zone containing a heterogenous hydrogenation catalyst. Suitable conditions and catalysts are set out in WO 01/70659, the contents of which are incorporated herein by reference insofar as they relate to the hydrogenation of 3-hydroxy propanoic acid esters. However, for the purposes of the present application such hydrogenation reactions are also deemed applicable to hydrogenation of the lactate ester to produce 1,2 propane diol. Preferably, the transesterification is carried out with the alkanol corresponding to the alkyl group of the alkyl ester product required for example methanol for converting acyloxy alkyl esters into hydroxy methyl esters and ethanol for converting acyloxy alkyl esters into hydroxy ethyl esters etc. Advantageously, this cleaves the acyloxy group but does not alter the hydroxy alkyl alkanoate. Preferably, the transesterification takes place in the presence of a suitable catalyst such as for example methane sulphonic acid or p-toluene sulphonic acid.

For ease of reference, any one or more of the aspects of the invention may be referred to herein as the process of the invention.

It has also been found that the acid counterparts to the vinyl ester by-products of the present invention may be used as the source of anions in the hydroxycarbonylation reaction. The use of such acids is advantageous because they are readily obtainable by hydrolysis of the ester by-products. Examples of such acid hydrolysis products include but are not restricted to acetic acid, propionic acid, butyric acid, benzoic acid, methacrylic acid and crotonic acid. These acids may be derived from the hydrolysis of the corresponding vinyl esters and the hydrolysis of the carbonylation products eg. Vinyl acetate, vinyl propionate, vinyl butyrate, vinyl benzoate, vinyl methacrylate and vinyl crotonate.

Suitably, the process of the invention may be used to catalyse the carbonylation of ethylenically unsaturated compounds such as a vinyl ester or ethylene in the presence of carbon monoxide and a hydroxyl group containing compound eg. the process of the invention may catalyse the conversion of a vinyl ester to the corresponding acyloxy carboxylic ester. Conveniently, the process of the invention may utilise highly stable compounds under typical carbonylation reaction conditions such that they require little or no replenishment. Conveniently, the process of the invention may have a high rate for the carbonylation reaction of an ethylenically unsaturated compound such as ethylene or a vinyl ester. Conveniently, the process of the invention may promote high conversion rates of the ethylenically unsaturated compound such as ethylene or a vinyl ester, thereby yielding the desired product in high yield with little or no impurities. Consequently, the commercial viability of a carbonylation process, such as the carbonylation of ethylene or a vinyl ester, may be increased by employing the process of the invention.

Suitable ethylenically unsaturated compounds for the non-ethylenically specific aspects of the invention are ethylenically unsaturated compounds having from 2 to 50 carbon atoms per molecule, or mixtures thereof. Suitable ethylenically unsaturated compounds may have one or more isolated or conjugated unsaturated bonds per molecule Preferred are compounds having from 2 to 20 carbon atoms, or mixtures thereof, yet more preferred are compounds having at most 18 carbon atoms, yet more at most 16 carbon atoms, again more preferred compounds have at most 10 carbon atoms. The ethylenically unsaturated compound may further comprise functional groups or heteroatoms, such as nitrogen, sulphur or oxide. Examples include carboxylic acids, esters or nitriles as functional groups. In a preferred embodiment, the ethylenically unsaturated compound is an olefin or a mixture of olefins. Such olefins can be converted by reaction with carbon monoxide and a co-reactant with a high regioselectivity, where appropriate, towards the linear carbonylation product. Suitable ethylenically unsaturated compounds include acetylene, methyl acetylene, propyl acetylene, butadiene, ethylene, propylene, butylene, isobutylene, pentene, pentene nitrites, alkyl pentenoates such as methyl 3-pentenoates, pentene acids (such as 2- and 3-pentenoic acid), vinyl acetate, octenes.

Particularly preferred ethylenically unsaturated compounds are ethylene, vinyl acetate, butadiene, alkyl pentenoates, pentenenitriles, pentene acids (such as 3 pentenoic acid), acetylene and propylene.

Especially preferred are ethylene, vinyl acetate, butadiene and pentene nitrites.

References to vinyl ester herein include references to substituted or unsubstituted vinyl ester of formula (IV):

$R^{32}—C(O)OCR^{33}=CR^{34}R^{35}$ wherein $R^{32}$ may be selected from hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{27}R^{28}$, $SR^{29}$, $C(O)SR^{30}$ wherein $R^{19}$-$R^{30}$ are as defined herein.

Preferably, $R^{32}$ is selected from hydrogen, lower alkyl, phenyl or lower allylphenyl, more preferably, hydrogen, phenyl, $C_1$-$C_6$ alkylphenyl or $C_1$-$C_6$ alkyl, such as methyl, ethyl, propyl, butyl, pentyl and hexyl, even more preferably, $C_1$-$C_6$ alkyl, especially methyl.

Preferably, $R^{33}$-$R^{35}$ each independently represents hydrogen, lower alkyl, aryl or Het as defined herein. Most preferably, $R^{33}$-$R^{35}$ independently represents hydrogen.

As mentioned above, $R^{31}$ may be optionally substituted, preferably, with one or more substituents selected from lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{27}R^{28}$, $SR^{29}$ or $C(O)SR^{30}$ as defined herein.

$R^{31}$ is most preferably the H radical derived from water or the alkyl/aryl group derived from a $C_1$-$C_8$ alkanol such as methanol, ethanol, propanol, iso-propanol, iso-butanol, t-butyl alcohol, n-butanol, phenol and chlorocapryl alcohol. The most preferred groups are H, methyl and ethyl, the most especially preferred group is hydrogen.

Preferably, $R^{31}$ represents hydrogen, lower alkyl or aryl. More preferably, $R^{31}$ represents hydrogen, $C_1$ to $C_6$ alkyl, $C_1$-$C_6$ alkyl phenyl (wherein the phenyl group is optionally substituted as defined herein) or phenyl (wherein the phenyl group is optionally substituted as defined herein). Even more preferably, $R^{31}$ represents hydrogen, $C_1$ to $C_6$ alkyl, which is optionally substituted as defined herein. Most preferably, $R^{31}$ represents hydrogen or non-substituted $C_1$ to $C_6$ alkyl such as methyl, ethyl, n-propyl, iso-propyl, n-butyl, iso-butyl, tert-butyl, pentyl, hexyl and cyclohexyl, especially hydrogen or methyl, most especially hydrogen.

Where a compound of a formula herein (e.g. formulas I-IV) contains an alkenyl group or a cycloalkyl moiety as defined, cis (E) and trans (Z) isomerism may also occur. However, the cycloalkyl moiety R when associated with the A and B groups is preferably a cis (E) isomer. The present invention includes the individual stereoisomers of the compounds of any of the formulas defined herein and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound one of the formulas or a suitable salt or derivative thereof. An individual enantiomer of a compound of one of the formulas may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the process of the invention.

Preferably, for vinyl ester carbonylation, the cycloalkyl moiety which is substituted by A and B at adjacent positions on the ring has a cis-conformation with respect to the A and B substituents.

Preferably, the cycloalkyl moiety has from 3 up to 20 cyclic atoms, more preferably from 4 up to 18 cyclic atoms, most preferably from 4 up to 12 cyclic atoms and especially 5 to 8 cyclic atoms and may be monocyclic or polycyclic. The cyclic atoms may be carbon or hetero, wherein references to hetero herein are references to sulphur, oxygen and/or nitrogen. Typically, the cycloalkyl moiety has from 2 up to 20 cyclic carbon atoms, more preferably from 3 up to 18 cyclic carbon atoms, most preferably from 3 up to 12 cyclic carbon atoms and especially 3 to 8 cyclic carbon atoms, may be monocyclic or polycyclic and may or may not be interrupted by one or more hetero atoms. Typically, when the cycloalkyl moiety is polycyclic it is preferably bicyclic or tricyclic. The cycloalkyl moieties as defined herein may include unsaturated bonds insofar as the said adjacent cyclic carbon atoms are saturated and references to unsaturated cycloalkyl moieties should be understood accordingly. By cyclic atom is meant an atom which forms part of the cyclic skeleton.

The cycloalkyl moiety, apart from that it may be interrupted with hetero atoms may be unsubstituted or substituted with one or more further substituents selected from aryl, lower alkyl (which alkyl group may itself be optionally substituted or terminated as defined below), hetero (preferably oxygen), Het, halo, cyano, nitro,
—$OR^{19}$, —$OC(O)R^{20}$, —$C(O)R^{21}$, —$C(O)OR^{22}$, —$N(R^{23})R^{24}$,
—$C(O)N(R^{25})R^{26}$, —$SR^{29}$, —$C(O)SR^{30}$, —$C(S)N(R^{27})R^{28}$ or —$CF_3$ wherein $R^{19}$-$R^{28}$ are as already defined herein.

For vinyl ester carbonylation the cycloalkyl moiety may be selected from cyclohexyl, cyclopentyl, cyclobutyl, cyclopropyl, cycloheptyl, cyclooctyl, cyclononyl, tricyclodecyl, piperidinyl, morpholinyl, norbornyl, isonorbornyl, norbornenyl, isonorbornenyl, bicyclo[2,2,2]octyl, tetrahydrofuryl, dioxanyl, O-2,3-isopropylidene-2,3-dihydroxy-ethyl, cyclopentanonyl, cyclohexanonyl, cyclopentenyl, cyclohexenyl, cyclohexadienyl, cyclobutenyl, cyclopentenonyl, cyclohexenonyl, adamantyl, furans, pyrans, 1,3 dioxane, 1,4 dioxane, oxocene, 7-oxabicyclo[2.2.1]heptane, pentamethylene sulphide, 1,3 dithiane, 1,4 dithiane, furanone, lactone, butyrolactone, pyrone, succinic anhydride, cis and trans 1,2-cyclohexanedicarboxylic anhydride, glutaric anhydride, pyrollidine, piperazine, imidazole 1,4,7 triazacyclononane, 1,5,9 triazacyclodecane, thiomorpholine, thiazolidine, 4,5-diphenyl-cyclohexyl, 4 or 5-phenyl-cyclohexyl, 4,5-dimethyl-cyclohexyl, 4 or 5-methylcyclohexyl, 1,2-decalinyl, 2,3,3a,4,5,6,7,7a-octahydro-1H-inden-5,6-yl, 3a,4,5,6,7,7a-hexahydro-1H-inden-5,6-yl, 1, 2 or 3 methyl-3a,4,5,6,7,7a hexahydro-1H-inden-5,6-yl, trimethylene norbornanyl, 3a,4,7,7a-tetrahydro-1H-inden-5,6-yl, 1, 2 or 3-dimethyl-3a,4,5,6,7,7a-hexahydro-1H-inden 5,6-yls, 1,3-bis(trimethylsilyl)-3a,4,5,6,7,7a-hexahydro-3H-isobenzofuran.

Particularly preferred combinations in the present invention for vinyl ester carbonylation include those wherein:—
(1) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;
A and B are the same and represent —$CH_2$—;
$Q^1$ and $Q^2$ both represent phosphorus;
R represents cis-cyclohexyl.
(2) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;
A and B are the same and represent —$CH_2$—;
$Q^1$ and $Q^2$ both represent phosphorus;
R represents cis-cyclopentyl.
(3) $X^3$ and $X^4$ together with $Q^1$ to which they are attached form a 2-phospha-adamantyl group, and, $X^1$ and $X^2$ together with $Q^2$ to which they are attached form a 2-phospha-adamantyl group;
A and B are the same and represent —$CH_2$—;
$Q^1$ and $Q^2$ both represent phosphorus;
R represents cis-cyclohexyl.
(4) $X^1$, $X^2$, $X^3$ and $X^4$ represent adamantyl;
A and B are the same and represent —$CH_2$—;
$Q^1$ and $Q^2$ both represent phosphorus;
R represents cis-cyclohexyl.

Still further preferred compounds of formula I or V for vinyl ester carbonylation include those wherein:
$R^1$ to $R^{12}$ are alkyl and are the same and preferably, each represents $C_1$ to $C_6$ alkyl, particularly methyl.

Especially preferred specific compounds of formula I or V for vinyl ester carbonylation include those wherein:
each $R^1$ to $R^{12}$ is the same and represents methyl;
A and B are the same and represent —$CH_2$—;
R represents 4,5 dimethyl-cis-1,2-cyclohexyl.

Examples of suitable bidentate ligands are cis-1,2-bis(di-t-butylphosphinomethyl)cyclohexane; cis-1,2-bis(di-t-butylphosphinomethyl)cyclopentane, cis-1,2-bis(di-t-butylphosphinomethyl)cyclobutane; cis-1,2-bis(2-phosphinomethyl-1,3,5,7-tetramethyl-6,9,10-trioxa-adamantyl)cyclohexane; cis-1,2-bis(2-phosphinomethyl-1,3,5,7-tetramethyl-6,9,10-trioxa-adamantyl)cyclopentane; cis-1,2-bis(2-phosphinomethyl-1,3,5,7-tetramethyl-6,9,10-trioxa-adamantyl)cyclobutane; cis-1,2-bis(di-adamantylphosphinomethyl)cyclohexane; cis-1,2-bis(di-adamantylphosphinomethyl)cyclopentane; cis-1,2-bis(di-adamantylphosphinomethyl)cyclobutane; cis-1-(P,P-adamantyl, t-butyl-phosphinomethyl)-2-(di-t-butylphosphinomethyl)cyclohexane; cis-1-(P,P-adamantyl, t-butyl-phosphinomethyl)-2-(di-t-butylphosphinomethyl)cyclopentane; cis-1-(P,P-adamantyl, t-butyl-phosphinomethyl)-2-(di-t-butylphosphinomethyl)cyclobutane; cis-1-(2-phosphinomethyl-1,3,5,7-tetramethyl-6,9,10-trioxa-adamantyl)-2-(di-t-butylphosphinomethyl)cyclohexane; cis-1-(2-phosphinomethyl-1,3,5,7-tetramethyl-6,9,10-trioxa-adamantyl)-2-(di-t-butylphosphinomethyl)cyclopentane; cis-1-(2-phosphinomethyl-1,3,5,7-tetramethyl-6,9,10-trioxa-adamantyl)-2-(di-t-butylphosphinomethyl)cyclobutane; cis-1-(2-phosphinomethyl-1,3,5,7-tetramethyl-6,9,10-trioxa-adamantyl)-2-(diadamantylphosphinomethyl)cyclohexane; cis-1-(2-phosphinomethyl-1,3,5,7-tetramethyl-6,9,10-trioxa-adamantyl)-2-(diadamantylphosphinomethyl)cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)cyclohexane; cis-1-(di-t-butylphosphinomethyl)-2-(diadamantylphosphinomethyl)cyclopentane; cis-1-(di-t-butylphosphinomethyl)-2-(diadamantylphosphinomethyl)cyclobutane; cis-1,2-bis(2-phosphinomethyl-1,3,5-trimethyl-6,9,10-trioxatricyclo-{3.3.1.1[3.7]}decyl)cyclohexane; cis-1,2-bis(2-phosphinomethyl-1,3,5-trimethyl-6,9,10-trioxatricyclo-{3.3.1.1[3.7]}decyl)cyclopentane; cis-1,2-bis(2-phosphinomethyl-1,3,5-trimethyl-6,9,10-trioxatricyclo-{3.3.1.1[3.7]}decyl)cyclobutane; cis-1-(2-phosphinomethyl-1,3,5-trimethyl-6,9,10-trioxatricyclo-{3.3.1.1[3.7]}decyl)-2-(di-t-butylphosphinomethyl)cyclohexane; cis-1-(2-phosphinomethyl-1,3,5-trimethyl-6,9,10-trioxatricyclo-{3.3.1.1[3.7]}decyl)-2-(di-t-butylphosphinomethyl)cyclopentane; cis-1-(2-phosphinomethyl-1,3,5-trimethyl-6,9,10-trioxatricyclo-{3.3.1.1[3.7]}decyl)-2-(di-t-butylphosphinomethyl)cyclobutane; cis-1-(2-phosphinomethyl-1,3,5-trimethyl-6,9,10-trioxatricyclo-{3.3.1.1[3.7]}decyl)-2-(diadamantylphosphinomethyl)cyclohexane; cis-1-(2-phosphinomethyl-1,3,5-trimethyl-6,9,10-trioxatricyclo-{3.3.1.1[3.7]}decyl)-2-(diadamantylphosphinomethyl)cyclopentane; cis-1-(2-phosphinomethyl-1,3,5-trimethyl-6,9,10-trioxatricyclo-{3.3.1.1[3.7]}decyl)-2-(diadamantylphosphinomethyl)cyclobutane; cis-1,2-bis-perfluoro (2-phosphinomethyl-1,3,5,7-tetramethyl-6,9,10-trioxatricyclo {3.3.1.1[3.7]}-decyl) cyclohexane; cis-1,2-bis-perfluoro (2-phosphinomethyl-1,3,5,7-tetramethyl-6,9,10-trioxatricyclo {3.3.1.1[3.7]}decyl) cyclopentane; cis-1,2-bis-perfluoro (2-phosphinomethyl-1,3,5,7-tetramethyl-6,9,10-trioxatricyclo {3.3.1.1[3.7]}decyl) cyclobutane; cis-1,2-bis-(2-phosphinomethyl-1,3,5,7-tetra (trifluoro-methyl)-6,9,10-trioxatricyclo {3.3.1.1[3.7]}decyl) cyclohexane; cis-1,2-bis-(2-phosphinomethyl-1,3,5,7-tetra (trifluoro-methyl)-6,9,10-trioxatricyclo {3.3.1.1[3.7]}decyl) cyclopentane; and cis-1,2-bis-(2-phosphinomethyl-1,3,5,7-tetra(trifluoro-methyl)-6,9,10-trioxatricyclo {3.3.1.1[3.7]}decyl)cyclobutane and including all cis enantiomers of the foregoing where such enantiomers are possible.

Examples of norbornyl bridged ligands for vinyl ester carbonylation include:—

(2-exo, 3-exo)-bicyclo[2.2.1]heptane-2,3-bis (di-tert-butylphosphinomethyl)

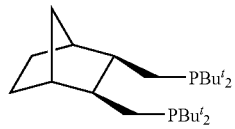

(2-endo, 3-endo)-bicyclo[2.2.1]heptane-2,3-bis (di-tert-butylphosphinomethyl)

Examples of substituted ligands include:—

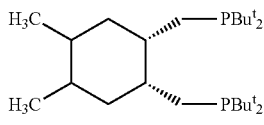

cis-1,2-bis
(di-tert-butylphosphinomethyl),
4,5 dimethylcyclohexane

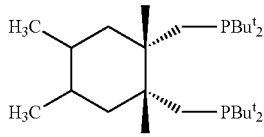

cis-1,2-bis
(di-tert-butylphosphinomethyl),
1,2,4,5 tetramethylcyclohexane

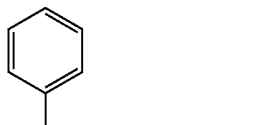

cis-1,2-bis(di-tert-
butylphosphinomethyl),
3,6,diphenylcyclohexane

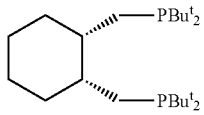

cis-1,2-bis(di-tert-
butylphosphinomethyl)
cyclohexane

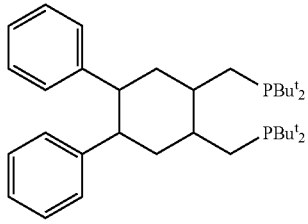

cis-1,2 bis
(di-tert-butyl(phosphinomethyl)-
4,5 diphenyl cyclohexane

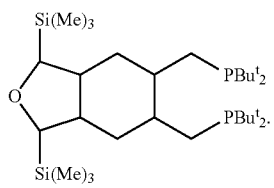

cis-5,6-bis
(di-tert-butylphosphinomethyl)-
1,3-bis(trimethylsilyl)-
3a,4,5,6,7,7a-hexahydro-
1,3H-isobenzofuran It will be appreciated by those skilled in the art that the compounds of formula (I) or (V) may function as ligands that coordinate with the Group 8, 9 or 10 metal or compound thereof to form the compounds for use in the invention. Typically, the Group 8, 9 or 10 metal or compound thereof coordinates to the one or more phosphorous, arsenic and/or antimony atoms of the compound of formula (I) or (V).

The present invention provides a process for the carbonylation of ethylenically unsaturated compound such as a vinyl ester or ethylene comprising contacting an ethylenically unsaturated compound with carbon monoxide and a source of hydroxyl groups such as water or an alkanol in the presence of a catalyst compound as defined in the present invention.

Suitably, the source of hydroxyl groups includes an organic molecule having an hydroxyl functional group. Preferably, the organic molecule having a hydroxyl functional group may be branched or linear, and comprises an alkanol, particularly a $C_1$-$C_{30}$ alkanol, including aryl alkanols, which may be optionally substituted with one or more substituents selected from lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{27}R^{28}$, $SR^{29}$ or $C(O)SR^{30}$ as defined herein. Highly preferred alkanols are $C_1$-$C_8$ alkanols such as methanol, ethanol, propanol, iso-propanol, iso-butanol, t-butyl alcohol, n-butanol, phenol and chlorocapryl alcohol. Although the monoalkanols are most preferred, poly-alkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol.

The amount of alcohol is not critical. Generally, amounts are used in excess of the amount of vinyl ester compound to be carbonylated. Thus the alcohol may serve as the reaction solvent as well, although, if desired, separate solvents may also be used.

It will be appreciated that the end product of the reaction is determined at least in part by the source of alkanol used. For instance, use of methanol produces the corresponding methyl ester, for example, with vinyl ester, methanol produces the 2-acetoxy methyl propanoate or 3-acetoxymethyl propanoate. Conversely, use of water produces the corresponding acids. Accordingly, the invention provides a convenient way of adding the group —$C(O)OR^{31}$ or —$C(O)OH$ across the ethylenically unsaturated bond.

In the process according to the present invention, the carbon monoxide may be used in pure form or diluted with an inert gas such as nitrogen, carbon dioxide or a noble gas such as argon. Small amounts of hydrogen, typically less than 5% by volume, may also be present.

The ratio (volume/volume) of ethylenically unsaturated compounds to hydroxyl group source may vary between wide limits and suitably lies in the range of 1:0.1 to 1:10, preferably from between 2:1 to 1:2 and up to a large excess of alkanol or water when the latter is also the reaction solvent such as up to a 50:1 excess of alkanol or water.

The amount of the catalyst of the invention used in the carbonylation process of the vinyl ester is not critical. Good results may be obtained when, preferably, the amount of Group 8, 9 or 10 metal is in the range $10^{-7}$ to $10^{-1}$ moles per mole of vinyl ester, more preferably, $10^{-6}$ to $10^{-2}$ moles, most preferably $10^{-5}$ to $10^{-2}$ moles per mole of ester. Preferably, the amount of bidentate compound of formula I or V to unsaturated compound is in the range $10^{-7}$ to $10^{-1}$, more preferably, $10^{-6}$ to $10^{-2}$, most preferably, $10^{-5}$ to $10^{-2}$ moles per mole of ethylenically unsaturated compound.

Suitably, although non-essential to the invention, the carbonylation of ethylenically unsaturated compound as defined herein may be performed in one or more aprotic solvents. Suitable solvents include ketones, such as for example methylbutylketone; ethers, such as for example anisole (methyl phenyl ether), 2,5,8-trioxanonane (diglyme), diethyl ether, dimethyl ether, tetrahydrofuran, diphenylether, diisopropylether and the dimethylether of di-ethylene-glycol; esters, such as for example methylacetate, dimethyladipate methyl benzoate, dimethyl phthalate and butyrolactone; amides, such as for example dimethylacetamide, N-methylpyrrolidone and dimethyl formamide; sulfoxides and sulphones, such as for example dimethylsulphoxide, di-isopropylsulphone, sulfolane (tetrahydrothiophene-2,2-dioxide), 2-methylsulfolane, diethyl sulphone, tetrahydrothiophene 1,1-dioxide and 2-methyl-4-ethylsulfolane; aromatic compounds, including halo variants of such compounds e.g. benzene, toluene, ethyl benzene o-xylene, m-xylene, p-xylene, chlorobenzene, o-dichlorobenzene, m-dichlorobenzene: alkanes, including halo variants of such compounds egg, hexane, heptane, 2,2,3-trimethylpentane, methylene chloride and carbon tetrachloride; nitriles e.g. benzonitrile and acetonitrile.

Very suitable are aprotic solvents having a dielectric constant that is below a value of 50, more preferably in the range of 3 to 8, at 298.15 K and $1\times10^5 Nm^{-2}$. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, $76^{th}$ edition, edited by David R. Lide et al, and published by CRC press in 1995, and are usually quoted for a temperature of about 20° C. or 25° C., i.e. about 293.15 k or 298.15 K, and atmospheric pressure, i.e. about $1\times10^5 Nm^{-2}$, or can readily be converted to that temperature and pressure using the conversion factors quoted. If no literature data for a particular compound is available, the dielectric constant may be readily measured using established physico-chemical methods.

For example, the dielectric constant of anisole is 4.3 (at 294.2 K), of diethyl ether is 4.3 (at 2932 K), of sulfolane is 43.4 (at 303.2 K), of methylpentanoate is 5.0 (at 293.2 K), of diphenylether is 3.7 (at 283.2 K), of dimethyladipate is 6.8 (at 293.2 K), of tetrahydrofuran is 7.5 (at 295.2 K), of methylnonanoate is 3.9 (at 293.2 K). A preferred aprotic solvent is anisole.

In the presence of an alkanol, an aprotic solvent will be generated by the reaction as the ester carbonylation product of the ethylenically unsaturated compound, carbon monoxide and the alkanol is an aprotic solvent.

The process may be carried out in an excess of aprotic solvent, i.e. at a ratio (v/v) of aprotic solvent to alkanol of at least 1:1. Preferably, this ratio ranges from 1:1 to 10:1 and more preferably from 1:1 to 5:1. Most preferably the ratio (v/v) ranges from 1.5:1 to 3:1.

Despite the foregoing it is preferred that the reaction is carried out in the absence of any external added aprotic solvent i.e. in the absence of an aprotic solvent not generated by the reaction itself.

During hydroxycarbonylation, the presence of a protic solvent is also preferred. The protic solvent may include a carboxylic acid or an alcohol. In the case of vinyl esters, a particularly suitable protic solvent is the acid complement of the vinyl ester. Mixtures of the aprotic and protic solvents may also be employed.

Hydrogen may be added to the carbonylation reaction to improve reaction rate. Suitable levels of hydrogen when utilised may be in the ratio of between 0.1 and 20% vol/vol of the carbon monoxide, more preferably, 1-20% vol/vol of the carbon monoxide, more preferably, 2-15% vol/vol of the carbon monoxide, most preferably 3-10% vol/vol of carbon monoxide.

The catalyst compounds of the present invention may act as a "heterogeneous" catalyst or a "homogeneous" catalyst, preferably, a homogenous catalyst.

By the term "homogeneous" catalyst we mean a catalyst, i.e. a compound of the invention, which is not supported but is simply admixed or formed in-situ with the reactants of the carbonylation reaction (e.g. the ethylenically unsaturated compound, the hydroxyl containing compound and carbon monoxide), preferably in a suitable solvent as described herein.

By the term "heterogeneous" catalyst we mean a catalyst, i.e. the compound of the invention, which is carried on a support.

Thus according to a further aspect, the present invention provides a process for the carbonylation of ethylenically unsaturated compounds as defined herein wherein the process is carried out with the catalyst comprising a support, preferably an insoluble support.

Preferably, the support comprises a polymer such as a polyolefin, polystyrene or polystyrene copolymer such as a divinylbenzene copolymer or other suitable polymers or copolymers known to those skilled in the art; a silicon derivative such as a functionalised silica, a silicone or a silicone rubber; or other porous particulate material such as for example inorganic oxides and inorganic chlorides.

Preferably the support material is porous silica which has a surface area in the range of from 10 to 700 $m^2/g$, a total pore volume in the range of from 0.1 to 4.0 cc/g and an average particle size in the range of from 10 to 500 μm. More preferably, the surface area is in the range of from 50 to 500 $m^2/g$, the pore volume is in the range of from 0.5 to 2.5 cc/g and the average particle size is in the range of from 20 to 200 μm. Most desirably the surface area is in the range of from 100 to 400 $m^2/g$, the pore volume is in the range of from 0.8 to 3.0 cc/g and the average particle size is in the range of from 30 to 100 μm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or a rigid support, the insoluble support is coated and/or impregnated with the compounds of the process of the invention by techniques well known to those skilled in the art.

Alternatively, the compounds of the process of the invention are fixed to the surface of an insoluble support, optionally via a covalent bond, and the arrangement optionally includes a bifunctional spacer molecule to space the compound from the insoluble support.

The compounds of the invention may be fixed to the surface of the insoluble support by promoting reaction of a functional group present in the compound of formula I or V, for example a substituent of the cycloalkyl moiety, with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the process of the present invention to the support depends upon the ethylenically unsaturated compound and the groups of the support. For example, reagents such as carbodiimides, 1,1'-carbonyldiimidazole, and processes such as the use of mixed anhydrides, reductive amination may be employed.

According to a further aspect, the present invention provides the use of the process or catalyst of any aspect of the invention wherein the catalyst is attached to a support.

Additionally, the bidentate phosphine may be bonded to a suitable polymeric substrate via at least one of the bridge substituents (including the cyclic atoms) the bridging group R, the linking group A or the linking group B e.g. cis-1,2-bis (di-t-butylphosphinomethyl)cyclohexane may be bonded, preferably, via the 3, 4, 5 or 6 cyclic carbons of the cyclohexane group to polystyrene to give an immobile heterogeneous catalyst.

The amount of bidentate ligand used can vary within wide limits. Preferably, the bidentate ligand is present in an amount such that the ratio of the number of moles of the bidentate ligand present to the number of moles of the Group 8, 9 or 10 metal present is from 1 to 50 e.g. 1 to 10 and particularly from 1 to 5 mol per mol of metal. More preferably, the mol:mol range of compounds of formula I or V to Group 8, 9 or 10 metal is in the range of 1:1 to 3:1, most preferably in the range of 1:1 to 1.5:1. Conveniently, the possibility of applying these low molar ratios is advantageous, as it avoids the use of an excess of the compound of formula I or V and hence minimises the consumption of these usually expensive compounds. Suitably, the catalysts of the invention are prepared in a separate step preceding their use in-situ in the carbonylation reaction.

Conveniently, the process of the invention may be carried out by dissolving the Group 8, 9 or 10 metal or compound thereof as defined herein in a suitable solvent such as one of the alkanols or aprotic solvents previously described (a particularly preferred solvent would be the ester or acid product of the specific carbonylation reaction e.g. Methyl lactate for vinyl acetate carbonylation) and subsequently admixing with a compound of formula I or V as defined herein.

The carbon monoxide may be used in the presence of other gases which are inert in the reaction. Examples of such gases include hydrogen, nitrogen, carbon dioxide and the noble gases such as argon.

The molar ratio of the amount of ethylenically unsaturated compound such as vinyl ester or ethylene used in the reaction to the amount of alkanol is not critical and may vary between wide limits, e.g. from 0.001:1 to 100:1 mol/mol.

The product of the reaction may be separated from the other components by any suitable means. However, it is an advantage of the present process that significantly fewer by-products are formed thereby reducing the need for further purification after the initial separation of the product as may be evidenced by the generally significantly higher selectivity. A further advantage is that the other components which contain the catalyst system which may be recycled and/or reused in further reactions with minimal supplementation of fresh catalyst.

Preferably, the carbonylation is carried out at temperatures of between −30 to 170° C., more preferably −10° C. to 160° C., most preferably 20° C. to 150° C. An especially preferred temperature is one chosen between 40° C. to 150° C. Advantageously, the carbonylation can be carried out at moderate temperatures, it is particularly advantageous to be able to carry out the reaction at room temperature (20° C.).

Preferably, when operating a low temperature carbonylation, the carbonylation is carried out between −30° C. to 49° C., more preferably, −10° C. to 45° C., still more preferably 0° C. to 45° C., most preferably 10° C. to 45° C. Especially preferred is a range of 10 to 35° C.

Preferably, the carbonylation is carried out at a CO partial pressure of between $0.80 \times 10^5$ $N \cdot m^{-2}$–$90 \times 10^5 N \cdot m^{-2}$, more preferably $1 \times 10^5$ $N \cdot m^{-2}$–$65 \times 10^5 N \cdot m^{-2}$, most preferably $1$–$50 \times 10^5$ $N \cdot m^{-2}$. Especially preferred is a CO partial pressure of 5 to $45 \times 10^5 N \cdot m^{-2}$.

Preferably, a low pressure carbonylation is also envisaged. Preferably, when operating a low pressure carbonylation the carbonylation is carried out at a CO partial pressure of between 0.1 to $5 \times 10^5 N \cdot m^{-2}$, more preferably 0.2 to $2 \times 10^5 N \cdot m^{-2}$, most preferably 0.5 to $1.5 \times 10^5 N \cdot m^{-2}$.

There is no particular restriction on the duration of the carbonylation except that carbonylation in a timescale which is commercially acceptable is obviously preferred. Carbonylation in a batch reaction may take place in up to 48 hours, more typically, in up to 24 hours and most typically in up to 12 hours. Typically, carbonylation is for at least 5 minutes, more typically, at least 30 minutes, most typically, at least 1 hour. In a continuous reaction such time scales are obviously irrelevant and a continuous reaction can continue as long as the TON is commercially acceptable before catalyst requires replenishment.

The catalyst system of the present invention is preferably constituted in the liquid phase which may be formed by one or more of the reactants or by the use of a suitable solvent.

As mentioned above, when the ethylenically unsaturated compound is vinyl ester, the vinyl ester can be substituted or non-substituted. However, it is preferred that the vinyl ester is unsubstituted. Suitable vinyl esters are vinyl acetate, vinyl propanoate, vinyl-formate, Vinyl-chloroformate, Vinyl-chloroacetate, Vinyl-trifluoroacetate, Vinyl-propionate, Vinyl-acrylate, Vinyl-methacryate, Vinyl-crotonate, Vinyl-butyrate, Vinyl-pivalate, Vinyl-2-ethyl hexanoate, Vinyl-decanoate, Vinyl-neodecanoate, Vinyl-dodecanoate, Vinyl-benzoate, Vinyl-4-tert-butylbenzoate and Vinyl-salicylate.

The use of stabilising compounds with the catalyst system may also be beneficial in improving recovery of metal which has been lost from the catalyst system. When the catalyst system is utilized in a liquid reaction medium such stabilizing compounds may assist recovery of the group 8, 9 or 10 metal.

Preferably, therefore, the catalyst system includes in a liquid reaction medium a polymeric dispersant dissolved in a liquid carrier, said polymeric dispersant being capable of stabilising a colloidal suspension of particles of the group 8, 9 or 10 metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said group 8, 9 or 10 metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed group 8, 9 or 10 metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles redispersed by agitation.

The polymeric dispersant may include homopolymers or copolymers including polymers such as grail copolymers and star polymers.

Preferably, the polymeric dispersant has sufficiently acidic or basic functionality to substantially stabilise the colloidal suspension of said group 8, 9 or 10 metal or metal compound.

By substantially stabilise is meant that the precipitation of the group 8, 9 or 10 metal from the solution phase is substantially avoided.

Particularly preferred dispersants for this purpose include acidic or basic polymers including carboxylic acids, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly (vinylsulphonic acid), acylated polyethylenimine. Suitable acylated polyethyleneimines are described in BASF patent publication EP1330309 A1 and U.S. Pat. No. 6,723,882.

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrrolidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed group 8, 9 or 10 metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably, between 1:1 and 200:1. Preferably, the polymer: metal mass ratio in g/g is up to 1000, more preferably, up to 400, most preferably, up to 200.

It will be appreciated that any of the features set forth in the first aspect of the invention may be regarded as preferred features of the second, third, fourth, fifth or other aspect of the present invention and vice versa.

The invention also extends to novel bidentate ligands of formula (I) or (V) and novel complexes of such ligands with the metal of Group 8, 9 or 10 or a compound thereof.

The invention will now be described and illustrated by way of the following non-limiting examples and comparative examples.

COMPARATIVE AND PREPARATIVE EXAMPLE 1

Preparation of cis-1,2-bis(di-tert-butylphosphinomethyl)cyclohexane

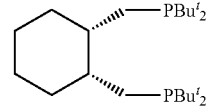

1. a) Preparation of cis-(1,2 dibromomethyl)cyclohexane

The cis-cyclohexanedimethanol (30.0 g, 210 mmol) was partially dissolved in HBr (48%, 55 ml, 486 mmol) and to this was added $H_2SO4$ (98%, 88 ml, 1618 mmol) slowly. The resultant brown suspension was then heated to 100° C. for five hours. The brown suspension was allowed to cool to room temperature and diluted with water (100 ml) and diethyl ether (2*200 ml). The organic layer was collected by separation and washed with water (200 ml) and 10% sodium carbonate solution (100 ml) and water (2*150 ml). The organic layer was then dried over sodium sulphate and filtered. The filtrate was then dried under vacuum to give brown oil. Yield=47.0 g, 83%. 99% pure by $^1H$ NMR. FW=270.00.

1. b) Preparation of cis-1,2-bis(di-tert-butylphosphinomethyl)cyclohexane $Bu^t_2PH.BH_3$ (19.6 g, 122 mmol) was dissolved in THF (100 ml) to this was slowly added $Bu^nLi$ (2.5M in hexanes, 48.9 ml, 122 mmol). The resultant solution was then stirred at room temperature for two hours. This was then added to a solution of cis-(1,2-dibromomethyl)cyclohexane from example 1a) (15.0 g, 55.6 mmol) in THF (100 ml) dropwise. The resultant solution was then stirred for four hours before being stood for 16 hours. The reaction was quenched with methanol (50 ml) and the volume was removed under vacuum. The resultant orange oily solid was suspended in diethyl ether (200 ml) and to this was added tetrafluoroboric acid (54% in diethyl ether, 367 mmol, 50.5 ml). This gave rapid gas evolution and the solution was heated to reflux for two hours before being stood for 16 hours open to nitrogen. The solvent was then removed under vacuum and the residue suspended in methanol (100 ml) and the suspension stirred for two hours. Some gas evolution was observed. The methanol was then removed under vacuum. In a separate Schlenk flask was added potassium hydroxide (30.0 g, 454 mmol), this was dissolved in water (100 ml) and the subsequent solution degassed with nitrogen for 30 minutes. The KOH solution was then added dropwise to the phosphine residue. This gave heat evolution and a white suspension. Pentane (2*100 ml) was added. The organic extracts were removed by cannula to a separate Schlenk. The organic extracts were dried over sodium sulphate and filtered. The filtrate was then dried under vacuum to give colourless oil. Yield=11.8 g, 53%. $^{31}P\{^{1}H\}$ NMR: δ=25 ppm, >95% pure.

COMPARATIVE AND PREPARATIVE EXAMPLE 2

Preparation of Trans-1,2-bis(di-tert-butylphosphinomethyl)cyclohexane

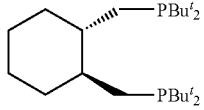

2. a) Preparation of Trans-Cyclohexanedimethanol

The trans-1,2-cyclohexanecarboxylic acid (25.0 g, 145 mmol) was placed in a schlenk flask and LiAlH$_4$ (1M in THF, 290 mmol, 290 ml) was added slowly. The resultant colourless solution was then heated to 75° C. for sixteen hours. The solution was then cooled to room temperature and quenched with water (200 ml), exothermic addition. This gave a large volume of white solid. The THF layer was collected by filtration and the white precipitate washed with diethyl ether (2*200 ml). The combined organic extracts were dried over sodium sulphate and filtered. The filtrate was then dried under vacuum to give a colourless oil. Yield=16.8 g, 81%.

2. b) Preparation of Trans-(1,2 dibromomethyl)cyclohexane

The diol from Example 2a (16.8 g, 117.6 mmol) was diluted with HBr (48%, 30.8 ml, 272 mmol) and to this was slowly added H2SO4 (98%, 49 ml, 906 mmol). This gave an orange suspension, this was then heated to 100° C. for five hours to give a dark brown/black liquid. The suspension was then allowed to cool to room temperature and was diluted with water (100 ml). The product was extracted into diethyl ether (2*200 ml). The combined organic extracts were washed with water (2*200 ml), 10% sodium carbonate solution (250 ml) and water (250 ml). The organic extract was then dried over sodium sulphate and filtered. The filtrate was then dried under vacuum to give a brown oil. Yield=23.0 g, 72%.

2. c) Preparation of Trans-1,2-bis(di-tert-butylphosphinomethyl)cyclohexane

The Bu$^t{}_2$PH.BH$_3$ (13.0 g, 81.5 mmol) was dissolved in THF (50 ml) and n-butyl lithium added (2.5M in hexanes, 32.6 ml, 81.5 mmol) added. The resultant yellow solution was then stirred at room temperature for one hour. The dibromide from example 2.b) (10.0 g, 37 mmol) was dissolved in THF (50 ml) and the lithium phosphide solution added dropwise. The resultant solution was then heated for 30 minutes at 50° C. The orange/red solution was then cooled to room temperature. The solution was then quenched with methanol (50 ml) and stirred for 30 minutes. The solvent was then removed under vacuum. The phosphine was then suspended in diethyl ether (200 ml) and HBF4 (54% in diethyl ether, 30.5 ml, 222 mmol) was added slowly.

This gave gas and heat evolution. The resultant suspension was then heated to reflux for sixteen hours. The excess solvent was then removed under vacuum and the residue suspended in methanol (50 ml). The methanol suspension was then stirred for 30 minutes. The methanol was then removed under vacuum and a solution of KOH (13 g, 231.7 mmol) in water (75 ml, degassed with nitrogen gas for 30 minutes) added slowly. This gave heat evolution and a white suspension. This was then washed with pentane (2*250 ml) and the combined pentane washings dried over sodium sulphate. The pentane washings were then transferred by cannula into a clean schlenk flask and then dried under vacuum. This was extracted into pentane (50 ml) and some insoluble white material was observed. The pentane soluble material was cannula transferred into a clean schlenk flask and the solvent removed under vacuum. This gave a yellow oily solid. Yield=5.35 g, 36%. $^{31}P\{^{1}H\}$ NMR: δ=22.3 ppm, >95% pure.

COMPARATIVE AND PREPARATIVE EXAMPLE 3

Preparation of (2-exo, 3-exo)-bicyclo[2.2.1]heptane-2,3-bis(di-tert-butylphosphinomethyl)

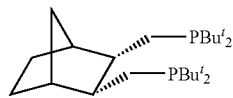

3. a) Preparation of (2-exo, 3-exo)-bicyclo[2.2.1] heptane-2,3-bis(p-toluenesulfonyl-methyl)

The equivalent (2-exo-, 3-exo) bicyclo[2.2.1]heptane dimethanol (commercially available) (21 g, 134.6 mmol) was diluted with pyridine (50 ml) and cooled to 0° C. To this was added p-toluene sulfonyl chloride (TsCl, 56.46 g, 296 mmol) in pyridine (100 ml) over five minutes. The resultant suspension was allowed to warm to room temperature and diluted with a further 50 ml of pyridine. The suspension was then stirred at room temperature overnight. The suspension was then poured into a beaker containing HCl (concentrated, 100 ml) and water (500 ml). This gave a white solid which floated on the top of the solution. This solid was isolated on a frit and washed with water (4*250 ml). The white solid was then dried under vacuum. Yield=24.0 g, 41%.

3. b) Preparation of (2-exo, 3-exo)-bicyclo[2.2.1] heptane-2,3-bis(di-tert-butylphosphinomethyl)diborane The Bu$^t_2$PH.BH$_3$ (19.2 g, 120 mmol) was dissolved in THF (150 ml) and n-butyl lithium (2.5M in hexanes, 52.8 ml, 120 mmol) added. The resultant yellow solution was then stirred at room temperature for one hour. The ditosylate (3a) (24.0 g, 54.54 mmol) was suspended in THF (100 ml) and the lithium phosphide solution added dropwise. This gave a grey suspension. This was stirred for one hour and then stood overnight. The suspension was quenched with water (100 ml) and the product extracted into diethyl ether (2*200 ml). The combined ether extracts were washed with water (4*250 ml) and dried over sodium sulphate. The ether extract was then filtered and dried under vacuum. This gave a pale yellow solid. Yield=16.4 g, 73%.

3. c) Preparation of (2-exo, 3-exo)-bicyclo[2.2.1] heptane-2,3-bis(di-tert-butylphosphinomethyl)

The boronated phosphine (3b) (16.4 g, 39.8 mmol) was dissolved in diethyl ether (200 ml, and HBF4 (54% in diethyl ether, 44 ml, 318 mmol) added slowly. This gave gas and heat evolution. The solution was then heated to reflux for three days. This gave a large amount of white precipitate formation. The suspension was then cooled to room temperature and the ether solution removed by cannula. The residue was dried under vacuum and then suspended in methanol (50 ml). The methanol suspension was then stirred for thirty minutes before the methanol was removed under vacuum. To the residue was added a solution of potassium hydroxide (10 g, 178.2 mmol) in water (100 ml, degassed with nitrogen gas for thirty minutes). This gave heat evolution and the formation of a white precipitate. This was washed with pentane (2*250 ml). The combined pentane washings were dried with sodium sulphate and then transferred into a clean schlenk flask by cannula. The pentane was then removed under vacuum to give a white solid. Yield=8.4 g, 51%. $^{31}$P {$^1$H} NMR: δ=26.4 ppm, >95% pure.

COMPARATIVE AND PREPARATIVE EXAMPLE 4

Preparation of (2-endo, 3-endo)-bicyclo[2.2.1]heptane-2,3-bis(di-tert-butylphosphinomethyl)

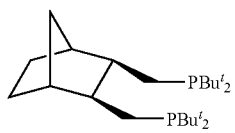

4. a) Preparation of (2-endo, 3-endo)bicyclo[2.2.1] heptane-2,3-bis(hydroxymethyl)

The equivalent anhydride (cis-5-Norbornene-endo-2,3-dicarboxylic anhydride) (22.2 g, 133.33 mmol) was dissolved in THF (100 ml) and LiAlH$_4$ (1M in THF, 200 mmol, 200 ml) was added slowly. The resultant colourless solution was then heated to 70° C. for sixteen hours. The solution was then cooled to room temperature and quenched with water (100 ml), exothermic addition. This gave a large volume of white solid. The THF layer was collected by filtration and the white precipitate washed with diethyl ether (2*150 ml). The combined organic extracts were dried over sodium sulphate and filtered. The filtrate was then dried under vacuum to give a colourless oil. Yield=18.9 g, 91%.

4. b) Preparation of (2-endo, 3-endo)bicyclo[2.2.1] heptane-2,3-bis(p-toluenesulfonyl-methyl)

The diol (4a, 18.9 g, 120.8 mmol) was diluted with pyridine (100 ml) and cooled in a cold water bath. To this was added p-toluene sulfonyl chloride (TsCl, 50.7 g, 266 mmol) in pyridine (100 ml) over five minutes. The resultant suspension was allowed to warm to room temperature and stirred at room temperature overnight. The suspension was then poured into a beaker containing HCl (concentrated, 100 ml) and water (500 ml). The organic product was extracted with diethyl ether (2*200 ml). The combined ether extracts were washed with water (4*250 ml) and dried over sodium sulphate. The ether extract was then filtered and the filtrate dried under vacuum. This gave a yellow oily solid. Yield=23.4 g, 48%.

4. c) Preparation of (2-endo, 3-endo)-bicyclo[2.2.1] heptane-2,3-bis(di-tert-butylphosphinomethyl)diborane The Bu$^t_2$PH.BH$_3$ (18.7 g, 117 mmol) was dissolved in THF (100 ml) and n-butyl lithium (2.5M in hexanes, 46.8 ml, 117 mmol) added. The resultant yellow solution was then stirred at room temperature for one hour. The ditosylate (4b) (23.4 g, 53.24 mmol) was dissolved in THF (100 ml) and the lithium phosphide solution added dropwise. This gave a bright yellow suspension. This was stirred for two hours and then stood overnight. The suspension was quenched with water (100 ml) and the product extracted into diethyl ether (2*300 ml). The combined ether extracts were washed with water (5*250 ml) and dried over sodium sulphate. The ether extract was then filtered and dried under vacuum. This gave a yellow oil. Yield=13.1 g, 60%.

4. d) Preparation of (2-endo, 3-endo)-bicyclo[2.2.1] heptane-2,3-bis(di-tert-butylphosphinomethyl)

The boronated phosphine (4.c) (13.1 g, 31.8 mmol) was dissolved in diethyl ether (200 ml, and HBF4 (54% in diethyl ether, 35 ml, 254 mmol) added slowly. This gave gas and heat evolution. The solution was then heated to reflux for three days. This gave a large amount of white precipitate formation. The suspension was then cooled to room temperature and the ether solution removed by cannula. The residue was dried under vacuum and then suspended in methanol (50 ml). The methanol suspension was then stirred for thirty minutes before the methanol was removed under vacuum. To the residue was added a solution of potassium hydroxide (10 g, 178.2 mmol) in water (100 ml, degassed with nitrogen gas for thirty minutes). This gave heat evolution and the formation of a white precipitate. This was washed with pentane (2*250 ml). The combined pentane washings were dried with sodium sulphate and then transferred into a clean schlenk flask by cannula. The pentane was then removed under vacuum to give a colourless oil. Yield=3.8 g, 29%. $^{31}$P {$^{1}$H} NMR: δ=24.6, 24.4, 22.4 ppm, >95% pure.

PREPARATIVE EXAMPLE 5

Preparation of cis-1,2-bis(di-tert-butylphosphinomethyl), 4,5 dimethylcyclohexane

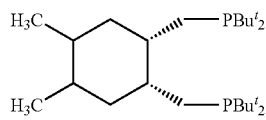

5. a) Preparation cis-1,2-bis(hydroxymethyl), 4,5 dimethylcyclohexane

The anhydride (4,5-dimethyl-is-1,2-cyclohexanedicarboxylic anhydride) (20.1 g, 110 mmol) was diluted with THF (50 ml) and cooled to 0° C. To this was added LiAlH$_4$ (1M in THF, 220 mmol, 220 ml) slowly. This gave gas and heat evolution. The resultant grey/yellow solution was then heated to 77° C. for sixteen hours. The solution was then cooled to room temperature and quenched with a solution of HCl (25 ml, concentrated) in water (100 ml), exothermic addition. This gave a large volume of white solid. Diethyl ether (200 ml) was then added. The organic layer was collected by filtration and the white precipitate washed with diethyl ether (2*100 ml). The combined organic extracts were dried over sodium sulphate and filtered. The filtrate was then dried under vacuum to give a colourless oil. Yield=15.0 g, 79%.

5. b) Preparation of cis-1,2-bis(p-toluenesulfonyl-methyl), 4,5 dimethylcyclohexane The diol (5a, 15.0 g, 87 mmol) was placed into a schlenk flask and cooled to 0° C. To this was added p-toluene sulfonyl chloride (TsCl, 36.6 g, 192 mmol) in pyridine (100 ml) over five minutes. The resultant suspension was allowed to warm to room temperature diluted with pyridine (50 ml). The suspension was then stirred at room temperature overnight. The suspension was then poured into a beaker containing HCl (concentrated, 100 ml) and water (500 ml). The organic product was extracted with diethyl ether (3*400 ml). The combined ether extracts were washed with water (3*600 ml) and dried over sodium sulphate. The ether extract was then filtered and the filtrate dried under vacuum. This gave a sticky white/yellow solid. Yield=18.1 g, 43%.

5. c) Preparation of cis-1,2-bis(di-tert-butylphosphinomethyl)Diborane, 4,5 Dimethylcyclohexane The Bu$^t_2$PH.BH$_3$ (13.3 g, 83 mmol) was dissolved in THF (50 ml) and n-butyl lithium (2.5M in hexanes, 33.2 ml, 83 mmol) added. The resultant yellow solution was then stirred at room temperature for one hour. The ditosylate (5 b) (18.1 g, 38 mmol) was dissolved in THF (100 ml) and the lithium phosphide solution added dropwise. This gave a bright yellow suspension. This was stirred for one hour and then stood overnight. The suspension was quenched with water (100 ml) and the product extracted into diethyl ether (2*250 ml). The combined ether extracts were washed with water (3*250 ml) and dried over sodium sulphate. The ether extract was then filtered and dried under vacuum. This gave a colourless oil. Yield=12.2 g, 75%.

5. d) Preparation of cis-1,2-bis(di-tert-butylphosphinomethyl), 4,5 dimethylcyclohexane The boronated phosphine (5c) (12.2 g, 28.5 mmol) was dissolved in diethyl ether (200 ml, and HBF4 (54% in diethyl ether, 31.3 ml, 228 mmol) added slowly. This gave gas and heat evolution. The solution was then heated to reflux for three days. This gave a large amount of white precipitate formation. The suspension was then cooled to room temperature and the ether solution removed by cannula. The residue was dried under vacuum and then suspended in methanol (50 ml). The methanol suspension was then stirred for thirty minutes before the methanol was removed under vacuum. To the residue was added a solution of potassium hydroxide (10 g, 178.2 mmol) in water (100 ml, degassed with nitrogen gas for thirty minutes). This gave heat evolution and the formation of a white precipitate. This was washed with pentane (2*250 ml). The combined pentane washings were dried with sodium sulphate and then transferred into a clean schlenk flask by cannula. The pentane was then removed under vacuum to give a colourless oil. Yield 4.2 g, 34%. $^{31}$P {$^{1}$H} NMR: δ=26.9, 25.4, 24.4 ppm, >95% pure.

COMPARATIVE AND PREPARATIVE EXAMPLE 6

Preparation of cis-1,2-bis(di-tert-butylphosphinomethyl), 3,6, diphenylcyclohexane

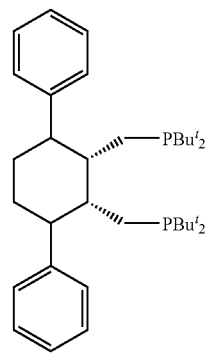

6. a) Preparation of cis-1,2-bis(hydroxymethyl), 3,6, diphenylcyclohexane

The anhydride (3,6-diphenyl-cis-1,2-cyclohexanedicarboxylic anhydride) (22.2 g, 133.33 mmol) was dissolved in THF (100 ml) and LiAlH$_4$ (1M in THF, 200 mmol, 200 ml) was added slowly. The resultant colourless solution was then heated to 70° C. for sixteen hours. The solution was then cooled to room temperature and quenched with water (100 ml), exothermic addition. This gave a large volume of white solid. The THF layer was collected by filtration and the white precipitate washed with diethyl ether (2*150 ml). The combined organic extracts were dried over sodium sulphate and filtered. The filtrate was then dried under vacuum to give a colourless oil. Yield=18.9 g, 91%.

6. b) Preparation of cis-1,2-bis(p-toluenesulfonyl-methyl), 3,6, diphenylcyclohexane The diol (7a)(18.9 g, 120.8 mmol) was diluted with pyridine (100 ml) and cooled in a cold water bath. To this was added p-toluene sulfonyl chloride (TsCl, 50.7 g, 266 mmol) in pyridine (100 ml) over five minutes. The resultant suspension was allowed to warm to room temperature and stirred at room temperature overnight. The suspension was then poured into a beaker containing HCl (concentrated, 100 ml) and water (500 ml). The organic product was extracted with diethyl ether (2*200 ml). The combined ether extracts were washed with water (4*250 ml) and dried over sodium sulphate. The ether extract was then filtered and the filtrate dried under vacuum. This gave a yellow oily solid. Yield=23.4 g, 48%.

6. c) Preparation of cis-1,2-bis(di-tert-butylphosphinomethyl)diborane, 3,6, Diphenylcyclohexane The $Bu^t_2PH.BH_3$ (18.7 g, 117 mmol) was dissolved in THF (100 ml) and n-butyl lithium (2.5M in hexanes. 46.8 ml, 117 mmol) added. The resultant yellow solution was then stirred at room temperature for one hour. The ditosylate (7b) (23.4 g, 53.24 mmol) was dissolved in THF (100 ml) and the lithium phosphide solution added dropwise. This gave a bright yellow suspension. This was stirred for two hours and then stood overnight. The suspension was quenched with water (100 ml) and the product extracted into diethyl ether (2*300 ml). The combined ether extracts were washed with water (5*250 ml) and dried over sodium sulphate. The ether extract was then filtered and dried under vacuum. This gave a yellow oil. Yield=5.7 g, 9%.

6. d) Preparation of cis-1,2-bis(di-tert-butylphosphinomethyl), 3,6, diphenylcyclohexane The boronated phosphine (7. c) (5.7 g, 10.3 mmol) was dissolved in diethyl ether (200 ml, and HBF4 (54% in diethyl ether, 11.4 ml, 82.6 mmol) added slowly. This gave gas and heat evolution. The solution was then heated to reflux (52° C.) for sixteen hours. This gave a large amount of white precipitate formation. The suspension was then cooled to room temperature and the ether solution removed by cannula. The residue was dried under vacuum and then suspended in methanol (50 ml). The methanol suspension was then stirred for thirty minutes before the methanol was removed under vacuum. To the residue was added a solution of potassium hydroxide (5 g, 89.1 mmol) in water (100 ml, degassed with nitrogen gas for thirty minutes). This gave heat evolution and the formation of a white precipitate. This was washed with pentane (2*250 ml). The combined pentane washings were dried with sodium sulphate and then transferred into a clean schlenk flask by cannula. The pentane was then removed under vacuum to give a pale yellow oil. Yield=0.9 g. $^{31}P\{1H\}$ NMR: δ=22.3 ppm, >90% pure.

Carbonylation Experimental Procedure

EXAMPLE 1 AND COMPARATIVE EXAMPLE 1-5

Reaction solutions where prepared using standard Schlenk line techniques. Using a nitrogen purge glove box, 134.4 mg (0.000598 moles) of $Pd(OAc)_2$ and 3 equivalents of ligand where weighed into a 500 ml round bottom flask. The flask was then transferred onto a Schlenk line. The palladium and ligand was then dissolved in 180 ml degassed methyl propionate, followed by 120 ml of degassed methanol. This gave an overall solvent composition of 63.4% methyl propionate and 36.6% methanol. Finally 100 µl (2.5 equivalents) of methane sulfonic acid was added to the mixture completing the preparation of the reaction solution, which was then sampled for GC analysis.

The reaction solution was weighed and then charged to the pre-evacuated 2 liter autoclave, which was then pressured in sequence first with 5 bar of hydrogen, 20 bar of ethene and then 40 bar of carbon monoxide. The autoclave was then sealed. This gave an overall pressure of approximately 65 bars. Next the autoclave stirrer drive was switched on, resulting in a drop in the overall pressure, due to the dissolving of gas into solution. This lower pressure was recorded. The autoclave was then heated to 100° C., resulting in a rise in pressure. A pressure reading was taken at 100° C. The reaction was then allowed to proceed for 3 hours, resulting in a drop in overall pressure, as gas from the headspace was converted to methoxycarbonylation products. After the 3 hour reaction period, the pressure of the vessel was again recorded. The reactor was then cooled. When the temperature of the reactor had returned to the original ambient temperature, a final pressure reading was taken. Next the autoclave was vented and discharged, with the products weighed and sampled for GC. A portion of the reaction solution was also collected for visual inspection.

In all 4 pressure readings where recorded:—

1) The pressure of the autoclave before the reaction at ambient temperature
2) The pressure of the autoclave at the 100° C. reaction temperature
3) The pressure of the autoclave at 100° C. after the reaction period
4) The pressure of the autoclave at ambient temperature, after cooling Taking pressure readings in this way, allows gas uptake both at ambient and reaction temperature, to be calculated.

TABLE 1

| Methoxycarbonylation Conditions | |
|---|---|
| | Condition |
| Temperature of reaction | 100 C. |
| CO/ethene pressure at ambient temperature | 60 bar |
| CO:ethene ratio | 2:1 |
| Hydrogen pressure at ambient temperature | 5 bar |
| Pd:ligand | 1:3 |
| Pd:acid | 1:2.5 |
| Solvent composition | 63.4 wt % methyl propionate |
| Palladium Concentration | 2.0 mmoles/litre |
| Addition protocol | Reactant gases added at room temperature |

TABLE 2

Results for cycloalkyl ligands

| Ligand | Example | Weight gain (g) | Wt % MeP Before Reaction | Wt % MeP After Reaction | Gas Uptake at 100° C. (bar) | Gas Uptake at Room T (bar) | TON MeP (mol Pd/mol MeP) % MeP Based | TON MeP (mol Pd/mol MeP) Weight Gain |
|---|---|---|---|---|---|---|---|---|
| 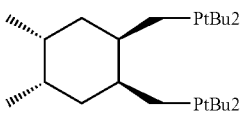 | 1 | 70.7 | 62.75 | 84.53 | 27.5 | 23.5 | 2175 | 2111 |
| 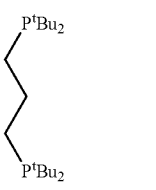 | Comp 1 | 64 | 68.13 | 85.24 | 25.1 | 22.2 | 1833 | 1920 |
| 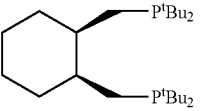 | comp. 2 | 42 | 63.58 | 77.42 | 19.4 | 15.0 | 1277 | 1254 |
| 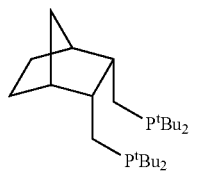 | comp 3 | 35 | 62.44 | 75.18 | 14.9 | 13.5 | 1112 | 1045 |
| 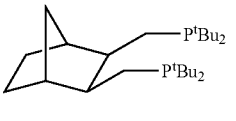 | comp 4 | 24.3 | 63.82 | 73.62 | 10.9 | 8.6 | 795 | 726 |
| 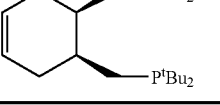 | comp 5 | 16.4 | 61.96 | 71.02 | 9.1 | 8.1 | 646 | 490 |

Carbonylation Examples with Vinyl Acetate

Vinyl Acetate Methoxycarbonylation to 2-Acetoxy Methylpropionate

The vinyl acetate carbonylation experiments were carried out in a 2 liter stainless steel magnetically stirred autoclave equipped with a gas reservoir to allow semi-continuous batch reactions and kinetic data by means of electronic monitoring of the gas reservoir pressure. A solution comprising 67.5 mg (0.300 mmoles) of palladium acetate, 0.600 mmoles of a selected bidentate phosphine, 300 ml of degassed methanol, 50 ml of degassed vinyl acetate and 39 μl (0.60 mmoles) of methanesulphonic acid is added to the autoclave by means of suction from a round-bottomed flask. The autoclave is heated to 60° C. and the reaction is started by the introduction of 10 bar carbon monoxide. The autoclave pressure is held constant by maintaining a carbon monoxide feed from the gas reservoir to top up the reacted gas. After 3 hours the carbon monoxide feed is isolated and the autoclave is cooled before the pressure is vented and the liquid volume is collected for analysis. The reaction rate is given in table 3. The reaction rate is calculated from the rate of change of pressure in the 1 liter feed reservoir assuming ideal gas behaviour and 100% selectivity for methyl ester formation. A sample was analysed by gas chromatography, and the results are shown in table 1 as selectivity.

TABLE 3

| Example | bidentate ligand | Rate[1] | Selectivity[2] |
|---|---|---|---|
| Comparative 6 | A | 351 | 71.61 |
| 2 | B | 5244 | 50.51 | notes:
[1]Rate = moles carbon monoxide consumed/moles palladium/time (hours)
[2]Selectivity = percentage 2-acetoxy methyl propionate in total of 2- and 3-acetoxy methyl propionate produced, as measured by GC.

After distillation of the products of the cyclohexyl carbonylation, 2-acetoxy methyl propionate and 3-acetoxy methyl propionate were collected as different distillates.

CARBONYLATION EXAMPLES 3-9

Vinyl Acetate Hydroxycarbonylation to 3-Acetoxy Propionic Acid

The experiments were carried out in a 2 liter stainless steel magnetically stirred autoclave equipped with a gas reservoir to allow semi-continuous batch reactions and kinetic data by means of electronic monitoring of the gas reservoir pressure. A solution comprising 179.0 mg (0.800 mmoles) of palladium acetate, 2.000 mmoles of a selected bidentate phosphine, 200 ml of degassed acetic acid, 30 ml of degassed demineralised water and 100 ml degassed vinyl acetate is added to the autoclave by means of suction from a round-bottomed flask. The autoclave is heated to 135° C. and the reaction is started by the introduction of 40 bar carbon monoxide. The autoclave pressure is held constant by maintaining a carbon monoxide feed from the gas reservoir to top up the reacted gas. After 3 hours the carbon monoxide feed is isolated and the autoclave is cooled before the pressure is vented and the liquid volume is collected for analysis. The reaction rate is given in table 4. Reaction rate is calculated from the rate of change of pressure in the 1 liter feed reservoir assuming ideal gas behaviour and 100% selectivity for product acid formation. A sample was analysed by gas chromatography, and the results are shown in table 4 as selectivity.

In example 7 the standard catalyst solution is prepared as described above except that 0.15 mmoles of palladium acetate and 0.375 mmoles of selected bidentate ligand are used and hydrogen, 5% of the amount of carbon monoxide used, is added prior to the addition of carbon monoxide.

TABLE 4

| Example | bidentate ligand | temperature | Rate[1] | Selectivity[2] | |
|---|---|---|---|---|---|
| Comparative | | | | | |
| 7 | A | 135 | 332 | 79.83 | |
| 3 | B | 135 | 653 | 91.89 | |
| 4 | B | 125 | 449 | 89.10 | |
| 5 | B | 115 | 325 | 88.68 | |
| 6 | B | 105 | 378 | 88.47 | |
| Comparative | | | | | |
| 8 | A | 135 | 16907 | 88.02 | added H2 |
| 7 | B | 135 | 129374 | 93.65 | added H2 |
| 8 | C | 135 | 1313 | 94.27 | |
| 9 | C | 115 | 621 | 96.13 | |

1. Rate = moles carbon monoxide consumed/moles palladium/time (hours)
2. Selectivity = percentage 3-acetoxy propionic acid in total of 2- and 3-acetoxy propionic acids produced, as measured by GC.
In examples 6 and 7 the standard catalyst solution is prepared except that 0.15 mmol Pd(Oac)2 and 0.375 mmol bidentate ligand are used and 5% hydrogen is added prior to addition of carbon monoxide.
Key: A 1,2-bis(di-t-butylphosphinomethyl)benzene; B cis-1,2-bis(di-t-butylphosphinomethyl)cyclohexane. C cis-1,2-bis(di-t-butylphosphinomethyl) 5,6-dimethyl cyclohexane

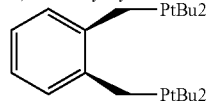

A

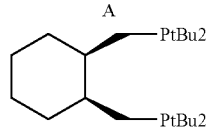

B

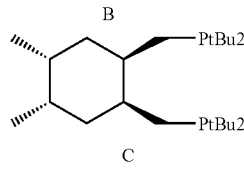

C

After distillation of the products of the cyclohexyl carbonylation, 2-acetoxy propanoic acid (branched) and 3-acetoxy propanoic acid (linear) were collected as different distillates.
Production of Lactate and 3-Hydroxy Esters
Preparation of 3 Hydroxymethylpropionate To 25 g of 3 acetoxy methyl propionate (0.171 moles) was added 25 g MeOH (0.78 moles) containing 1% w/w methane sulphonic acid. The solution was stirred at 60 C for six hours before cooling to room temperature. The sample was analysed by GC, the peak corresponding to 3 acetoxy methyl propionate had completely disappeared and been replaced by a peak corresponding to 3-hydroxymethylpropionate. 3-acetoxy propanoic acid can be treated similarly to produce 3-hydroxy propanoic acid directly or treated in the same way by first esterifying it with methanol.
Preparation of 2-Hydroxymethylpropionate To 25 g of 2-acetoxy methyl propionate (0.171 moles) was added 25 g MeOH (0.78 moles) containing 1% w/w methane sulphonic acid. The solution was stirred at 60 C for six hours before cooling to room temperature. The sample was analysed by GC, the peak corresponding to 2-acetoxy methyl propionate had completely disappeared and been replaced by a peak corresponding to 2-hydroxymethylpropionate. 2-acetoxy propanoic acid can be treated similarly to produce the 2-hydroxy propionic acid directly or treated in the same way by first esterifying it with methanol.
Preparation of 2-Hydroxy Propionic Acid (Lactic Acid)

To 25 g of 2-acetoxy methyl propionate (0.171 moles) was added 25 g MeOH. To this stirred solution was added 20 g sodium hydroxide (0.5 moles) dissolved in 20 ml of water. The solution was stirred for one hour at 50 C before cooling to room temperature. The pH of the solution was then adjusted to pH 3.0 by the slow addition of HCl and the sample stirred for 1 hour. The sample was analysed by GC, the peak corresponding to 2 acetoxy methyl propionate had completely disappeared and been replaced by a peak corresponding to 2 hydroxy propionic acid.
Preparation of 3 Hydroxy Propionic Acid To 25 g of 3 acetoxy methyl propionate (0.171 moles) was added 25 g MeOH. To this stirred solution was added 20 g sodium hydroxide (0.5 moles) dissolved in 20 ml of water. The solution was stirred for one hour at 50 C before cooling to room temperature. The pH of the solution was then adjusted to pH 3.0 by the slow addition of HCl and the sample stirred for 1 hour. The sample was analysed by GC, the peak corresponding to 3 acetoxy methyl propionate had completely disappeared and been replaced by a peak corresponding to 3 hydroxy propionic acid.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A process for the carbonylation of ethylenically unsaturated compounds comprising reacting said compound with carbon monoxide in the presence of a source of hydroxyl groups and of a catalyst system, the catalyst system obtainable by combining:
   (a) a metal of Group 8, 9 or 10 or a compound thereof: and
   (b) a bidentate ligand of general formula (I)

$$X^1(X^2)\text{-}Q^2\text{-}A\text{-}R\text{—}B\text{-}Q^1\text{-}X^3(X^4) \qquad (I)$$

wherein:
   A and B each independently represent lower alkylene;
   R represents a cyclic hydrocarbyl structure having at least one non-aromatic ring to which the $Q^1$ and $Q^2$ atoms are linked, via B and A respectively, on available adjacent cyclic atoms of the at least one ring and which is substituted with at least one substituent on at least one further non-adjacent cyclic atom of the at least one ring;
   wherein each adjacent cyclic atom to the said available adjacent cyclic atom is not substituted in a manner that forms a further ring structure or bridge via the other adjacent cyclic atom to the said available adjacent cyclic atoms in the at least one ring or via an atom adjacent to the said other adjacent atom but outside the at least one ring;
   the groups $X^1$, $X^2$, $X^3$ and $X^4$ independently represent univalent radicals up to 30 atoms having at least one tertiary carbon atom or $X^1$ and $X^2$ and/or $X^3$ and $X^4$ together form a bivalent radical of up to 40 atoms having at least two tertiary carbon atoms wherein each said univalent or bivalent radical is joined via said at least one or two tertiary carbon atoms respectively to the appropriate atom $Q^1$ or $Q^2$; and
   $Q^1$ and $Q^2$ each independently represent phosphorous, arsenic or antimony;
   wherein the ethylenically unsaturated compounds are selected from the group consisting of acetylene, methyl acetylene, propyl acetylene, butadiene, ethylene, propylene, butylene, isobutylene, pentene, pentene nitriles, alkyl pentenoates, methyl 3-pentenoates, pentene acids, vinyl acetate, and octenes.

2. The process as claimed in claim 1, wherein the substituents on the said at least one further non adjacent cyclic atom are selected from the group consisting of lower alkyl, aryl, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, and —$CF_3$, wherein $R^{19}$ to $R^{30}$ each independently represent hydrogen, unsubstituted or substituted aryl or unsubstituted or substituted lower alkyl, and/or may be interrupted by one or more oxygen, sulphur, silicon atoms, or by silano or dialkylsilicon groups.

3. The process as claimed in claim 2, wherein there are two or more said further non-adjacent cyclic atoms in the at least one ring which may each be independently substituted or the substituents may combine to form a further ring structure.

4. The process as claimed in claim 1, wherein the cyclic hydrocarbyl structure which is substituted by A and B at available adjacent positions on the at least one ring has a cis-conformation with respect to the relevant cyclic bond and the A and B substituents.

5. The process as claimed in claim 1, wherein the cyclic hydrocarbyl structure has from 5 up to 30 cyclic atoms.

6. The process as claimed in claim 1, wherein the cyclic hydrocarbyl structure is selected from the group consisting of 4 and/or 5 lower alkylcyclohexane-1,2-diyl, 4 lower alkylcyclopentane-1,2-diyl, 4,5 and/or 6 lower alkylcycloheptane-1,2-diyl, 4,5, 6 and/or 7 lower alkylcyclooctane-1,2-diyl, 4,5, 6,7 and/or 8 lower alkylcyclononane-1,2-diyl, 5 and/or 6 lower alkyl piperidinane-2,3-diyl, 5 and/or 6 lower alkyl morpholinane-2,3-diyl, O-2,3-isopropylidene-2,3-dihydroxyethane-2,3-diyl, cyclopentan-one-3,4-diyl, cyclohexanone-3,4-diyl, 6-lower alkyl cyclohexanone-3,4-diyl, 1-lower alkyl cyclopentene-3,4-diyl, 1 and/or 6 lower alkyl cyclohexene-3,4-diyl, 2 and/or 3 lower alkyl cyclohexadiene-5,6-diyl, 5 lower alkyl cyclohexen-4-one-1,2-diyl, adamantyl-1-2-diyl, 5 and/or 6 lower alkyl tetrahydropyran-2,3 diyl, 6-lower alkyl dihydropyran-2,3 diyl, 2-lower alkyl 1,3 dioxane-5,6-diyl, 5 and/or 6 lower alkyl-1,4 dioxane-2,3-diyl, 2-lower alkyl pentamethylene sulphide 4,5-diyl, 2-lower alkyl-1,3 dithiane-5,6-diyl, 2 and/or 3-lower alkyl 1,4 dithiane-5,6-diyl, tetrahydro-furan-2-one-4,5-diyl, delta-valero lactone 4,5-diyl, gamma-butyrolactone 3,4-diyl, 2H-dihydropyrone 5,6-diyl, glutaric anhydride 3,4-diyl, 1-lower alkyl pyrrolidine-3,4-diyl, 2,3 di-lower alkyl piperazine-5,6-diyl, 2-lower alkyl dihydro imidazole-4,5-diyl, 2,3,5 and/or 6 lower alkyl-1,4,7 triazacyclononane-8,9-diyl, 2,3,4 and/or 10 lower alkyl-1,5,9 triazacyclodecane 6,7-diyl, 2,3-di-lower alkyl thiomorpholine-5,6-diyl, 2-lower alkyl-thiazolidine-4,5-diyl, 4,5-diphenyl-cyclohexane-1,2-diyl, 4 and/or 5-phenyl-cyclohexane-1,2-diyl, 4,5-dimethyl-cyclohexane-1,2-diyl, 4 or 5-methylcyclohexane-1,2-diyl,2,3,4 and/or 5 lower alkyl-decahydronaphthalene 8,9-diyl, bicyclo[4.3.0]nonane-3,4 diyl, 3a,4,5,6,7,7a-hexahydro-1H-inden-5,6-diyl, 1, 2 and/or 3 methyl-3a, 4,5,6,7,7a hexahydro-1H-inden-5,6-diyl, Octahydro-4,7 methano-indene-1,2-diyl, 3a, 4,7,7a-tetrahydro-1H-inden-5,6-diyl, 1,2 and/or 3-dimethyl-3a, 4,5,6,7,7a-hexahydro-1H-inden 5,6-diyls, and 1,3-bis(trimethylsilyl)-3a,4,5,6,7,7a-hexahydro-3H-isobenzofuran-5,6-diyl.

7. The process as claimed in claim 1, wherein the cyclic hydrocarbon bridging group -A-R—B— is selected from the group consisting of the following structures wherein R' and R" represent hydrogen or a substituent and may be the same or different and wherein at least one R' atom is not hydrogen or representing the hetero atom being non substituted if linked directly to a hetero atom:

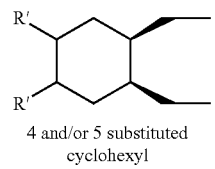

4 and/or 5 substituted cyclohexyl

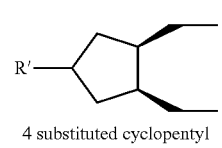

4 substituted cyclopentyl

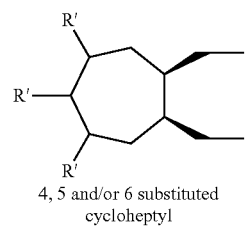

4, 5 and/or 6 substituted cycloheptyl

-continued

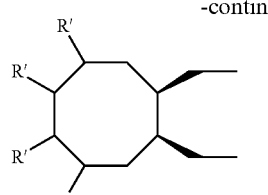

4, 5, 6 and/or 7 substituted
cyclooctyl

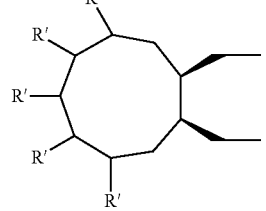

4, 5, 6, 7 and/or 8 substituted
cyclononyl

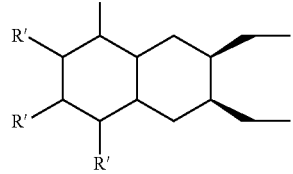

2, 3, 4, and/or 5 substituted
decahydronaphthalene

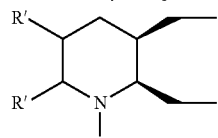

5 and/or 6 substituted
piperidines 5 and/or 6 substituted
morpholines

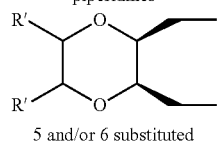

5 and/or 6 substituted
1,4 dioxane

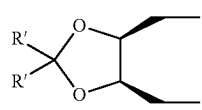 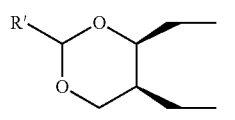

2 - substituted 1,3 dioxane

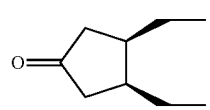

cyclopentanone 6 substituted cyclohexanone

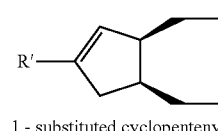

1 - substituted cyclopentenyl   1 and/or 6 - substituted cyclohexenyl

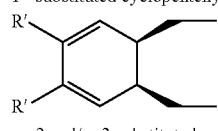

2 and/or 3 substituted
cyclohexadienyl

-continued

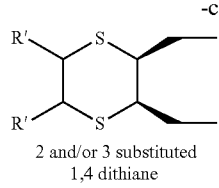 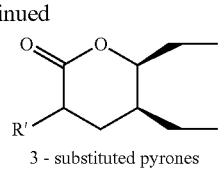

2 and/or 3 substituted     3 - substituted pyrones
1,4 dithiane

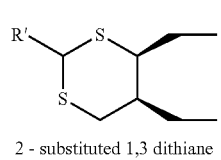 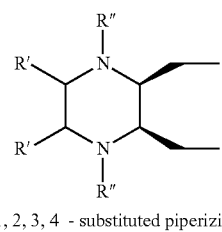

2 - substituted 1,3 dithiane    1, 2, 3, 4 - substituted piperizine

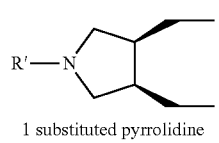 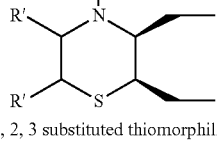

1 substituted pyrrolidine    1, 2, 3 substituted thiomorpholine

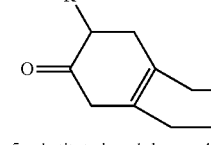 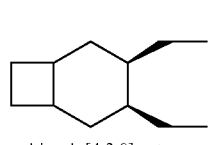

5 substituted cyclohexen-4-one    bicyclo[4.2.0] octane

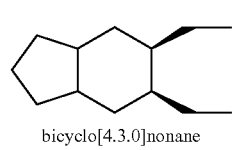 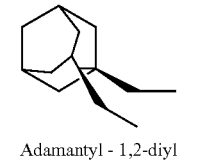

bicyclo[4.3.0]nonane    Adamantyl - 1,2-diyl

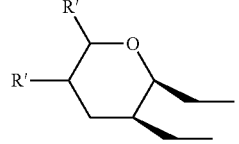 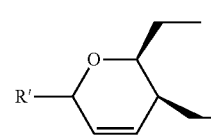

substituted tetrahydropyran    Substituted dihydropyran

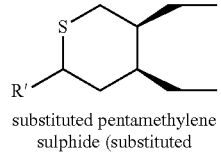 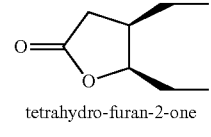

substituted pentamethylene    tetrahydro-furan-2-one
sulphide (substituted
tetrahydro-thiopyran

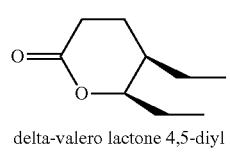 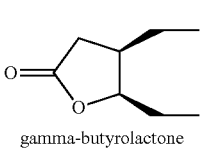

delta-valero lactone 4,5-diyl    gamma-butyrolactone

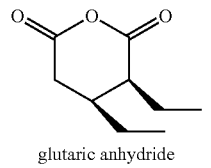 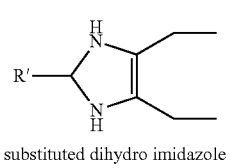

glutaric anhydride    substituted dihydro imidazole

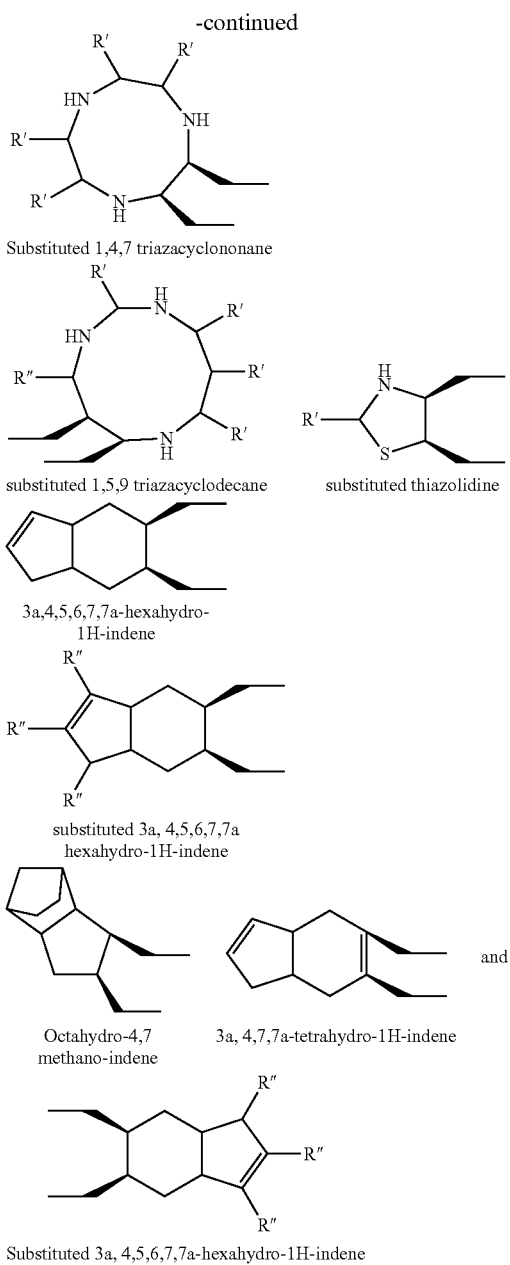

Substituted 1,4,7 triazacyclononane substituted 1,5,9 triazacyclodecane    substituted thiazolidine 3a,4,5,6,7,7a-hexahydro-1H-indene substituted 3a, 4,5,6,7,7a hexahydro-1H-indene Octahydro-4,7 methano-indene    3a, 4,7,7a-tetrahydro-1H-indene    and Substituted 3a, 4,5,6,7,7a-hexahydro-1H-indene where there is more than one stereoisomeric-form possible, all such stereoisomers are intended.

8. The process as claimed in claim 1, wherein the group $X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$, wherein $R^1$ to $R^{12}$ represent lower alkyl, or aryl.

9. The process as claimed in claim 8, wherein the organic groups $R^1$-$R^3$, $R^4$-$R^6$, $R^7$-$R^9$ and/or $R^{10}$-$R^{12}$ or, alternatively, $R^1$-$R^6$ and/or $R^7$-$R^{12}$ when associated with their respective tertiary carbon atom(s) form composite groups which are at least as sterically hindering as t-butyl(s).

10. The process as claimed in claim 1, wherein when cyclic, $X^1$, $X^2$, $X^3$ and/or $X^4$ represent congressyl, norbornyl, 1-norbornadienyl or adamantyl.

11. The process as claimed in claim 1, wherein $X^1$ and $X^2$ together with $Q^2$ to which they are attached form an optionally substituted 2-$Q^2$-tricyclo[3.3.1.1{3,7}]decyl group, or $X^1$ and $X^2$ together with $Q^2$ to which they are attached form a ring system of formula 1a

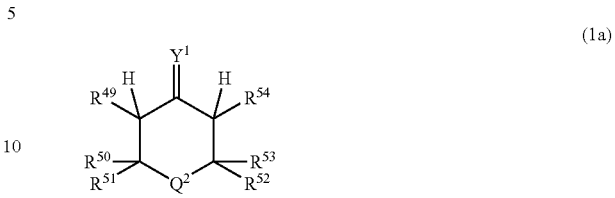

(1a)

wherein $R^{49}$, $R^{54}$ and $R^{55}$, when present, each independently represent hydrogen, lower alkyl or aryl;
wherein $R^{50}$ to $R^{53}$, when present, each independently represent hydrogen, lower alkyl, aryl or Het; and
wherein $Y^1$ represents oxygen, sulfur or N—$R^{55}$.

12. The process as claimed in claim 1, wherein $X^3$ and $X^4$ together with $Q^1$ to which they are attached may form an optionally substituted 2-Q1-tricyclo[3.3.1.1{3,7}]decyl group, or $X^3$ and $X^4$ together with $Q^1$ to which they are attached form a ring system of formula 1b

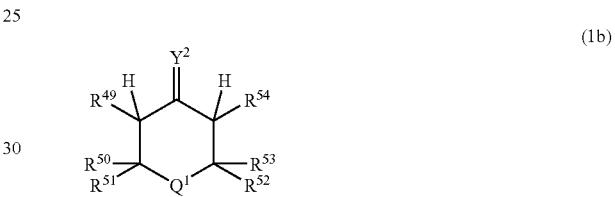

(1b)

wherein $R^{49}$, $R^{54}$ and $R^{55}$, when present, each independently represent hydrogen, lower alkyl or aryl;
wherein $R^{50}$ to $R^{53}$, when present, each independently represent hydrogen, lower alkyl, aryl or Het; and
wherein $Y^2$ represents oxygen, sulfur or N—$R^{55}$.

13. The process as claimed in claim 1, wherein the bidentate ligands are selected from the group consisting of cis-1,2-bis(di-t-butylphosphinomethyl)-4,5-dimethyl cyclohexane; cis-1,2-bis(di-t-butylphosphinomethyl)-5-methylcyclopentane; cis-1,2-bis(2-phosphinomethyl-1,3,5,7-tetramethyl-6,9,10-trioxa-adamantyl)-4,5-dimethylcyclohexane; cis-1,2-bis(2-phosphinomethyl-1,3,5,7-tetramethyl-6,9,10-trioxa-adamantyl) 5-methylcyclopentane; cis-1,2-bis(di-adamantylphosphinomethyl)-4,5 dimethylcyclohexane; cis-1,2-bis(di-adamantylphosphinomethyl)-5-methyl cyclopentane; cis-1-(P,P adamantyl, t-butyl phosphinomethyl)-2-(di-t-butylphosphinomethyl)-4,5-dimethylcyclohexane; cis-1-(P,P adamantyl, t-butyl phosphinomethyl)-2-(di-t-butylphosphinomethyl)-5-methylcyclopentane; cis-1-(2-phosphinomethyl-1,3,5,7-tetramethyl-6,9,10-trioxa-adamantyl)-2-(di-t-butylphosphinomethyl)4,5-dimethylcyclohexane; cis-1-(2-phosphinomethyl-1,3,5,7-tetramethyl-6,9,10-trioxa-adamantyl)-2-(di-t-butylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)-5-methyl cyclohexane; cis-1-(2-phosphinomethyl-1,3,5,7-tetramethyl-6,9,10-trioxa-adamantyl)-2-(diadamantylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)-4,5-dimethyl cyclohexane; cis-1-(di-t- butylphosphinomethyl)-2-(diadamantylphosphinomethyl)-5-methyl cyclopentane; cis-1,2-bis(2-phosphinomethyl-1,3,5-trimethyl-6,9,10-trioxatricyclo-{3.3.1.1[3.7]}decyl)-4,5-dimethyl cyclohexane; cis-1,2-bis(2-phosphinomethyl-1,3,5-trimethyl-6,9,10-trioxatricyclo-{3.3.1.1[3 0.7]}decyl)-5-methyl cyclopentane; cis-1-(2-phosphinomethyl-1,3,5-trimethyl-6,9,10-trioxatricyclo-{3.3.1.1[3.7]}decyl)-2-(di-t-butylphosphinomethyl)-4,5-dimethyl cyclohexane; cis-1-(2-phosphinomethyl-1,3,5-trimethyl-6,9,10-trioxatricyclo-{3.3.1.1[3.7]}decyl)-2-(di-t-butylphosphinomethyl)-5-methyl cyclopentane; cis-1-(2-phosphinomethyl-1,3,5-trimethyl-6,9,10-trioxatricyclo-{3.3.1.1[3.7]}decyl)-2-(diadamantylphosphinomethyl)-4,5-dimethyl cyclohexane; cis-1-(2-phosphinomethyl-1,3,5-trimethyl-6,9,10-trioxatricyclo-{3.3.1.1[3.7]}decyl)-2-(diadamantylphosphinomethyl)-5-methyl cyclopentane; cis-1,2-bis-perfluoro(2-phosphinomethyl-1,3,5,7-tetramethyl-6,9,10-trioxatricyclo {3.3.1.1[3.7]}-decyl)-4,5-dimethyl cyclohexane; cis-1,2-bis-perfluoro(2-phosphinomethyl-1,3,5,7-tetramethyl-6,9,10-trioxatricyclo {3.3.1.1[3.7]}decyl)-5-methyl cyclopentane; cis-1,2-bis-(2-phosphinomethyl-1,3,5,7-tetra(trifluoro-methyl)-6,9,10-trioxatricyclo {3.3.1.1[3.7]}decyl)-4,5-dimethyl cyclohexane; cis-1,2-bis-(2-phosphinomethyl-1,3,5,7-tetra(trifluoro-methyl)-6,9,10-trioxatricyclo {3.3.1.1[3.7]}decyl)-5-methyl cyclopentane

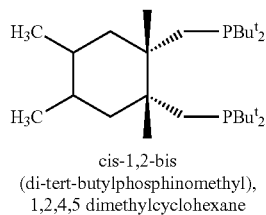

cis-1,2-bis
(di-tert-butylphosphinomethyl),
1,2,4,5 dimethylcyclohexane

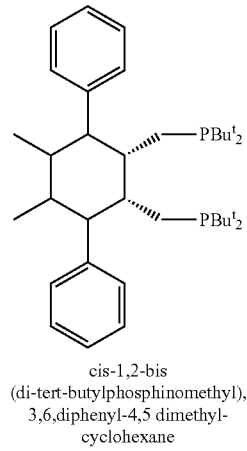

cis-1,2-bis
(di-tert-butylphosphinomethyl),
3,6,diphenyl-4,5 dimethyl-
cyclohexane

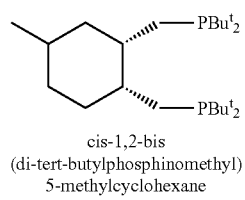

cis-1,2-bis
(di-tert-butylphosphinomethyl)
5-methylcyclohexane

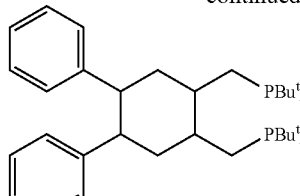

cis-1,2 bis
(di-tert-butyl(phosphinomethyl)-
4,5 diphenyl cyclohexane

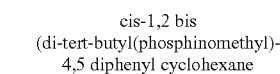

cis-5,6-bis
(di-tert-butylphosphinomethyl)-
1,3-bis(trimethylsilyl)-
3a,4,5,6,7,7a-hexahydro-
1,3H-isobenzofuran 14. The process as claimed in claim 1, wherein the ratio of linear:branched product from the carbonylation process is greater than 0.5:1.

15. The process as claimed in claim 1, wherein the ethylenically unsaturated compounds are selected from the group consisting of ethylene, vinyl acetate, butadiene, alkyl pentenoates, pentenenitriles, pentene acids, 3-pentenoic acid, acetylene and propylene.

16. A process as claimed in claim 1, wherein at least one of the substituents on the said at least one further non adjacent cyclic atom is a group Y where Y represents a group which is at least as sterically hindering as phenyl and when there are two or more substituents Y they are each as sterically hindering as phenyl and/or combine to form a group which is more sterically hindering than phenyl.

17. A process according to claim 16, wherein Y represents $S^{l}R^{40}R^{41}R^{42}$;
wherein $S^{l}$ represents Si, C, or aryl;
when $S^{l}$ is aryl,
$R^{40}$, $R^{41}$ and $R^{42}$ are independently hydrogen, lower alkyl, —$BQ^{3}$-$X^{3}(X^{4})$ (wherein $Q^{3}$ is phosphorous, arsenic or antimony), aryl, arylene, alkaryl, arylenalkyl, alkenyl, alkynyl, het, halo, cyano, nitro, —$OR^{19}$, —$OC(O)R^{20}$, $C(O)R^{21}$, $C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, —$CF_{3}$, —$SiR^{71}R^{72}R^{73}$ or alkylphosphorous;
when $S^{l}$ is Si or C,
$R^{40}$, $R^{41}$ and $R^{42}$ are independently hydrogen, lower alkyl, aryl, arylene, alkaryl, aralkyl, arylenalkyl, alkenyl, alkynyl, het, halo, cyano, nitro, —$OR^{19}$, —$OC(O)R^{20}$, —$C(O)R^{21}$, —$C(O)OR^{22}$, —$N(R^{23})R^{24}$, $C(O)N(R^{25})R^{26}$, $SR^{29}$, —$C(O)SR^{30}$, —$C(S)N(R^{27})R^{28}$, —$CF_{3}$, —$SiR^{71}R^{72}R^{73}$, or alkylphosphorous,
wherein at least one of $R^{40}$-$R^{42}$ is not hydrogen and
wherein $R^{19}$, $R^{20}$, $R^{22}$-$R^{30}$ each independently represent hydrogen, unsubstituted or substituted aryl or unsubstituted or substituted lower alkyl, and/or may be interrupted by one or more oxygen, sulphur, silicon atoms, or by silano or dialkylsilicon groups;

wherein $R^{21}$ represents hydrogen, unsubstituted or substituted aryl or unsubstituted or substituted lower alkyl, and/or may be interrupted by one or more oxygen, sulphur, silicon atoms, or by silano or dialkylsilicon groups, nitro, halo, amino or thio; and wherein $R^{71}$-$R^{73}$ are lower alkyl, aryl, arylene, alkaryl, aralkyl, arylenalkyl, alkenyl, or alkynyl.

18. The process as claimed in claim 1, wherein the bidentate ligand is

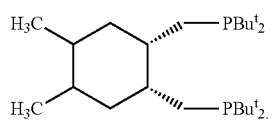

-continued

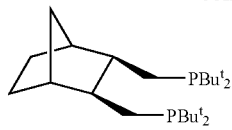

(2-endo, 3-endo)-bicyclo[2.2.1]heptane-2,3-bis(di-tert-butylphosphinomethyl)

19. The process as claimed in claim 7, wherein the cyclic hydrocarbon bridging group -A-R—B— is

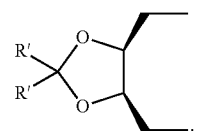

* * * * *